United States Patent
Jin et al.

(10) Patent No.: US 8,268,819 B2
(45) Date of Patent: Sep. 18, 2012

(54) HEXAHYDROOXAZINOPTERINE COMPOUNDS

(75) Inventors: Bohan Jin, San Diego, CA (US); Nicholas Scorah, San Diego, CA (US); Qing Dong, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/429,865

(22) Filed: Mar. 26, 2012

(65) Prior Publication Data

US 2012/0178924 A1 Jul. 12, 2012

Related U.S. Application Data

(62) Division of application No. 12/869,452, filed on Aug. 26, 2010, now Pat. No. 8,163,755.

(60) Provisional application No. 61/238,064, filed on Aug. 28, 2009, provisional application No. 61/313,608, filed on Mar. 12, 2010.

(51) Int. Cl.
*A61K 31/5383* (2006.01)
*C07D 498/14* (2006.01)
*A61P 35/00* (2006.01)

(52) U.S. Cl. .................. 514/230.2; 544/101; 544/73

(58) Field of Classification Search .................. None
See application file for complete search history.

(56) References Cited

FOREIGN PATENT DOCUMENTS

| WO | WO/03/076440 | 9/2003 |
|----|----|----|
| WO | WO/2006/005915 | 1/2006 |
| WO | WO/2006/086494 | 8/2006 |
| WO | WO/2008/023180 | 2/2008 |
| WO | WO/2009/046383 | 4/2009 |
| WO | WO2012/048129 | * 10/2011 |

OTHER PUBLICATIONS

Neitz et al., caplus an 2012:534299.*
Eduardo Vilar et al. "Pushing the Envelope in the mTOR Pathway: The Second Generation of Inhibitors" Mol Cancer Ther 2011;10:395-403. Published OnlineFirst Jan. 7, 2011.

* cited by examiner

*Primary Examiner* — Sun Jae Loewe
(74) *Attorney, Agent, or Firm* — David M. Stemerick

(57) ABSTRACT

The present invention relates to intermediates of the formula

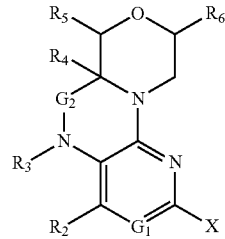

wherein $G_1$ is N; $G_2$ is selected from the group consisting of C=O and $CH_2$; X is a halogen; and the other groups are defined herein.

8 Claims, No Drawings

HEXAHYDROOXAZINOPTERINE COMPOUNDS

RELATED APPLICATIONS

This application claims the benefit of U.S. Provisional Application Nos. 61/238,064, filed Aug. 28, 2009; 61/313,608, filed Mar. 12, 2010; and 12/869,452, filed Aug. 26, 2010; which are incorporated herein by reference.

FIELD OF THE INVENTION

The present invention relates to medicinal chemistry and pharmaceutical science. Provided herein are compounds that inhibit mammalian target of rapamycin (mTOR).

BACKGROUND OF THE INVENTION mTOR is a serine/threonine kinase and has been identified as a regulator of protein synthesis as well as cell growth and proliferation. Also, mTOR has been shown to regulate the response of tumor cells to nutrients and growth factors as well as the ability of tumors to promote angiogenesis. Thus, inhibitors of mTOR activity are being actively studied as potential anti-proliferative agents. Currently inhibitors of mTOR are approved for immunosuppression and cancer treatment.

Inhibition of mTOR function by small molecules results in a loss of transmission of upstream activating signals (i.e., from growth factor receptors) to downstream effectors of cell growth. Rapamycin, an inhibitor of mTOR, inhibits proliferation or growth of cells derived from a range of tissue types such as smooth muscle and T-cells as well as cells derived from a diverse range of tumor types including rhabdomyosarcoma, neuroblastoma, glioblastoma and medulloblastoma, small cell lung cancer, osteosarcoma, pancreatic carcinoma and breast and prostate carcinoma. Moreover, rapamycin and its derivatives have shown the ability to potentiate the cytotoxicity of a number of common cancer chemotherapies including cisplatin, camptothecin and doxorubicin.

It has been shown that mTOR functions in two distinct complexes (mTORC1 and mTORC2). Rapamycin primarily inhibits the mTORC1 complex while largely sparing mTORC2 activity. Thus, one strategy is to identify compounds that are capable of inhibiting mTORC1 and mTORC2 mediated activity in the cell. The compounds of the present invention are such inhibitors of mTOR and are useful to treat disorders associated with mTOR.

In addition, mTOR Complex 1-S6K1 integrates various extrinsic signals that regulate cell growth and metabolism. Experiments with rapamycin provided a link between mTOR Complex 1-S6K1 and adipogenesis. Also it has been demonstrated that S6K1-deficient mice are protected from diet and age induced obesity.

Certain inhibitors of PI3K are disclosed in WO2006/005915. Certain inhibitors of mTOR and/or PI3K are disclosed in WO 2008/023180.

SUMMARY OF THE INVENTION

The present invention provides compounds of formula I:

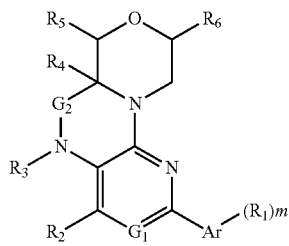

$G_1$ is selected from the group consisting of N and $CR_7$;
$G_2$ is selected from the group consisting of C=O and $CH_2$;
Ar is selected from the group consisting of $C_{4-14}$ aryl and $C_{1-10}$ heteroaryl;
m is 0, 1, 2, 3, or 4;
$R_1$ is, each time taken, independently selected from the group consisting of halo, cyano, optionally substituted $C_{1-6}$ alkyl, $C_{1-8}$ sulfonyl, optionally substituted $C_{2-4}$ alkenyl, optionally substituted $C_{2-4}$ alkynyl, optionally substituted $C_{1-4}$ alkoxy, $C_{0-8}$ alkylamino, optionally substituted $C_{4-14}$ aryl, optionally substituted $C_{4-14}$ aryloxy, optionally substituted $C_{1-10}$ heteroaryloxy, $C_{1-5}$ oxycarbonyl, $C_{1-5}$ carbonyloxy, optionally substituted $C_{3-8}$ cycloalkyl, optionally substituted $C_{3-6}$ heterocycloalkyl, optionally substituted $C_{1-10}$ heteroaryl, hydroxy, nitro, —C(O)NR$_8$R$_9$, —NHC(O)NR$_8$R$_9$, —NHC(O)OR$_{10}$, —NH(SO$_2$)NHR$_8$, —NHC(O)NHNR$_8$R$_9$, —NHC(S)NR$_8$R$_9$, —NHC(=NR$_{11}$)NR$_8$R$_9$, —NHC(SR$_{12}$)NR$_8$R$_9$, and —NHC(=NR$_{11}$)OR$_{13}$;
$R_2$ is selected from the group consisting of hydrogen, halo, cyano, optionally substituted $C_{1-6}$ alkyl, $C_{1-8}$ sulfonyl, optionally substituted $C_{2-4}$ alkenyl, optionally substituted $C_{2-4}$ alkynyl, optionally substituted $C_{1-4}$ alkoxy, $C_{0-8}$ alkylamino, optionally substituted $C_{4-14}$ aryl, optionally substituted $C_{4-14}$ aryloxy, $C_{1-5}$ oxycarbonyl, $C_{1-5}$ carbonyloxy, optionally substituted $C_{3-6}$ heterocycloalkyl, optionally substituted $C_{1-10}$ heteroaryl, hydroxy, and nitro;
$R_3$ is selected from the group consisting of hydrogen, optionally substituted $C_{1-6}$ alkyl, optionally substituted $C_{3-8}$ cycloalkyl, and optionally substituted $C_{3-6}$ heterocycloalkyl;
$R_4$ is selected from the group consisting of methyl and trifluoromethyl;
$R_5$ is selected from the group consisting of hydrogen, halo, optionally substituted $C_{1-6}$ alkyl, optionally substituted $C_{2-4}$ alkenyl, and optionally substituted $C_{3-8}$ cycloalkyl;
$R_6$ is selected from the group consisting of hydrogen, halo, optionally substituted $C_{1-6}$ alkyl, optionally substituted $C_{2-4}$ alkenyl, and optionally substituted $C_{3-8}$ cycloalkyl; or
$R_5$ and $R_6$ are taken together to form an optionally substituted $C_1$-$C_3$ alkylenyl; or
$R_4$ and $R_5$ are taken together to form an optionally substituted $C_1$-$C_3$ alkylenyl; or
$R_4$ and $R_6$ are taken together to form an optionally substituted $C_1$-$C_3$ alkylenyl; and
$R_7$ is selected from the group consisting of hydrogen, $C_{0-8}$ alkylamino, $C_{1-7}$ amido, $C_{1-9}$ amide, $C_{1-5}$ carbamoyl, $C_{1-6}$ sulfonylamido, $C_{0-6}$ sulfonylamino, $C_{1-5}$ ureido, optionally substituted $C_{1-4}$ alkyl, optionally substituted $C_{1-4}$ alkoxy, cyano, halo, hydroxyl, nitro, $C_{1-5}$ oxycarbonyl, and $C_{1-8}$ sulfonyl;
$R_8$ is, each time taken, independently selected from the group consisting of hydrogen, optionally substituted $C_{1-6}$ alkyl, optionally substituted $C_{3-8}$ cycloalkyl, optionally substituted $C_{4-14}$ aryl, optionally substituted $C_{3-6}$ heterocycloalkyl, and optionally substituted $C_{1-10}$ heteroaryl;
$R_9$ is, each time taken, independently selected from the group consisting of hydrogen, optionally substituted $C_{1-6}$ alkyl, optionally substituted $C_{3-8}$ cycloalkyl, optionally substituted $C_{4-14}$ aryl, optionally substituted $C_{3-6}$ heterocycloalkyl, and optionally substituted $C_{1-10}$ heteroaryl;
$R_{10}$ is, each time taken, independently selected from the group consisting of optionally substituted $C_{1-6}$ alkyl, optionally substituted $C_{3-8}$ cycloalkyl, optionally substituted $C_{4-14}$ aryl, and optionally substituted $C_{3-6}$ heterocycloalkyl;
$R_{11}$ is, each time taken, independently selected from the group consisting of hydrogen, optionally substituted $C_{1-6}$ alkyl, optionally substituted $C_{1-6}$ alkoxy, optionally substituted $C_{3-8}$ cycloalkyl, optionally substituted $C_{4-14}$ aryl, optionally substituted $C_{3-6}$ heterocycloalkyl, optionally substituted $C_{1-10}$ heteroaryl, cyano, and nitro;

$R_{12}$ is, each time taken, independently selected from the group consisting of optionally substituted $C_{1-6}$ alkyl and optionally substituted phenyl; and $R_{13}$ is, each time taken, independently selected from the group consisting of optionally substituted $C_{1-6}$ alkyl, optionally substituted $C_{3-8}$ cycloalkyl, and optionally substituted $C_{4-14}$ aryl; or the pharmaceutically acceptable salts thereof.

The present invention also provides pharmaceutical compositions, comprising: a compound of formula I and a pharmaceutically acceptable excipient.

The compounds of the invention are inhibitors of mTOR they are useful for the treatment of conditions associated with mTOR, including cancer. Thus, the invention provides methods of treating conditions associated with mTOR, comprising: administering to a patient in need thereof an effective amount of a compound of formula I. Further, the present invention provides for the use of compounds of formula I, including for the manufacture of a medicament, each specifically including for the treatment of particular conditions associated with mTOR.

The present invention also provides an article of manufacture: comprising at least one compound of formula I and a label. Also provided are kits comprising at least one compound of the invention, a label, and apparatus for administration of the inhibitor.

The present invention also provides processes from making mTOR inhibitors and intermediates thereof.

DETAILED DESCRIPTION OF THE INVENTION

The term "$C_{2-4}$ alkenyl" refers to a straight or branched alkenyl chain having from two to four carbon atoms and one or more carbon-carbon double bonds, and includes ethylene, propylene, iso-propylene, butylene, iso-butylene, sec-butylene, and the like.

The term "optionally substituted $C_{2-4}$ alkenyl" refers to a $C_{2-4}$ alkenyl optionally having from 1 to 3 substituents independently selected from the group consisting of $C_{1-4}$ alkoxy, $C_{1-9}$ amide, $C_{1-5}$ oxycarbonyl, cyano, $C_{3-8}$ cycloalkyl, halo, hydroxy, oxo, optionally substituted $C_{1-10}$ heteroaryl, and optionally substituted phenyl.

The term "$C_{1-4}$ alkyl" refers to a straight or branched alkyl chain having from one to four carbon atoms.

The term "optionally substituted $C_{1-4}$ alkyl" refers to a $C_{1-4}$ alkyl optionally having from 1 to 5 substituents independently selected from the group consisting of $C_{2-4}$ alkenyl, optionally substituted $C_{1-4}$ alkoxy, $C_{1-4}$ thioalkoxy, $C_{1-9}$ amide, $C_{0-8}$ alkylamino, $C_{1-5}$ oxycarbonyl, $C_{1-8}$ sulfonyl, cyano, optionally substituted $C_{3-8}$ cycloalkyl, $C_{3-8}$ cycloalkoxy, halo, hydroxy, nitro, oxo, optionally substituted $C_{3-6}$ heterocycloalkyl, optionally substituted $C_{1-10}$ heteroaryl, and optionally substituted phenyl.

More particularly "optionally substituted $C_{1-4}$ alkyl" refers to a $C_{1-4}$ alkyl optionally having from 1 to 5 substituents independently selected from the group consisting of $C_{1-4}$ alkoxy, $C_{1-9}$ amide, $C_{0-8}$ alkylamino, $C_{1-5}$ oxycarbonyl, cyano, $C_{3-8}$ cycloalkyl, halo, hydroxy, $C_{3-6}$ heterocycloalkyl optionally substituted on any ring nitrogen by $C_{1-4}$ alkyl, $C_{1-10}$ heteroaryl, and optionally substituted phenyl.

The term "$C_{1-6}$ alkyl" refers to a straight or branched alkyl chain having from one to six carbon atoms.

The term "optionally substituted $C_{1-6}$ alkyl" refers to a $C_{1-6}$ alkyl optionally having from 1 to 7 substituents independently selected from the group consisting of $C_{0-8}$ alkylamino, $C_{2-4}$ alkenyl, optionally substituted $C_{1-4}$ alkoxy, $C_{1-4}$ thioalkoxy, $C_{1-9}$ amide, $C_{1-5}$ oxycarbonyl, $C_{1-8}$ sulfonyl, cyano, optionally substituted $C_{3-8}$ cycloalkyl, halo, hydroxy, oxo, optionally substituted $C_{1-10}$ heteroaryl, optionally substituted $C_{3-6}$ heterocycloalkyl, optionally substituted $C_{1-10}$ heteroaryl, and optionally substituted phenyl.

More particularly "optionally substituted $C_{1-6}$ alkyl" refers to a $C_{1-6}$ alkyl optionally having from 1 to 7 substituents independently selected from the group consisting of $C_{1-4}$ alkoxy, $C_{1-9}$ amide, $C_{0-8}$ alkylamino, $C_{1-5}$ oxycarbonyl, cyano, $C_{3-8}$ cycloalkyl, halo, hydroxy, $C_{3-6}$ heterocycloalkyl optionally substituted on any ring nitrogen by $C_{1-4}$ alkyl, $C_{1-10}$ heteroaryl, and optionally substituted phenyl.

The term "$C_1$-$C_3$ alkylenyl" refers to a $C_1$-$C_3$ alkylene having an attachment at each end and consists of —$CH_2$—, —$CH_2CH_2$—, and —$CH_2CH_2CH_2$—.

The term "optionally substituted $C_1$-$C_3$ alkylenyl" refers to a $C_1$-$C_3$ alkylene optionally having from 1 to 2 $C_{1-6}$ alkyl groups.

The term "$C_{1-8}$ sulfonyl" refers to a sulfonyl linked to a $C_{1-6}$ alkyl group, $C_{3-8}$ cycloalkyl, or an optionally substituted phenyl.

The term "$C_{1-4}$ alkoxy" refers to a $C_{1-4}$ alkyl attached through an oxygen atom.

The term "optionally substituted $C_{1-4}$ alkoxy" refers to a $C_{1-4}$ alkoxy optionally having from 1 to 6 substituents independently selected from the group consisting of $C_{2-4}$ alkenyl, $C_{1-4}$ alkoxy, $C_{1-9}$ amide, $C_{1-5}$ oxycarbonyl, cyano, optionally substituted $C_{3-8}$ cycloalkyl, halo, hydroxy, optionally substituted $C_{1-10}$ heteroaryl, and optionally substituted phenyl. While it is understood that where the optional substituent is $C_{1-4}$ alkoxy, cyano, halo, or hydroxy then the substituent is generally not alpha to the alkoxy attachment point, the term "optionally substituted $C_{1-4}$ alkoxy" includes stable moieties and specifically includes trifluoromethoxy, difluoromethoxy, and fluoromethoxy.

More particularly "optionally substituted $C_{1-4}$ alkoxy" refers to a $C_{1-4}$ alkoxy optionally having from 1 to 6 substituents independently selected from the group consisting of $C_{1-4}$ alkoxy, cyano, $C_{3-8}$ cycloalkyl, halo, hydroxy, and phenyl.

The term "$C_{2-4}$ alkynyl" refers to a straight or branched alkynyl chain having from two to six carbon atoms and one or more carbon-carbon triple bonds.

The term "optionally substituted $C_{2-4}$ alkynyl" refers to a $C_{2-6}$ alkynyl optionally having from 1 to 3 substituents independently selected from the group consisting of $C_{1-4}$ alkoxy, $C_{1-9}$ amide, $C_{1-5}$ oxycarbonyl, cyano, $C_{3-8}$ cycloalkyl, halo, hydroxy, oxo, optionally substituted $C_{1-10}$ heteroaryl, and optionally substituted phenyl.

The term "$C_{1-9}$ amide" refers to an amide having two groups independently selected from the group consisting of hydrogen, $C_{1-4}$ alkyl, and optionally substituted phenyl, for example, —$CONH_2$, —$CONHCH_3$, and —$CON(CH_3)_2$.

The term "$C_{1-7}$ amido" refers to a —NHC(O)R group in which R is selected from the group consisting of hydrogen, $C_{1-6}$ alkyl, and optionally substituted phenyl.

The term "$C_{1-5}$ carbamoyl" refers to an O- or N-linked carbamate having a terminal $C_{1-4}$ alkyl.

The term "$C_{1-5}$ ureido" refers to a urea optionally having a $C_{1-4}$ alkyl.

The term "$C_{0-8}$ alkylamino" refers to an amino optionally having one or two $C_{1-4}$ alkyl.

The term "$C_{4-14}$ aryl" refers to a monocyclic and polycyclic unsaturated, conjugated hydrocarbon having aromatic character and having four to fourteen carbon atoms, and includes phenyl, biphenyl, indenyl, cyclopentyldienyl, fluorenyl, and naphthyl.

More particularly "$C_{4-14}$ aryl" refers to phenyl.

The term "optionally substituted $C_{4-14}$ aryl" refers to a $C_{4-14}$ aryl optionally having 1 to 5 substituents independently selected from the group consisting of $C_{0-8}$ alkylamino, $C_{1-7}$ amido, $C_{1-9}$ amide, $C_{1-5}$ carbamoyl, $C_{1-6}$ sulfonylamido, $C_{0-6}$ sulfonylamino, $C_{1-5}$ ureido, $C_{1-4}$ alkyl, $C_{1-4}$ alkoxy, cyano, halo, hydroxyl, $C_{1-5}$ oxycarbonyl, trifluoromethyl, trifluoromethoxy, and $C_{1-8}$ sulfonyl.

More particularly "optionally substituted $C_{4-14}$ aryl" refers to a $C_{4-14}$ aryl optionally having 1 to 5 substituents independently selected from the group consisting of $C_{1-4}$ alkyl, $C_{1-4}$ alkoxy, cyano, halo, $C_{1-5}$ oxycarbonyl, trifluoromethyl, and trifluoromethoxy.

The term "$C_{4-14}$ aryloxy" refers to a $C_{4-14}$ aryl attached through an oxygen atom.

The term "optionally substituted $C_{4-14}$ aryloxy" refers to a $C_{4-14}$ aryloxy optionally having 1 to 5 substituents independently selected from the group consisting of $C_{0-8}$ alkylamino, $C_{1-4}$ alkyl, $C_{1-4}$ alkoxy, cyano, halo, hydroxyl, nitro, $C_{1-8}$ sulfonyl, and trifluoromethyl.

The term "$C_{1-5}$ oxycarbonyl" refers to an oxycarbonyl group ($-CO_2H$) and $C_{1-4}$ alkyl ester thereof.

The term "$C_{1-5}$ carbonyloxy" refers to a carbonyloxy group ($-O_2CR$), for example acetoxy.

The term "$C_{3-8}$ cycloalkyl" refers to an alkyl ring having from three to eight carbon atoms, and includes cyclopropyl, 2-methyl cyclopropyl, cyclobutyl, cyclopentyl, cyclohexyl, and the like.

The term "optionally substituted $C_{3-8}$ cycloalkyl" refers to a $C_{3-8}$ cycloalkyl optionally having from 1 to 6 substituents independently selected from the group consisting of optionally substituted $C_{1-4}$ alkyl, $C_{2-4}$ alkenyl, optionally substituted $C_{1-4}$ alkoxy, $C_{1-9}$ amide, $C_{1-7}$ amido, $C_{0-8}$ alkylamino, $C_{1-5}$ oxycarbonyl, cyano, $C_{3-8}$ cycloalkyl, $C_{3-8}$ cycloalkoxy, halo, hydroxy, nitro, oxo, optionally substituted $C_{1-10}$ heteroaryl, and optionally substituted phenyl.

More particularly "optionally substituted $C_{3-8}$ cycloalkyl" refers to a $C_{3-8}$ cycloalkyl optionally having from 1 to 3 substituents independently selected from the group consisting of $C_{1-4}$ alkyl, $C_{1-4}$ alkoxy, halo, and hydroxy.

The term "$C_{3-8}$ cycloalkyl$C_{1-4}$ alkyl" refers to a $C_{1-4}$ alkyl substituted by a $C_{3-8}$ cycloalkyl. It is understood that the $C_{3-8}$ cycloalkyl can be attached in any manner, including pendant, fused, or spiro.

The term "$C_{3-8}$ cycloalkoxy" refers to a $C_{3-8}$ cycloalkyl attached through an oxygen atom.

The terms "halogen" and "halo" refers to a chloro, fluoro, bromo or iodo atom.

The term "$C_{3-6}$ heterocycloalkyl" refers to a 4 to 10 membered monocyclic saturated or partially (but not fully) unsaturated ring having one to four heteroatoms selected from the group consisting of nitrogen, oxygen, and sulfur. It is understood that where sulfur is included that the sulfur may be either $-S-$, $-SO-$, and $-SO_2-$. For example, but not limiting, the term includes azetidine, pyrrolidine, piperidine, piperazine, morpholine, thiomorpholine, oxetane, dioxolane, tetrahydropyran, tetrahydrothiopyran, dioxidotetrahydrothiopyran, tetrahydrofuran, hexahydropyrimidine, tetrahydropyrimidine, dihydroimidazole, and the like. It is understood that a $C_{3-6}$ heterocycloalkyl can be attached as a substituent through a ring carbon or a ring nitrogen atom.

More particularly "$C_{3-6}$ heterocycloalkyl" is selected from the group consisting of pyrrolidine, piperidine, piperazine, morpholine, oxetane, tetrahydropyran, tetrahydrothiopyran, dioxidotetrahydrothiopyran, and tetrahydrofuran.

The term "optionally substituted $C_{3-6}$ heterocycloalkyl" refers to a $C_{3-6}$ heterocycloalkyl optionally substituted on the ring carbons with 1 to 4 substituents independently selected from the group consisting of optionally substituted $C_{1-4}$ alkyl, $C_{2-4}$ alkenyl, optionally substituted $C_{1-4}$ alkoxy, $C_{1-9}$ amide, $C_{1-7}$ amido, $C_{0-8}$ alkylamino, $C_{1-5}$ oxycarbonyl, cyano, optionally substituted $C_{3-8}$ cycloalkyl, $C_{3-8}$ cycloalkoxy, halo, hydroxy, nitro, oxo, and optionally substituted phenyl; and optionally substituted on any ring nitrogen with a substituent independently selected from the group consisting of optionally substituted $C_{1-4}$ alkyl, $C_{2-4}$ alkenyl, $C_{3-8}$ cycloalkyl, optionally substituted $C_{3-6}$ heterocycloalkyl, optionally substituted $C_{1-10}$ heteroaryl, and optionally substituted phenyl.

More particularly "optionally substituted $C_{3-6}$ heterocycloalkyl" refers to a $C_{3-6}$ heterocycloalkyl optionally substituted on the ring carbons with 1 to 4 substituents independently selected from the group consisting of $C_{1-4}$ alkyl, $C_{1-4}$ alkoxy, halo, and hydroxy and optionally substituted on any ring nitrogen with a $C_{1-4}$ alkyl.

The term "$C_{1-10}$ heteroaryl" refers to a five to twelve membered monocyclic and polycyclic having unsaturated, conjugated ring(s) having aromatic character and having one to ten carbon atoms and one or more, typically one to four, heteroatoms selected from the group consisting of nitrogen, oxygen, and sulfur. For example, but not limiting, the term includes azepine, diazepine, furan, thiophene, pyrrole, imidazole, isothiazole, isoxazole, oxadiazole, oxazole, pyrazine, pyrazole, pyridazine, pyridine, pyrimidine, thiazole, thiadiazole, triazole, tetrazole, benzazepine, benzodiazepine, benzofuran, benzothiophene, benzimidazole, imidazopyridine, pyrazolopyridine, pyrrolopyridine, quinazoline, thienopyridine, indolizine, imidazopyridine, quinoline, isoquinoline, indole, isoindole, benzoxazole, benzoxadiazole, benzopyrazole, benzothiazole, and the like. It is understood that a $C_{1-10}$ heteroaryl can be attached as a substituent through a ring carbon or a ring nitrogen atom where such an attachment mode is available, for example for an indole, imidazole, azepine, triazole, pyrazine, etc.

More particularly "$C_{1-10}$ heteroaryl" is selected from the group consisting of furan, thiophene, pyrrole, imidazole, isothiazole, isoxazole, oxadiazole, oxazole, pyrazine, pyrazole, pyridazine, pyridine, pyrimidine, thiazole, thiadiazole, and triazole.

The term "optionally substituted $C_{1-10}$ heteroaryl" refers to a $C_{1-10}$ heteroaryl optionally having 1 to 5 substituents on carbon independently selected from the group consisting of $C_{1-7}$ amido, $C_{0-8}$ alkylamino, $C_{1-9}$ amide, $C_{1-5}$ carbamoyl, $C_{1-6}$ sulfonylamido, $C_{0-6}$ sulfonylamino, $C_{1-5}$ ureido, optionally substituted $C_{1-4}$ alkyl, optionally substituted $C_{1-4}$ alkoxy, cyano, halo, hydroxyl, oxo, nitro, $C_{1-5}$ oxycarbonyl, and $C_{1-8}$ sulfonyl and optionally having a substituent on each nitrogen independently selected from the group consisting of optionally substituted $C_{1-4}$ alkyl, $C_{1-8}$ sulfonyl, optionally substituted $C_{3-6}$ heterocycloalkyl, and optionally substituted phenyl.

More particularly "optionally substituted $C_{1-10}$ heteroaryl" refers to a $C_{1-10}$ heteroaryl optionally having 1 to 5 substituents on carbon independently selected from the group consisting of $C_{1-7}$ amido, $C_{0-8}$ alkylamino, $C_{1-9}$ amide, $C_{1-5}$ carbamoyl, $C_{1-6}$ sulfonylamido, $C_{0-6}$ sulfonylamino, $C_{1-5}$ ureido, $C_{1-4}$ alkyl, $C_{1-4}$ alkoxy, cyano, halo, hydroxyl, oxo, $C_{1-5}$ oxycarbonyl, trifluoromethyl, trifluoromethoxy, and $C_{1-8}$ sulfonyl and optionally having a substituent on each nitrogen a $C_{1-4}$ alkyl.

Even more particularly "optionally substituted $C_{1-10}$ heteroaryl" refers to a $C_{1-10}$ heteroaryl optionally having 1 to 5 substituents independently selected from the group consisting of $C_{1-4}$ alkyl, $C_{1-4}$ alkoxy, cyano, halo, $C_{1-5}$ oxycarbonyl, trifluoromethyl, and trifluoromethoxy.

The term "oxo" refers to an oxygen atom having a double bond to the carbon to which it is attached to form the carbonyl of a ketone or aldehyde. It is understood that as the term is used herein oxo refers to doubly bonded oxygen attached to the group which has the oxo substituent, as opposed to the oxo group being pendant as a formyl group. For example, an acetyl radical is contemplated as an oxo substituted alkyl group and a pyridone radical is contemplated as an oxo substituted $C_{1-10}$ heteroaryl.

The term "$C_{1-10}$ heteroaryloxy" refers to a $C_{1-10}$ heteroaryl attached through an oxygen.

The term "optionally substituted $C_{1-10}$ heteroaryloxy" refers to a $C_{1-10}$ heteroaryl optionally having 1 to 5 substituents on carbon independently selected from the group consisting of $C_{1-4}$ alkyl, $C_{1-4}$ alkoxy, cyano, halo, hydroxyl, nitro, oxo, $C_{1-8}$ sulfonyl, and trifluoromethyl and optionally having substituents on each nitrogen independently selected from the group consisting of optionally substituted $C_{1-4}$ alkyl, $C_{1-8}$ sulfonyl, and optionally substituted phenyl.

The term "optionally substituted phenyl" refers to a phenyl group optionally having 1 to 5 substituents independently selected from the group consisting of $C_{2-4}$ alkenyl, $C_{1-4}$ alkyl, $C_{1-4}$ alkoxy, $C_{1-9}$ amide, $C_{0-8}$ alkylamino, $C_{1-5}$ oxycarbonyl, cyano, halo, hydroxyl, nitro, $C_{1-8}$ sulfonyl, and trifluoromethyl.

More particularly "optionally substituted phenyl" refers to a phenyl group optionally having 1 to 5 substituents independently selected from the group consisting of $C_{1-4}$ alkyl, $C_{1-4}$ alkoxy, $C_{1-9}$ amide, $C_{0-8}$ alkylamino, $C_{1-5}$ oxycarbonyl, cyano, halo, hydroxyl, nitro, and trifluoromethyl.

The term "$C_{1-6}$ sulfonylamido" refers to a —NHS(O)$_2$—R group wherein R is $C_{1-6}$ alkyl.

The term "$C_{0-6}$ sulfonylamino" refers to a —S(O)$_2$NH—R group wherein R is selected from the group consisting of hydrogen and is $C_{1-6}$ alkyl.

The term "$C_{1-4}$ thioalkoxy" refers to a $C_{1-4}$ alkyl attached through a sulfur atom.

The term "pharmaceutically acceptable salt" refers to salts of pharmaceutically acceptable organic acids and bases or inorganic acids and bases. Such salts are well known in the art and include those described in Journal of Pharmaceutical Science, 66, 2-19 (1977). Examples are the hydrochloride and mesylate salts.

The term "substituted," including when used in "optionally substituted" refers to one or more hydrogen radicals of a group having been replaced with non-hydrogen radicals (substituent(s)). It is understood that the substituents may be either the same or different at every substituted position and may include the formation of rings. Combinations of groups and substituents envisioned by this invention are those that are stable or chemically feasible.

The term "stable" refers to compounds that are not substantially altered when subjected to conditions to allow for their production. In a non-limiting example, a stable compound or chemically feasible compound is one that is not substantially altered when kept at a temperature of 40° C. or less, in the absence of moisture or other chemically reactive conditions, for about a week.

It is understood that, where the terms defined herein mention a number of carbon atoms, that the mentioned number refers to the mentioned group and does not include any carbons that may be present in any optional substituent(s) thereon.

The skilled artisan will appreciate that certain of the compounds of the present invention exist as isomers. All mixtures of stereoisomers, in any ratio, and specific geometric isomers, enantiomers, and diastereomers of the compounds of the invention are contemplated to be within the scope of the present invention.

The skilled artisan will appreciate that certain of the compounds of the present invention exist as tautomers. All tautomeric forms the compounds of the invention are contemplated to be within the scope of the present invention.

The term "compounds of the invention" include the embodiment of formula I and the other embodiments and examples described herein.

(a) One embodiment relates to compounds of formula I wherein $R_4$ is methyl.

(b) Another embodiment relates to compounds of formula I wherein $R_4$ is trifluoromethyl (c) Another embodiment relates to compounds of formula I and embodiments (a) and (b) wherein Ar is $C_{4-14}$ aryl.

(d) Another embodiment relates to compounds of formula I and embodiments (a) and (b) wherein Ar is phenyl.

(e) Another embodiment relates to compounds of formula I and embodiments (a) and (b) wherein Ar is $C_{1-10}$ heteroaryl.

(f) Another embodiment relates to compounds of formula I and embodiments (a) and (b) wherein Ar is $C_{1-10}$ heteroaryl selected from the group consisting of furan, thiophene, imidazole, oxazole, pyrazine, pyridazine, pyridine, pyrimidine, and thiazole.

(g) Another embodiment relates to compounds of formula I and embodiments (a), (b), (c), (d), (e), and (f) wherein $G_1$ is N.

(h) Another embodiment relates to compounds of formula I and embodiments (a), (b), (c), (d), (e), and (f) wherein $G_1$ is $CR_7$.

(i) Another embodiment relates to compounds of formula I and embodiments (a), (b), (c), (d), (e), and (f) wherein $G_1$ is $CR_7$ and $R_7$ is selected from the group consisting of hydrogen, halo, $C_{0-8}$ alkylamino, $C_{1-7}$ amido, $C_{1-9}$ amide, $C_{1-5}$ carbamoyl, $C_{1-5}$ ureido, cyano, and hydroxyl.

(j) Another embodiment relates to compounds of formula I and embodiments (a), (b), (c), (d), (e), and (f) wherein $G_1$ is $CR_7$ and $R_7$ is selected from the group consisting of hydrogen, halo, cyano, and hydroxyl.

(k) Another embodiment relates to compounds of formula I and embodiments (a), (b), (c), (d), (e), (f), (g), (h), (i), and (j) wherein $G_2$ is C=O.

(l) Another embodiment relates to compounds of formula I and embodiments (a), (b), (c), (d), (e), (f), (g), (h), (i), and (j) wherein $G_2$ is $CH_2$.

(m) Another embodiment relates to compounds of formula I and embodiments (a), (b), (c), (d), (e), (f), (g), (h), (i), (j), (k), and (l) wherein $R_3$ is selected from the group consisting of optionally substituted $C_{1-6}$ alkyl, optionally substituted $C_{3-6}$ heterocycloalkyl, and optionally substituted $C_{3-8}$ cycloalkyl.

(n) Another embodiment relates to compounds of formula I and embodiments (a), (b), (c), (d), (e), (f), (g), (h), (i), (j), (k), and (l) wherein $R_3$ is $C_{1-6}$ alkyl optionally substituted with 1 to 5 substituents selected from the group consisting of halo, hydroxy, $C_{1-4}$ alkoxy, $C_{3-8}$ cycloalkyl, and $C_{3-6}$ heterocycloalkyl selected from the group consisting of piperidine, piperazine, morpholine, oxetane, tetrahydropyran, and tetrahydrofuran optionally substituted on any ring nitrogen by $C_{1-4}$ alkyl.

(o) Another embodiment relates to compounds of formula I and embodiments (a), (b), (c), (d), (e), (f), (g), (h), (i), (j), (k), and (l) wherein $R_3$ is $C_{1-6}$ alkyl.

(p) Another embodiment relates to compounds of formula I and embodiments (a), (b), (c), (d), (e), (f), (g), (h), (i), (j), (k), and (l) wherein $R_3$ is $C_{3-6}$ heterocycloalkyl selected from the group consisting of piperidine, piperazine, morpholine, oxetane, tetrahydropyran, tetrahydrothiopyran, dioxidotetrahydrothiopyran, and tetrahydrofuran and optionally substituted on any ring nitrogen by $C_{1-4}$ alkyl.

(q) Another embodiment relates to compounds of formula I and embodiments (a), (b), (c), (d), (e), (f), (g), (h), (i), (j), (k), and (l) wherein $R_3$ is $C_{3-8}$ cycloalkyl.

(r) Another embodiment relates to compounds of formula I and embodiments (a), (b), (c), (d), (e), (f), (g), (h), (i), (j), (k), and (l) wherein $R_3$ is $C_{3-8}$ cycloalkyl$C_{1-4}$ alkyl.

(s) Another embodiment relates to compounds of formula I and embodiments (a), (b), (c), (d), (e), (f), (g), (h), (i), (j), (k), (l), (m), (n), (o), (p), (q), and (r) wherein $R_2$ is hydrogen.

(t) Another embodiment relates to compounds of formula I and embodiments (a), (b), (c), (d), (e), (f), (g), (h), (i), (j), (k), (l), (m), (n), (o), (p), (q), (r), and (s) wherein $R_5$ $C_{1-6}$ alkyl and $R_6$ is hydrogen.

(u) Another embodiment relates to compounds of formula I and embodiments (a), (b), (c), (d), (e), (f), (g), (h), (i), (j), (k), (l), (m), (n), (o), (p), (q), (r), and (s) wherein $R_5$ is hydrogen and $R_6$ is $C_{1-6}$ alkyl.

(v) Another embodiment relate to compounds of formula I and embodiments (a), (b), (c), (d), (e), (f), (g), (h), (i), (j), (k), (l), (m), (n), (o), (p), (q), (r), and (s) wherein $R_5$ methyl and $R_6$ is hydrogen.

(w) Another embodiment relate to compounds of formula I and embodiments (a), (b), (c), (d), (e), (f), (g), (h), (i), (j), (k), (l), (m), (n), (o), (p), (q), (r), and (s) wherein $R_5$ is hydrogen and $R_6$ is methyl.

(x) Another embodiment relates to compounds of formula I and embodiments (a), (b), (c), (d), (e), (f), (g), (h), (i), (j), (k), (l), (m), (n), (o), (p), (q), (r), and (s) wherein $R_5$ is hydrogen and $R_6$ is hydrogen.

(y) Another embodiment relates to compounds of formula I and embodiments (a), (b), (c), (d), (e), (f), (g), (h), (i), (j), (k), (l), (m), (n), (o), (p), (q), (r), and (s) wherein $R_5$ and $R_6$ are taken together to form —$CH_2CH_2$—.

(z) Another embodiment relates to compounds of formula I and embodiments (a), (b), (c), (d), (e), (f), (g), (h), (i), (j), (k), (l), (m), (n), (o), (p), (q), (r), (s), (t), (u), (v), (w), (x), and (y) wherein $R_1$ is, each time taken, independently selected from the group consisting of halo, cyano, $C_{1-6}$ alkyl, trifluoromethyl, $C_{1-4}$ alkoxy, trifluoromethoxy, nitro, —NHC(O)NR$_8$R$_9$, —NHC(O)OR$_{10}$, and —NH(SO$_2$)NHR$_8$.

(aa) Another embodiment relates to compounds of formula I and embodiments (a), (b), (c), (d), (e), (f), (g), (h), (i), (j), (k), (l), (m), (n), (o), (p), (q), (r), (s), (t), (u), (v), (w), (x), (y), and (z) wherein m is at least 1 and at least one of $R_1$ is selected from the group consisting of —NHC(O)NR$_8$R$_9$, —NHC(O)OR$_{10}$, and —NH(SO$_2$)NHR$_8$.

(bb) Another embodiment relates to compounds of formula I and embodiments (a), (b), (c), (d), (e), (f), (g), (h), (i), (j), (k), (l), (m), (n), (o), (p), (q), (r), (s), (t), (u), (v), (w), (x), (y), and (z) wherein m is at least 1 and at least one of $R_1$ is —NHC(O)NR$_8$R$_9$ and $R_8$ is hydrogen and $R_9$ is selected from the group consisting of $C_{1-4}$ alkyl, $C_{3-8}$ cycloalkylC$_{1-4}$ alkyl, and $C_{3-8}$ cycloalkyl.

(cc) Another embodiment relates to compounds of formula I and embodiments (a), (b), (c), (d), (e), (f), (g), (h), (i), (j), (k), (l), (m), (n), (o), (p), (q), (r), (s), (t), (u), (v), (w), and (x) wherein m is at least 1 and at least one of $R_1$ is —NHC(O)NR$_8$R$_9$ and $R_8$ is hydrogen and $R_9$ is $C_{1-4}$ alkyl.

(dd) Another embodiment relates to compounds of formula I and embodiments (a), (b), (c), (d), (e), (f), (g), (h), (i), (j), (k), (l), (m), (n), (o), (p), (q), (r), (s), (t), (u), (v), (w), (x), (y), and (z) wherein m is at least 1 and at least one of $R_1$ is —NHC(O)NR$_8$R$_9$ and $R_8$ is hydrogen and $R_9$ is $C_{3-8}$ cycloalkylC$_{1-4}$ alkyl.

(ee) Another embodiment relates to compounds of formula I and embodiments (a), (b), (c), (d), (e), (f), (g), (h), (i), (j), (k), (l), (m), (n), (o), (p), (q), (r), (s), (t), (u), (v), (w), (x), (y), and (z) wherein m is at least 1 and at least one of $R_1$ is —NHC(O)NR$_8$R$_9$ and $R_8$ is hydrogen and $R_9$ is $C_{3-8}$ cycloalkyl.

(ff) Another embodiment relates to compounds of formula I and embodiments (a), (b), (c), (d), (e), (f), (g), (h), (i), (j), (k), (l), (m), (n), (o), (p), (q), (r), (s), (t), (u), (v), (w), (x), (y), and (z) wherein m is at least 1 and at least one of $R_1$ is selected from the group consisting of —NHC(O)NR$_8$R$_9$ and $R_8$ is hydrogen and $R_9$ is selected from the group consisting of methyl and ethyl.

(gg) Another embodiment relates to compounds of formula I and embodiments (a), (b), (c), (d), (e), (f), (g), (h), (i), (j), (k), (l), (m), (n), (o), (p), (q), (r), (s), (t), (u), (v), (w), (x), (y), and (z) wherein m is at least 1 and at least one of $R_1$ is selected from the group consisting of —NHC(O)NR$_8$R$_9$ and $R_8$ is hydrogen and $R_9$ is $C_{3-8}$ cycloalkylC$_{1-4}$ alkyl selected from the group consisting of methylcyclopropyl, methylcyclobutyl, and methylcyclopentyl.

(hh) Another embodiment relates to compounds of formula I and embodiments (a), (b), (c), (d), (e), (f), (g), (h), (i), (j), (k), (l), (m), (n), (o), (p), (q), (r), (s), (t), (u), (v), (w), (x), (y), and (z) wherein m is at least 1 and at least one of $R_1$ is selected from the group consisting of —NHC(O)NR$_8$R$_9$ and $R_8$ is hydrogen and $R_9$ is $C_{3-8}$ cycloalkyl selected from the group consisting of cyclopropyl, cyclobutyl, and cyclopentyl.

(ii) Another embodiment relates to compounds of formula I and embodiments (a), (b), (c), (d), (e), (f), (g), (h), (i), (j), (k), (l), (m), (n), (o), (p), (q), (r), (s), (t), (u), (v), (w), (x), (y), (z), (aa), (bb), (cc), (dd), (ee), (ff), (gg), and (hh) wherein m is 1.

The compounds of the invention can be prepared by a variety of procedures, some of which are described below. All substituents, unless otherwise indicated, are as previously defined. The products of each step can be recovered by conventional methods including extraction, evaporation, precipitation, chromatography, filtration, trituration, crystallization, and the like. The procedures may require protection of certain groups, for example hydroxy, amino, or carboxy groups to minimize unwanted reactions. The selection, use, and removal of protecting groups are well known and appreciated as standard practice, for example T. W. Greene and P. G. M. Wuts in Protective Groups in Organic Chemistry (John Wiley and Sons, 1991).

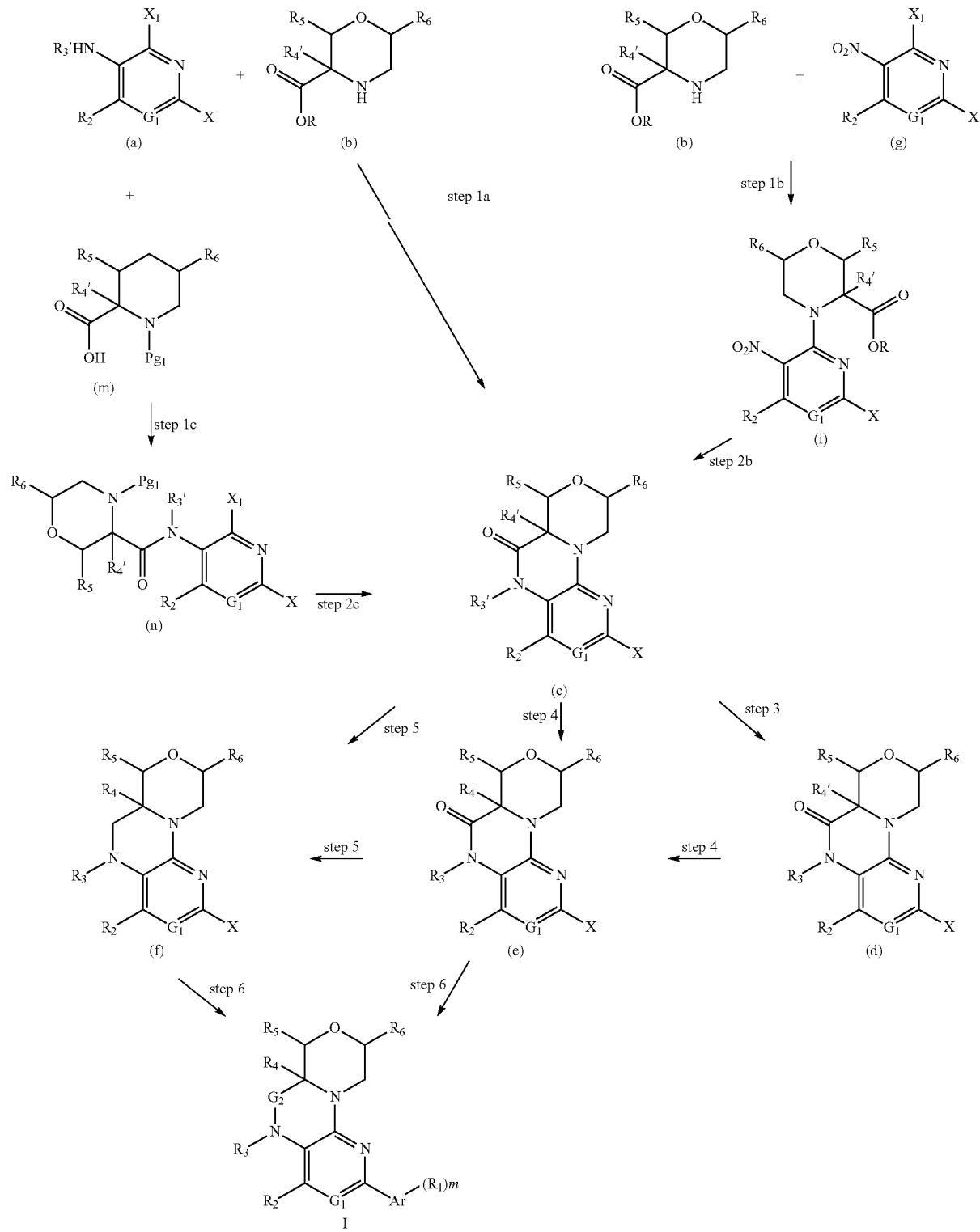

Scheme A, step 1a, depicts the reaction of an appropriate compound of formula (a) with an appropriate compound of formula (b) to give a compound of formula (c). An appropriate compound of formula (a) is one in which $G_1$ is as desired in the final compound of formula I, $R_2$ is as desired in the final compound of formula I, $R_3'$ is a protecting group or $R_3$ as desired in the final compound of formula I or gives rise to $R_3$ as desired in the final compound of formula I, and X and $X_1$ are leaving groups, including halogens, particularly as chloro and bromo. An appropriate compound of formula (b) is one in which R is hydrogen or forms and ester, such as a $C_{1-4}$ alkyl, $R_5$ and $R_6$ are as desired in the final compound of formula I, and $R_{4'}$ is hydrogen or $R_4$ as desired in the final compound of formula I.

Such reactions are well understood and appreciated. For example, such a reaction is generally carried out in a solvent, such as DMSO, THF, dimethylformamide, dimethylacetamide, and the like. The reaction is carried out with the use of a suitable base, such as alkali metal hydroxides, such as sodium hydroxide, and alkali metal alkoxides, such as sodium alkoxides and potassium alkoxides, alkali metal carbonates, such as sodium carbonate and potassium carbonate and amine bases, such diisopropylethylamine (DIPEA), triethylamine, pyridine, and the like. The reaction is typically carried out at temperatures of from 0° C. to 100° C. The reaction typically requires 1 to 72 hours.

Scheme A, step 1b, depicts the reaction of an appropriate compound of formula (g) with an appropriate compound of formula (b) to give a compound of formula (i). An appropriate compound of formula (g) is one in which $G_1$ is as desired in the final compound of formula I and X and $X_1$ are leaving groups, including halogens, particularly as chloro and bromo. An appropriate compound of formula (b) is as described in Scheme A, step 1a. Such reactions are well understood and appreciated and are carried out, for example as described above in Scheme A, step 1a.

Scheme A, step 2b, depicts the reduction of the nitro group of a compound of formula (i) and cyclization to give a compound of formula (c) in which $R_{3'}$ is hydrogen. Such reduction reactions are well known in the art. Such cyclization reactions are also well known in the art.

Scheme A, step 1c, depicts the reaction of an appropriate compound of formula (m) with an appropriate compound of formula (a) to give a compound of formula (n). An appropriate compound of formula (m) is one in which $Pg_1$ is a protecting group, $R_5$ and $R_6$ are as desired in the final compound of formula I, and $R_{4'}$ is hydrogen or $R_4$ as desired in the final compound of formula I. An appropriate compound of formula (a) is as described in Scheme A, step 1a. Such amide forming reactions are well understood and appreciated.

Scheme a, step 2c, depicts the deprotection and cyclization of a compound of formula (n) to give a compound of formula (c). The use and removal of suitable protecting groups is well known and appreciated in the art. Cyclization reactions are also well known and also described in Scheme A, step 1a. Once obtained a compound of formula (c) can be elaborated as further described in Scheme A.

Scheme A, step 3, depicts the reaction of a compound of formula (c) in which $R_3'$ is hydrogen with an appropriate alkylating reagent to give a compound of formula (d). An appropriate alkylating reagent is one of the formula $R_3$—$X_3$ where $R_3$ is as desired in the final compound of formula I and $X_3$ is a suitable leaving group, for example a halogen, particularly chloro, bromo, or iodo, or a sulfonate, for example trifluoromethanesulfonate, toslylate, or nosylate.

For example, such a reaction is generally carried out in a solvent, such as DMSO, THF, dimethylformamide, dimethylacetamide, pyridine, and the like. The reaction is carried out with the use of a suitable base, such as alkali metal alkoxides, such as sodium alkoxides, alkali metal carbonates, such as potassium carbonate, and stronger bases such as lithium diisopropylamide and lithium hexamethyldisilazide, and the like. The reaction is typically carried out at temperatures of from 0° C. to 100° C. The reaction typically requires 1 to 72 hours.

Scheme A, steps 4, depicts the reaction of a compound of formula (c) in which $R_3'$ is a protecting group and $R_{4'}$ is hydrogen or a compound of formula (d) in which $R_{4'}$ is hydrogen and $R_3$ is as desired in the final product of formula I to give a compound of formula (e). Appropriate reagents are methyl halides, such as methyl iodide, dimethyl sulfate, methyl sulfonates and trifluoromethyl transfer reagents. It is understood that compounds of formula (e) in which $R_3$ is hydrogen can be readily prepared by the method of step 3 by the use protecting groups which can be removed after step 4, 5, or 6.

For example, such reactions are generally carried out in a suitable solvent such as DMSO, DMF, THF and the like and may be carried out using a suitable base, such as alkali metal hydroxides, such as sodium hydroxide, and alkali metal alkoxides, such as sodium alkoxides, and the like. The reaction typically is carried out at temperatures of from –20° C. to 20° C. and require about 1 hour to 3 days.

Scheme A, steps 5, depicts the reduction of amides (c) in which $R_3$ is hydrogen or amides (e) to give an amine for formula (f). Such reactions are well known and can be carried out using lithium aluminum hydride, catalytic hydrogenation, and borane reagents as is well known in the art. Suitable compounds of formula (c) or (e) are those in which $R_{4'}$ is $R_4$ as desired in the final compound of formula I.

It is understood that a compound of formula (f) in which $R_3$ is hydrogen, in a step not shown, can be alkylated to give a compound of formula (f) in which $R_3$ is not hydrogen. Such alkylations can be accomplished by the use of alkylating agents or by reductive amination.

For example, alkylations of such an amine are carried out with an appropriate alkylating reagent. An appropriate alkylating reagent is one of the formula $R_3$—$X_2$ where $R_3$ is as desired in the final compound of formula I and $X_2$ is a suitable leaving group, such as a halogen, particularly chlorine, bromine or iodine, or a sulfonate, such as methanesulfonate or p-toluenesulfonate. Such reactions are generally carried out in a solvent, such as ethyl acetate, tetrahydrofuran, dimethylformamide, DMSO, or acetonitrile and with a base, such as potassium carbonate, sodium carbonate, sodium bicarbonate, triethylamine, or diisopropylethylamine. Such reactions generally are carried out at a temperature of from room temperature to the reflux temperature of the chosen solvent and typically require 1 hour to 2 days.

For reductive alkylations are carried out using a ketone or aldehyde which gives rise to $R_3$ as desired in the final compound of formula I. For example, reductive aminations are carried out under a variety of conditions using reducing agents, such as sodium borohydride, sodium triacetoxyborohydride, zinc/hydrochloric acid, zinc borohydride, and the like. When using sodium cyanoborohydride the reaction is carried out in a solvent, such as methanol, ethanol, isopropanol, and water or mixtures thereof. As is well known in the art, it may be advantageous to monitor and adjust the pH during such reactions. Typically the reaction is carried out at temperatures of from about 0° C. to about 60° C. and typically require from about 1 to about 24 hours.

Alternately, such reductive amination can be carried out by hydrogenation over a catalyst. A variety of catalysts are suitable for this purpose, including palladium, platinum, and nickel catalysts. Such hydrogenations are carried out in a suitable solvent such as ethyl acetate, ethanol, methanol, isopropanol, and the like and are carried out at pressure ranging from atmospheric to about 300 psi (2068 kPascals) and temperatures of from room temperature to about 100° C.

Scheme A, steps 6, depicts the reaction of a compound of formula (e) or (f) with an appropriate —Ar($R1$)$_m$ transfer reagent to give compound of formula I. An appropriate —Ar($R_1$)$_m$ transfer reagent is one in which Ar, $R_1$, and m are as desired in the formula I or $R_1$ give rise to a group as desired in the final compound of formula I. Such reactions are well known and include metal catalyzed carbon-carbon bond forming reactions such as the Suzuki coupling. For example, a compound of formula (e) or (f) a reacted with an appropriate borane compound, such as $(HO)_2B—Ar(R_1)_m$ to give a compound of formula I.

It will be recognized by one of ordinary skill in the art that the steps in Scheme A may be varied to provide compounds of formula I. In particular, the order of the steps required to produce the compounds of formula I is dependent upon the particular compound being synthesized, the starting compound, and the relative lability of the substituted moieties. For example, a compound of formula (a) can undergo step 6 to provide a compound of formula (a) in which X is —$Ar(Ri)_m$ which is further elaborated to give a compound of formula I or a compound of formula (n) is reduced and then cyclized to give a compound of formula (f) directly.

It is also understood that some compounds of formula I may be elaborated to other compounds of formula I, in an additional steps not shown. For example, a compound of formula I in which $R_1$ or $R_2$ is halogen, generally bromo, can undergo a variety of reactions to give compound in which $R_1$ or $R_2$ is other than halogen. Compounds of formula I may be elaborated in a variety of other ways. Such reactions include hydrolysis, oxidation, reduction, alkylation, amidations, sulfonations, alkynations, alkyenations, and the like. Also, in an optional step, not shown, the compounds of formula I can be converted to pharmaceutically acceptable salts by methods well known and appreciated in the art.

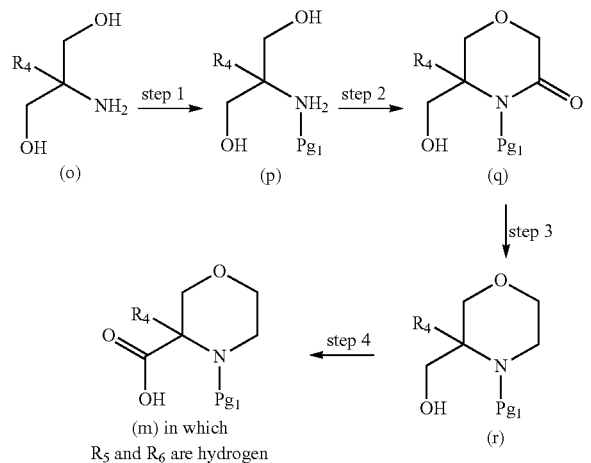

Scheme B

Scheme B, step 1, depicts the protection of an appropriate compound of formula (o) to give a compound of formula (p). An appropriate compound of formula (o) is one in which $R_4$ is as desired in the final compound of formula I. In a compound of formula (p), $Pg_1$ is a suitable protecting group, generally an amide or carbamate protecting group, including benzamine, acetamide, t-butoxycarbonyl, benzyloxycarbonyl, and the like. The use of protecting groups is well understood and appreciated.

Scheme B, step 2, depicts the reaction of a compound of formula (p) with an appropriate cyclizing reagent to give a compound of formula (q). Examples of appropriate cyclizing reagent include chloroacetyl chloride. Such cyclization reactions can be used to give a compound of formula (r) directly by using cyclization reagents such as dibromoethane to give a compound of formula (r) directly.

Cyclization reactions such as that depicted in Scheme B, step 2, can be carried out under a variety of conditions typically used for amide formation.

Scheme B, steps 3, depicts the reduction of an amide of a compound of formula (q) to give a compound of formula (r). The reduction of amides to giver amines is well known in the art. Such reactions are well known and can be carried out using lithium aluminum hydride, catalytic hydrogenation, and borane reagents as is well known in the art.

Scheme B, steps 4, depicts the oxidation of an alcohol of formula (r) to give an acid of formula (m) in which $R_5$ and $R_6$ are hydrogen. Such oxidations are well known.

EXAMPLE: 1

1-(4-(5-(cyclopropylmethyl)-6a-methyl-6-oxo-5,6, 6a,7,9,10-hexahydro-[1,4]oxazino[3,4-h]pteridin-2-yl)phenyl)-3-methylurea

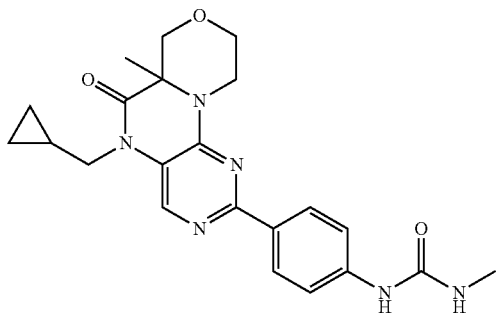

A round-bottomed flask equipped with a magnetic stirrer was added 2,4-dichloropyrimidin-5-amine (1.89 g, 11.52 mmol), DIPEA (8.05 ml, 46.1 mmol), morpholine-3-carboxylic acid (1.66 g, 12.68 mmol), and DMSO (5 ml). The reaction was stirred at 100° C. overnight. The reaction mixture was poured into water and extracted with EtOAc 3 times. The pH of the aqueous layer was adjusted (about 5) with 10% citric acid and extracted again with EtOAc. The combined organic layer dried over $MgSO_4$, filtered, and concentrated in vacuo to furnish a tan solid. The solid was triturated in diethyl ether containing a small amount of EtOH, filtered, and dried to give 2-chloro-6a,7,9,10-tetrahydro-[1,4]oxazino[3,4-h]pteridin-6(5H)-one: 1.95 g (70.3%). MS [M+H] found 241.

To a round-bottomed flask equipped with a magnetic stirrer was added 2-chloro-6a,7,9,10-tetrahydro-[1,4]oxazino[3,4-h]pteridin-6(5H)-one (800 mg, 3.32 mmol), DMSO (5 ml), sodium 2-methylpropan-2-olate (351 mg, 3.66 mmol). The reaction mixture was cooled to 0° C. and (bromomethyl) cyclopropane (0.372 ml, 3.66 mmol) was added in DMSO (1 mL). The reaction was removed from the ice-bath and stirred at 20° C. for 16 hours. The heterogeneous suspension was added to water (10 mL) to give a precipitate, which was collected by filtration, was successively washed with water, a small amount of ethanol and diethyl ether. The collected solid was dried in-vacuo to afford 2-chloro-5-(cyclopropylmethyl)-6a,7,9,10-tetrahydro-[1,4]oxazino[3,4-h]pteridin-6 (5H)-one (746 mg, 2.53 mmol, 76% yield) as a off white solid. MS [M+H] found 295.

To a round-bottomed flask equipped with a magnetic stirrer was added 2-chloro-5-(cyclopropylmethyl)-6a,7,9,10-tetrahydro-[1,4]oxazino[3,4-h]pteridin-6(5H)-one (745 mg, 2.53 mmol), DMSO (10 ml), iodomethane (0.189 ml, 3.03 mmol). The suspension was cooled to 0° C. and sodium 2-methylpropan-2-olate (292 mg, 3.03 mmol) was added. The reaction was removed from the ice-bath and stirred at 20° C. for 16 hours. The reaction solution was poured into water, extracted with ethyl acetate 3 times and the organic layer washed with saturated NaCl. The organic layer was collected, dried with $Na_2SO_4$, filtered and the filtrate concentrated in vacuo to furnish a light-brown solid. The solid was washed with a small amount of ethanol followed by diethyl ether to afford 2-chloro-5-(cyclopropylmethyl)-6a-methyl-6a,7,9,10-tetrahydro-[1,4]oxazino[3,4-h]pteridin-6(5H)-one (641 mg, 2.228 mmol, 82% yield) as white solid. MS [M+H] found 309.

To a microwave vial equipped with a magnetic stirrer was added 2-chloro-5-(cyclopropylmethyl)-6a-methyl-6a,7,9,10-tetrahydro-[1,4]oxazino[3,4-h]pteridin-6(5H)-one (88 mg, 0.285 mmol), 1,4-dioxane (2 ml), 1-methyl-3-(4-(4,4,5,5-tetramethyl-1,3,2-dioxaborolan-2-yl)phenyl)urea (118 mg, 0.428 mmol), $NaHCO_3$ (saturated, 0.491 mL), and $PdCl_2$(dppf) (209 mg, 0.285 mmol). The reaction was irradiated in the microwave at 100° C. for 40 min. The reaction solution was then poured into water, extracted with ethyl acetate three times and the combined organic layers were washed with water and then brine, then dried with $Na_2SO_4$, filtered, and the filtrate concentrated in-vacuo to give a brown residue. The aqueous layer was acidified with AcOH (pH about 5) and concentrated in-vacuo to give a grey residue. The combined residues were purified via preparative LC/MS (45-50% gradient of 10 mmol $NH_4HCO_3$ in 20/80(v/v) water/acetonitrile in 10 mmol $NH_4HCO_3$ in water, Phenomenex Gemini 5 μm C18, 75×30 mm column to give the title compound (54 mg, 0.128 mmol, 44.8% yield) as a white solid. $^1$H NMR (400 MHz, DMSO-$d_6$) δ ppm 0.25-0.57 (m, 4H) 1.18 (m, 1H) 1.35 (s, 3H) 2.62-2.71 (m, 3H) 3.17-3.26 (m, 1H) 3.54-3.65 (m, 1H) 3.68 (d, J=11.62 Hz, 1H) 3.81 (dd, J=14.53, 6.95 Hz, 1H) 3.89-4.02 (m, 2H) 4.07 (dd, J=11.62, 3.54 Hz, 1H) 4.20 (dd, J=13.77, 2.40 Hz, 1H) 6.07 (d, J=4.80 Hz, 1H) 7.49 (d, J=8.84 Hz, 2H) 8.19 (d, J=8.84 Hz, 2 H) 8.36 (s, 1H) 8.72 (s, 1H). MS [M+H] found 423.

EXAMPLE: 2

1-(4-(5-(cyclopropylmethyl)-6a-methyl-6-oxo-5,6,6a,7,9,10-hexahydro-[1,4]oxazino[3,4-h]pteridin-2-yl)phenyl)-3-methylurea TFA salt

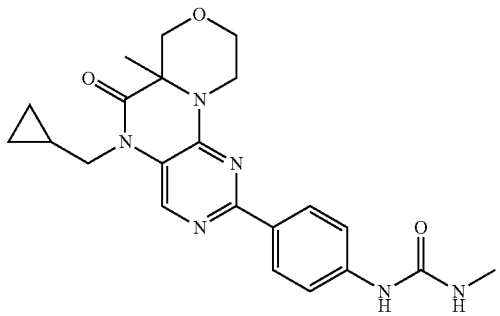

To a microwave vial equipped with a magnetic stirrer was added crude 2-chloro-5-(cyclopropylmethyl)-6a-methyl-6a,7,9,10-tetrahydro-[1,4]oxazino[3,4-h]pteridin-6(5H)-one (140 mg, 0.453 mmol), DMA (2 ml), 1-methyl-3-(4-(4,4,5,5-tetramethyl-1,3,2-dioxaborolan-2-yl)phenyl)urea (188 mg, 0.680 mmol), $Na_2CO_3$ (0.907 ml, 1.814 mmol, 2M), and $PdCl_2$(dppf) (16.59 mg, 0.023 mmol). The reaction was irradiated in the microwave at 110° C. for 70 min. The reaction solution was poured into water, extracted with ethyl acetate 3 times and the organic layers washed with saturated NaCl, dried with $Na_2SO_4$, filtered, and concentrated in-vacuo to give a residue. The residue was purified via preparative LC/MS eluted with 25% of acetonitrile (containing 0.035% TFA) in water (containing 0.05% TFA) on a Phenomenex Gemini 5 μm C18, 75×30 mm column) to give the title compound (6 mg, 0.014 mmol, 3.13% yield) as a tan solid. $^1$H NMR (400 MHz, DMSO-$d_6$) δ ppm 0.22-0.58 (m, 4H) 1.16 (d, J=6.82 Hz, 1H) 1.35 (s, 3H) 2.62-2.71 (m, 3H) 3.19-3.34 (m, 1H) 3.54-3.65 (m, 1H) 3.69 (d, J=11.62 Hz, 1H) 3.81 (dd, J=14.65, 7.07 Hz, 1H) 3.89-4.04 (m, 2H) 4.07 (dd, J=11.37, 4.04 Hz, 1H) 4.14 (dd, J=5.68, 3.41 Hz, 1H) 6.11 (d, J=4.29 Hz, 1H) 7.51 (d, J=8.84 Hz, 2H) 8.19 (d, J=8.84 Hz, 2H) 8.35 (s, 1H) 8.80 (s, 1H). MS [M+H] found 423.

EXAMPLE: 3

(R)-1-(4-(5-(cyclopropylmethyl)-6a-methyl-6-oxo-5,6,6a,7,9,10-hexahydro-[1,4]oxazino[3,4-h]pteridin-2-yl)phenyl)-3-methylurea and

EXAMPLE: 4

(S)-1-(4-(5-(cyclopropylmethyl)-6a-methyl-6-oxo-5,6,6a,7,9,10-hexahydro-[1,4]oxazino[3,4-h]pteridin-2-yl)phenyl)-3-methylurea

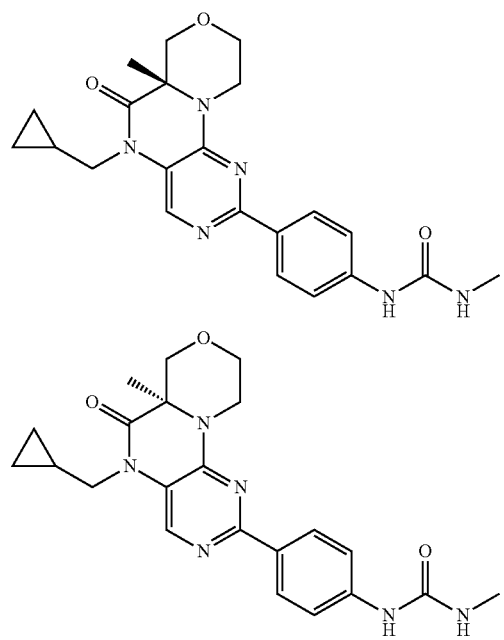

The product of Example 1 (20 mg) was separated by HPLC (Chiralpak AD-H column, flowrate=1.25 mL/min, eluting with 30% isopropanol in 10 mM aqueous $NH_4OAc$ to give Isomer 1 (2 mg, t=1.33 min) and Isomer 2 (2 mg, t=3.48 min)

EXAMPLE: 5

1-(4-(5-(cyclopropylmethyl)-6a-methyl-6-oxo-5,6, 6a,7,9,10-hexahydro-[1,4]oxazino[3,4-h]pteridin-2-yl)phenyl)-3-ethylurea, TFA salt

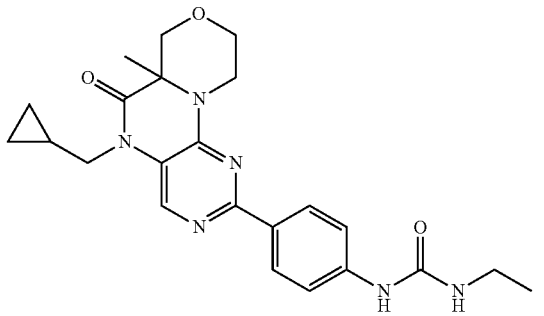

The title compound was prepared by method similar to Example 1, except the title compound was purified preparative HPLC eluting with a gradient of 25-30% acetonitrile (containing 0.035% TFA) in water (containing 0.05% TFA) using a Sunfire Prep 5 μm C18, 75×30 mm column to afford (12 mg, 8.49%) of a pale yellow solid. $^1$H NMR (400 MHz, METHANOL-$d_4$) δ ppm 0.40-0.52 (m, 2H) 0.54-0.65 (m, 2H) 1.17 (t, J=7.2 Hz, 3H) 1.20-1.27 (m, 1H) 1.71 (s, 3H) 3.26 (q, J=7.2 Hz, 2H) 3.50-3.62 (m, 1H) 3.64-3.72 (m, 1H) 3.78-3.89 (m, 2H) 3.99 (dd, J=14.9, 7.1 Hz, 1H) 4.11-4.20 (m, 2H) 4.66-4.77 (m, 1H) 7.63 (d, J=9.1 Hz, 2H) 8.04 (s, 1H) 8.12 (d, J=8.8 Hz, 2H). MS [M+H] found 437.

EXAMPLE: 6

1-cyclopropyl-3-(4-(5-(cyclopropylmethyl)-6a-methyl-6-oxo-5,6,6a,7,9,10-hexahydro-[1,4]oxazino[3,4-h]pteridin-2-yl)phenyl)urea, TFA salt

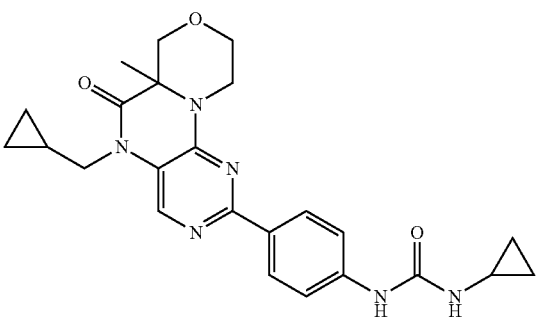

The title compound was prepared by method similar to Example 1, except the title compound was purified by preparative HPLC eluting with 25-30% acetonitrile (containing 0.035% TFA) in water (containing 0.05% TFA) using a Sunfire Prep 5 μm C18, 75×30 mm column to afford (14 mg, 8.7%) as a pale yellow solid: $^1$H NMR (400 MHz, DMSO-$d_6$) δ ppm 0.27-0.55 (m, 6H) 0.58-0.70 (m, 2H) 1.18 (d, J=5.05 Hz, 1H) 1.40 (s, 3H) 2.56 (d, J=6.82 Hz, 1H) 3.30 (d, J=3.54 Hz, 1H) 3.61 (d, J=2.27 Hz, 1H) 3.70 (d, J=11.37 Hz, 1H) 3.84 (d, J=7.07 Hz, 1H) 3.89-4.12 (m, 3H) 4.20-4.35 (m, 1H) 6.53 (br. s., 1H) 7.53 (d, J=8.59 Hz, 2 H) 8.19 (d, J=8.59 Hz, 2H) 8.33 (s, 1H) 8.63 (s, 1H). MS [M+H] found 449.

EXAMPLE: 7

(S)-1-(4-(5-(cyclopropylmethyl)-6a-methyl-6-oxo-5, 6,6a,7,9,10-hexahydro-[1,4]oxazino[3,4-h]pteridin-2-yl)phenyl)-3-ethylurea and

EXAMPLE: 8

(R)-1-(4-(5-(cyclopropylmethyl)-6a-methyl-6-oxo-5, 6,6a,7,9,10-hexahydro-[1,4]oxazino[3,4-h]pteridin-2-yl)phenyl)-3-ethylurea

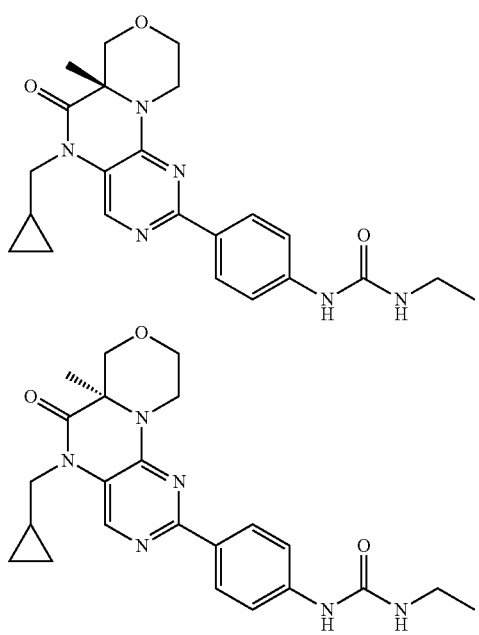

The racemate of the title compound was prepared by method similar to Example 1. The racemate of the title compound was purified by preparative HPLC (eluting with a gradient of 25-25% ACN (containing 0.035% TFA) in water (containing 0.05% TFA) using a Sunfire Prep 5 μm C18, 75×30 mm column). The racemate was then chirally separated on ChiralPak AD-H (5 μm, 20×250 mm, 40% of MeOH: nPrOH (2:1) in liquid $CO_2$) to give the title compounds. Isomer 1 had a retention time of 0.95 minutes on ChiralPak AD-H column (5 μm, 2.1×150 mm, 40% of EtOH (containing 10 mM NH$_4$OAc) in liquid $CO_2$). $^1$H NMR (400 MHz, METHANOL-$d_6$) δ ppm 0.42 (m, 2H) 0.55 (m, 2H) 1.17 (t, J=8 Hz, 3H) 1.21 (m, 1H) 1.46 (s, 3H) 3.24 (quartet, J=8 Hz, 2H) 3.36 (m, 1H) 3.67 (dt, J=12, 4 Hz 1H) 3.74 (d, J=12 Hz, 1H) 3.84 (dd, J=12, 8 Hz, 1H) 3.98 (dd, J=12, 8 Hz, 1H) 4.10 (d, J=12 Hz, 1H) 4.13 (m, 1H) 4.30 (dd, J=12, 4 Hz, 1H) 7.46 (d, J=8 Hz, 2H) 8.21 (d, J=8 Hz, 2H) 8.21 (s, 1H). MS [M+H] found 437.4. Isomer 2 had a retention time of 2.21 minutes on ChiralPak AD-H column (5 μm, 2.1×150 mm, 40% of EtOH (containing 10 mM NH$_4$OAc) in liquid $CO_2$). $^1$H NMR (400 MHz, METHANOL-$d_6$) δ ppm 0.42 (m, 2H) 0.55 (m, 2H) 1.17 (t, J=8 Hz, 3H) 1.21 (m, 1H) 1.46 (s, 3H) 3.24 (quartet, J=8 Hz, 2H) 3.36 (m, 1H) 3.67 (dt, J=12, 4 Hz 1H) 3.74 (d, J=12 Hz, 1H) 3.84 (dd, J=12, 8 Hz, 1H) 3.98 (dd, J=12, 8 Hz, 1H) 4.10 (d, J=12 Hz, 1H) 4.13 (m, 1H) 4.30 (dd, J=12, 4 Hz, 1H) 7.46 (d, J=8 Hz, 2H) 8.21 (d, J=8 Hz, 2H) 8.21 (s, 1H). MS [M+H] found 437.4.

EXAMPLE: 9

(S)-1-cyclopropyl-3-(4-(5-(cyclopropylmethyl)-6a-methyl-6-oxo-5,6,6a,7,9,10-hexahydro-[1,4]oxazino[3,4-h]pteridin-2-yl)phenyl)urea and

EXAMPLE: 10

(R)-1-cyclopropyl-3-(4-(5-(cyclopropylmethyl)-6a-methyl-6-oxo-5,6,6a,7,9,10-hexahydro-[1,4]oxazino[3,4-h]pteridin-2-yl)phenyl)urea

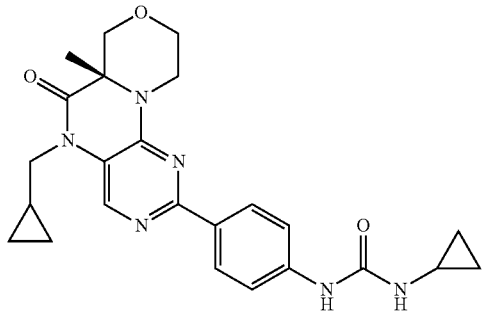

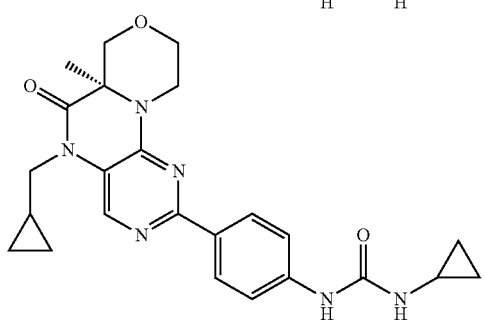

To a mixture of 2-chloro-6a,7,9,10-tetrahydro-[1,4]oxazino[3,4-h]pteridin-6(5H)-one (3 g, 12.47 mmol) in DMSO (10 mL) cooled in an ice water bath was added sodium tert-butoxide (1.32 g, 13.7 mmol). After 15 minutes stirring, the mixture was allowed to warm up to room temperature and stirred for 45 minutes. Then (bromomethyl)cyclopropane (1.27 mL, 13 mmol) was added dropwise in 12 minutes and the resulting mixture stirred at room temperature for 15 hours. Water was added and the resulting yellow precipitate was collected by vacuum filtration and washed repeatedly with water. The solid was subjected to vacuum for 4 hours to give 2-chloro-5-(cyclopropylmethyl)-6a,7,9,10-tetrahydro-[1,4]oxazino[3,4-h]pteridin-6(5H)-one as a yellow solid (3.57 g, 97%). MS [M+H] found 295.2.

To 2-chloro-5-(cyclopropylmethyl)-6a,7,9,10-tetrahydro-[1,4]oxazino[3,4-h]pteridin-6(5H)-one (3.57 g, 12.11 mmol) in DMSO (28 mL) was added iodomethane (0.907 mL, 14.54 mmol), and the mixture was cooled in an ice-water bath. Then sodium tert-butoxide (1.39 g, 14.54 mmol) was added. After 5 minutes stirring at 0° C., the mixture was allowed to warm up to room temperature and stirred for 17 hours. The reaction mixture was cooled in an ice-water bath and more iodomethane (0.378 mL) was added, followed by more sodium tert-butoxide (582 mg). The mixture was warmed up to room temperature and stirred for 55 minutes, then sealed and heated at 50° C. (bath temperature) for 1 hour. The reaction was cooled to room temperature and additional iodomethane (3 mL) was added, then sealed and heated at 50° C. (bath temperature) for another 27 minutes then cooled in an ice-water bath and more sodium tert-butoxide (582 mg) was added. The mixture was then warmed up to room temperature and stirred for 75 minutes. The reaction mixture was then diluted with water and extracted with EtOAc. The organic layers were combined and solvent was removed to give a brown solid. The solid was dissolved in dichloromethane and purified on silica gel eluting with Hexanes-EtOAc (0-50%), to give 2-chloro-5-(cyclopropylmethyl)-6a-methyl-6a,7,9,10-tetrahydro-[1,4]oxazino[3,4-h]pteridin-6(5H)-one as a solid (773 mg, 33%). MS [M+H] found 309.2.

To 2-chloro-5-(cyclopropylmethyl)-6a-methyl-6a,7,9,10-tetrahydro-[1,4]oxazino[3,4-h]pteridin-6(5H)-one (773 mg, 2.5 mmol) was added 1-cyclopropyl-3-(4-(4,4,5,5-tetramethyl-1,3,2-dioxaborolan-2-yl)phenyl)urea (0.908 g, 3.0 mmol), Pd(dppf)Cl$_2$-dichloromethane, 1,4-dioxane (10 mL) and NaHCO$_3$ (sat., 5 mL) and the mixture was heated under an air balloon (1 atm) at 100° C. (bath temperature) for 35 minutes and then at 110° C. for 1 hour and 22 minutes. Most of the solvent was evaporated on the rotary evaporator to give a residue. The residue was diluted with MeOH and filtered through a microfilter. The solid collected was rinsed repeatedly with MeOH to give the racemic product as a light grayish solid (600 mg, desired product). The clear filtrate was purified by HPLC (25-30% of AcCN [containing 0.035% TFA] in water [containing 0.05% TFA], Phenomenex Gemini 5 μm C18, 75×30 mm column) to give an additional batch of the racemic product as a white solid (200 mg). Chiral separation was performed on ChiralPak AD-H column (5 μm, 20×150 mm, 45% of MeOH-PrOH [2:1] in liquid CO$_2$) to give (S)-1-cyclopropyl-3-(4-(5-(cyclopropylmethyl)-6a-methyl-6-oxo-5,6,6a,7,9,10-hexahydro-[1,4]oxazino[3,4-h]pteridin-2-yl)phenyl)urea as a white solid (225 mg, 20%). The title compound had a retention time of 1.43 minutes on ChiralPak AD-H column (5 μm, 2.1×150 mm, 40% of i-PrOH (containing 10 mM NH$_4$OAc) in liquid CO$_2$). $^1$H NMR (400 MHz, METHANOL-d$_6$) δ ppm 0.44 (m, 2H) 0.53 (m, 4H) 0.75 (m, 2H) 1.22 (m, 1H) 1.47 (s, 3H) 2.60 (m, 1H) 3.38 (m, 1H) 3.67 (dt, J=12, 4 Hz, 1H) 3.75 (d, J=12 Hz, 1H) 3.84 (dd, J=12, 8 Hz, 1H) 3.98 (dd, J=12, 8 Hz, 1H) 4.10 (d, J=8 Hz, 1H) 4.13 (m, 1H) 4.32 (dd, J=12, 4 Hz, 1 H) 7.49 (d, J=8 Hz, 2H) 8.21 (s, 1H) 8.21 (d, J=8 Hz, 2H). MS [M+H] found 449.4.

EXAMPLE: 11

1-methyl-3-(4-(6a-methyl-5-((1-methyl-1H-pyrazol-3-yl)methyl)-6-oxo-5,6,6a,7,9,10-hexahydro-[1,4]oxazino[3,4-h]pteridin-2-yl)phenyl)urea

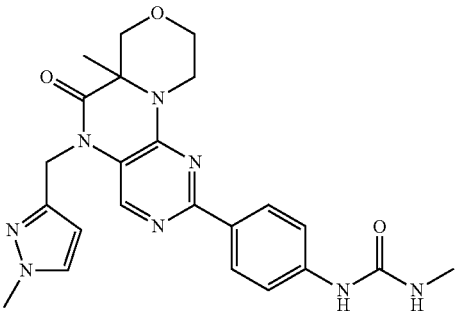

To a mixture of 2-chloro-6a,7,9,10-tetrahydro-[1,4]oxazino[3,4-h]pteridin-6(5H)-one (100 mg, 0.416 mmol), K$_2$CO$_3$ (115 mg, 0.831 mmol) in DMF (2 mL) at 0° C., was added 3-(chloromethyl)-1-methyl-1H-pyrazole (54.3 mg, 0.416 mmol). The mixture was stirred at 0° C. for 30 minutes and then at room temperature for overnight. Water was added and the mixture was extracted with EtOAc (2×). The aqueous layer was basified and then extracted with EtOAc. The combined organic layers were dried over MgSO$_4$, filtered and evaporated in vacuo to give 2-chloro-5-((1-methyl-1H-pyrazol-3-yl)methyl)-6a,7,9,10-tetrahydro-[1,4]oxazino[3,4-h]pteridin-6(5H)-one (104 mg) which was used in the next step without further purification. MS [M+H] Found 335

2-Chloro-5-((1-methyl-1H-pyrazol-3-yl)methyl)-6a,7,9,10-tetrahydro-[1,4]oxazino[3,4-h]pteridin-6(5H)-one (100 mg, 0.299 mmol) and iodomethane (0.037 mL, 0.597 mmol) were mixed in DMSO (2 mL) in a sealed scintillation vial. The mixture was frozen then sodium 2-methylpropan-2-olate (57.4 mg, 0.597 mmol) was added and covered with a layer of DMSO. The mixture was refrozen then allowed to warm to room temperature and stirred overnight. An additional 1 eq of iodomethane was added. After 1 hour the reaction was diluted with water and extracted into EtOAc. The organic layer was dried over magnesium sulfate, filtered, and evaporated in vacuo to give 2-chloro-6a-methyl-5-((1-methyl-1H-pyrazol-3-yl)methyl)-6a,7,9,10-tetrahydro-[1,4]oxazino[3,4-h]pteridin-6(5H)-one as a yellow oil, which was used without further purification. MS [M+H] Found 349

A mixture of 2-chloro-6a-methyl-5-((1-methyl-1H-pyrazol-3-yl)methyl)-6a,7,9,10-tetrahydro-[1,4]oxazino[3,4-h]pteridin-6(5H)-one (118 mg), PdCl$_2$(dppf) (43.6 mg), 1-methyl-3-(4-(4,4,5,5-tetramethyl-1,3,2-dioxaborolan-2-yl)phenyl)urea (124 mg, 0.447 mmol), saturated sodium bicarbonate solution (1.5 mL), and 1,4-dioxane (3 mL) was heated by microwave irradiation at 100° C. for 45 minutes. The reaction mixture was diluted with 2 mL of methanol, filtered then purified by mass-triggered preparative HPLC eluted with 20-30% of ACN (containing 0.035% TFA) in water (containing 0.05% TFA) on a Phenomenex Gemini 5 μm C18, 75×30 mm column to give the title compound (36 mg) as a pale yellow solid. $^1$H NMR (400 MHz, METHANOL-d$_4$) δ ppm 1.72 (s, 3H) 2.80 (s, 3H) 3.57 (m, 1H) 3.70 (m, 1H) 3.85 (s, 3 H) 3.89 (d, J=12 Hz, 1H) 4.15 (dd, J=12, 4 Hz, 1H) 4.19 (d, J=12 Hz, 1H) 4.71 (m, 1H) 4.95 (d, J=12 Hz, 1H) 5.30 (d, J=12 Hz, 1H) 6.24 (d, J=4 Hz, 1H) 7.55 (d, J=4 Hz, 1H) 7.63 (d, J=8 Hz, 2H) 8.07 (d, J=8 Hz, 2H) 8.12 (s, 1H). MS [M+H] Found 463.

EXAMPLE: 12

1-methyl-3-(4-(6a-methyl-5-((3-methyloxetan-3-yl)methyl)-6-oxo-5,6,6a,7,9,10-hexahydro-[1,4]oxazino[3,4-h]pteridin-2-yl)phenyl)urea

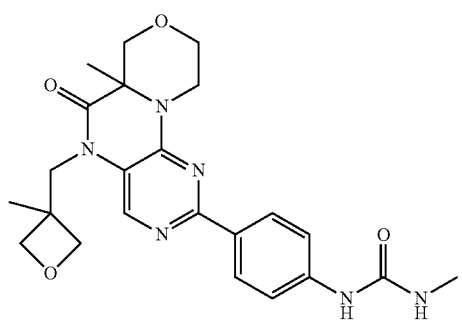

The title compound was prepared by method similar to Example 1 using 3 3-(bromomethyl)-3-methyloxetane as reactant in the alkylation and was purified by HPLC using mass-triggered preparative HPLC (eluted with 25-30% of ACN (containing 0.035% TFA) in water (containing 0.05% TFA) on a Phenomenex Gemini 5 μm C18, 75×30 mm column). The title compound was taken to the next step without isolation.

EXAMPLE: 13

1-(4-(5-(3-hydroxy-2-(hydroxymethyl)-2-methylpropyl)-6a-methyl-6-oxo-5,6,6a,7,9,10-hexahydro-[1,4]oxazino[3,4-h]pteridin-2-yl)phenyl)-3-methylurea

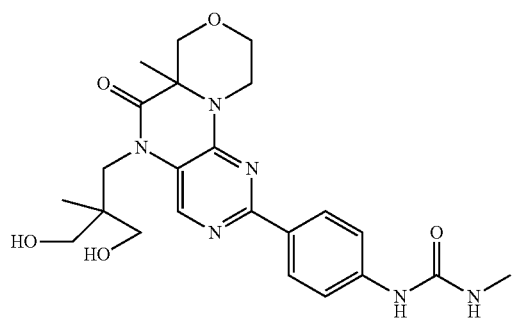

The product of Example 12 was purified by HPLC using mass-triggered preparative HPLC (eluted with 25-30% of ACN (containing 0.035% TFA) in water (containing 0.05% TFA) on a Phenomenex Gemini 5 μm C18, 75×30 mm column). Oxetane containing fractions were collected and the solvent reduced and were repurified by HPLC under the same conditions. Fractions containing the title compound were evaporated in vacuo to give a residue which was dissolved in methanol for transfer then the solvent removed under a stream of nitrogen to give the title compound (39 mg). $^1$H NMR (400 MHz, METHANOL-d$_4$) δ ppm 0.92 (s, 3H) 1.73 (s, 3H) 2.80 (s, 3H) 3.38-3.4 (m, 4H) 3.57 (m, 1H) 3.69 (m, 1H) 3.83 (m 2H) 4.13-4.18 (m, 3 H) 4.74 (m, 1H) 7.64 (d, J=8 Hz, 2H) 8.10 (d, J=8 Hz, 2H) 8.63 (s, 1H). MS [M+H] Found 471.5.

EXAMPLE: 14

1-(4-(5,6a-dimethyl-4-morpholino-6-oxo-5,6,6a,7,9,10-hexahydro-[1,4]oxazino[3,4-h]pteridin-2-yl)phenyl)-3-methylurea

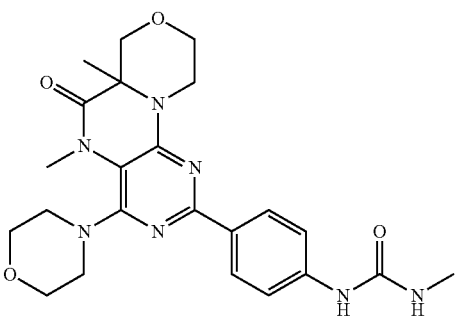

2,4,6-Trichloro-5-nitropyrimidine (1 g, 4.38 mmol) was suspended in EtOH (10 mL). Raney-Nickel®2800 in water (1.285 g, 21.89 mmol) was added and the vessel was purged with hydrogen gas and stirred at atmospheric pressure and room temperature overnight. After filtration through Celite® the filtrate was evaporated to give 1.3 g of crude 2,4,6-trichloropyrimidin-5-amine. MS [M+H] Found 200.

A round-bottom flask was charged with 2,4,6-trichloropyrimidin-5-amine (982 mg, 4.95 mmol), morpholine-3-carboxylic acid (649 mg, 4.95 mmol) and triethylamine (2.78 mL, 19.79 mmol) in ethanol (20 mL). The mixture was heated at 75° C. for 3 days then diluted with water and extracted with EtOAc. The organic layer was dried over magnesium sulfate, filtered and dried in vacuo to give 500 mg of crude 2,4-dichloro-6a,7,9,10-tetrahydro-[1,4]oxazino[3,4-h]pteridin-6(5H)-one which was used without further purification. MS [M+H] Found 275.

2,4-Dichloro-6a,7,9,10-tetrahydro-[1,4]oxazino[3,4-h]pteridin-6(5H)-one (500 mg, 1.818 mmol) and iodomethane (1.134 mL, 18.18 mmol) were mixed in DMSO (3 mL). 2-Methylpropan-2-olate (699 mg, 7.27 mmol) was added and the suspension was stirred overnight at room temperature. Ten more equivalents of iodomethane were added and the solution was heated at 50° C. for about 18 hours. The reaction was purified by mass-triggered preparative HPLC 20-60% of ACN (containing 0.035% TFA) in water (containing 0.05% TFA) on a Phenomenex Gemini 5 µm C18, 75×30 mm column)) to give 20 mg of 2,4-dichloro-5-methyl-6a,7,9,10-tetrahydro-[1,4]oxazino[3,4-h]pteridin-6(5H)-one as a tan solid. MS [M+H] Found 289.

2,4-Dichloro-5-methyl-6a,7,9,10-tetrahydro-[1,4]oxazino[3,4-h]pteridin-6(5H)-one (20 mg, 0.069 mmol) and iodomethane (9.82 mg, 0.069 mmol) were stirred in DMSO (2 mL). The mixture was frozen then 2-methylpropan-2-olate (19.94 mg, 0.208 mmol) was added as a solid followed by a layer of DMSO. The mixture was refrozen then allowed to warm up to room temperature and stirred for 1 hour. The reaction was diluted with water and extracted twice with EtOAc, the organic layers combined, dried over magnesium sulfate, filtered and evaporated in vacuo to give 20 mg (95%) of 2,4-dichloro-5,6a-dimethyl-6a,7,9,10-tetrahydro-[1,4]oxazino[3,4-h]pteridin-6(5H)-one as a white solid. MS [M+H] Found 303.

2,4-Dichloro-5,6a-dimethyl-6a,7,9,10-tetrahydro-[1,4]oxazino[3,4-h]pteridin-6(5H)-one (20 mg, 0.066 mmol), triethylamine (18.44 µL, 0.132 mmol) and morpholine (5.75 µL, 0.066 mmol) were mixed in dichloromethane at room temperature and stirred over the weekend at 50° C. The solvent was removed in vacuo to give crude 2-chloro-5,6a-dimethyl-4-morpholino-6a,7,9,10-tetrahydro-[1,4]oxazino[3,4-h]pteridin-6(5H)-one. MS [M+H] Found 354.

2-Chloro-5,6a-dimethyl-4-morpholino-6a,7,9,10-tetrahydro-[1,4]oxazino[3,4-h]pteridin-6(5H)-one (23 mg, 0.065 mmol), 1-methyl-3-(4-(4,4,5,5-tetramethyl-1,3,2-dioxaborolan-2-yl)phenyl)urea (21.54 mg, 0.078 mmol), PdCl$_2$(dppf) (9.51 mg, 0.013 mmol) and sodium bicarbonate (1.5 mL, sat.) were mixed in 1,4-dioxane (3 mL). The suspension was heated by microwave irradiation at 100° C. for 30 minutes. After filtration, the solution was purified by mass-triggered preparative HPLC eluted with 20-25% of ACN (containing 0.035% TFA) in water (containing 0.05% TFA) on a Phenomenex Gemini 5 µm C18, 75×30 mm column) to give the title compound (5.3 mg 17% yield) as a pale yellow solid. $^1$H NMR (400 MHz, MeOD) δ ppm 1.57 (s, 3H) 2.70 (s, 3H) 2.80 (s, 3H) 3.34 (m, 1H) 3.64 (m, 1H) 3.72-3.86 (m, 9H) 4.10 (m, 2H) 4.25 (m, 1H) 7.51 (d, J=8 Hz, 2H) 7.62 (d, J=8 Hz, 2H). MS [M+H] Found 468.

EXAMPLE: 15

1-(4-(5-isopropyl-6a-methyl-6-oxo-5,6,6a,7,9,10-hexahydro-[1,4]oxazino[3,4-h]pteridin-2-yl)phenyl)-3-methylurea

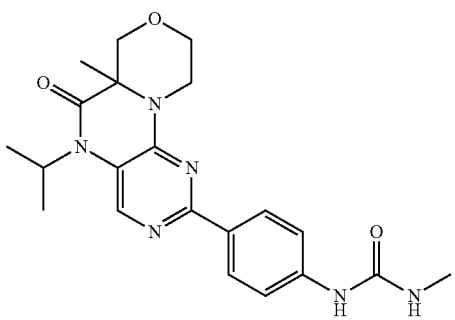

In a 100 mL flask containing 2,4-dichloropyrimidin-5-amine (1.0 g, 6.10 mmol) in 16.5 mL of dichloromethane was added acetone (1.062 g, 18.29 mmol). The solution was cooled to 0° C. then a solution of titanium tetrachloride (0.740 mL, 6.71 mmol) in 10 mL of dichloromethane was added slowly. The mixture was stirred at room temperature for 2 hours. Sodium cyanoborohydride (1.150 g, 18.29 mmol) was added in 4 equal portions over 10 minutes and the reaction was stirred at room temperature for 2 hours. The reaction was quenched with water (150 mL) and extracted with t-BuOMe twice. The organic layers were combined, dried with Na$_2$SO$_4$, filtered and concentrated in vacuo. The residue was dissolved in methanol and adsorbed onto silica. The residue was purified on silica gel using 0-10% methanol in dichloromethane as eluent. Relevant fractions were evaporated in vacuo to give 940 mg (74%) of 2,4-dichloro-N-isopropylpyrimidin-5-amine as a pale yellow oil. MS [M+H] Found 206.

A round-bottom flask was charged with 2,4-dichloro-N-isopropylpyrimidin-5-amine (940 mg, 4.56 mmol), morpholine-3-carboxylic acid hydrochloride (994 mg, 5.93 mmol), DIPEA (3.19 mL, 18.25 mmol) and DMSO (8 mL). The flask was heated overnight at 100° C. The solution was diluted with water and refrigerated for 2 hours. The aqueous solution was extracted twice with EtOAc. The organic layers were combined, dried over magnesium sulfate, filtered, and evaporated in vacuo to give 2-chloro-5-isopropyl-6a,7,9,10-tetrahydro-[1,4]oxazino[3,4-h]pteridin-6(5H)-one as a brown solid (1.2 g). MS [M+H] Found 283.

2-Chloro-5-isopropyl-6a,7,9,10-tetrahydro-[1,4]oxazino[3,4-h]pteridin-6(5H)-one (1.20 g, 4.24 mmol) and iodomethane (1.324 mL, 21.22 mmol) were mixed in DMSO. The mixture was frozen, 2-methylpropan-2-olate (1.224 g, 12.73 mmol) was added, covered by a layer of DMSO and refrozen. The mixture was allowed to room temperature and stirred overnight. Another 1 eq of 2-methylpropan-2-olate and iodomethane was added and the mixture stirred overnight at 30° C. The solution was diluted with water and extracted with EtOAc twice. The organic layers were combined, dried over magnesium sulfate, filtered, and evaporated in vacuo. The residue was absorbed onto silica and purified by column chromatography using 10-60% EtOAc in hexanes then 5% methanol in dichloromethane as eluent. Relevant fractions were evaporated in vacuo to give 98 mg (8%) 2-chloro-5-isopropyl-6a-methyl-6a,7,9,10-tetrahydro-[1,4]oxazino[3,4-h]pteridin-6(5H)-one. MS [M+H] Found 297.

2-Chloro-5-isopropyl-6a-methyl-6a,7,9,10-tetrahydro-[1,4]oxazino[3,4-h]pteridin-6(5H)-one (98 mg, 0.330 mmol) was mixed with PdCl$_2$(dppf) (48.3 mg), 1-methyl-3-(4-(4,4,5,5-tetramethyl-1,3,2-dioxaborolan-2-yl)phenyl)urea (100 mg, 0.363 mmol) and saturated sodium bicarbonate solution (2 mL, sat.) in 1,4-dioxane (4 mL). The suspension was heated by microwave irradiation at 100° C. for 30 minutes. The suspension was filtered, the solids washed with methanol then DMSO and the filtrate evaporated in vacuo. The resulting solid was purified by mass triggered preparative HPLC eluted with 20-35% of ACN (containing 0.035% TFA) in water (containing 0.05% TFA) on a Phenomenex Gemini 5 μm C18, 75×30 mm column) to give the title compound (30 mg 22% yield) as a pale yellow solid. $^1$H NMR (400 MHz, METHANOL-d$_4$) δ ppm 1.55 (m, 6H) 1.62 (s, 3H) 2.80 (s, 3H) 3.50 (td, J=12, 4 Hz, 1H) 3.68 (td, J=12, 4 Hz, 1H) 3.79 (d, J=12 Hz, 1H) 4.14 (m, 1H) 4.62 (dd, J=12, 4 Hz, 1H) 4.66 (m, 1 H) 7.62 (d, J=8 Hz, 2H) 8.10 (d, J=8 Hz, 2H) 8.13 (s, 1H). MS [M+H] Found 411.

Preparation 1: 2-chloro-5-(cyclopropylmethyl)-6a-methyl-6a,7,9,10-tetrahydro-[1,4]oxazino[3,4-h]pteridin-6(5H)-one Morpholine-3-carboxylic acid (10 g, 76 mmol) was dissolved in water (50 ml) and cooled to 5° C. A solution of 50% sodium hydroxide (6.10 g, 76 mmol) was added and the reaction mixture was cooled back to 5° C. An additional portion of 50% sodium hydroxide (7.93 g, 99 mmol) was then diluted to 22 mL with water and added to an addition funnel. Benzyl chloroformate (65.3 ml, 458 mmol) was added to a separate addition funnel and the two reagents were simultaneously added dropwise over about 30 minutes while maintaining the reaction temperature below 10° C. The pH of the mixture was about 6 when the addition was completed. Additional 50% NaOH (1.13 g, 14.3 mmol) was added to adjust pH to 9. The reaction was stirred at 10-15° C. for 2 hours. The reaction mixture was extracted with hexanes (2×30 ml) to remove excess benzyl chloroformate. EtOAc (50 ml) was added into the aqueous phase. The mixture was acidified to pH of about 0 with concentrated HCl (10 g). The organic phase was separated and the aqueous phase was extracted with EtOAc (3×100 ml). The combined organic solution was concentrated to afford an oil. The product was further dried under high vacuum overnight to afford 21.2 g of crude 4-(benzyloxycarbonyl)morpholine-3-carboxylic acid which was used in the next step without further purification. [M−H] calculated for C$_{13}$H$_{15}$NO$_5$, 264. found, 264

4-(Benzyloxycarbonyl)morpholine-3-carboxylic acid (crude material, 21.2 g, about 75 mmol) was dissolved in methanol (250 ml). Sulfuric acid (12.01 ml, 225 mmol) was added slowly with vigorous stirring. An exotherm was noticed and the temperature rose to 34° C. after the addition. Once the addition was complete, reaction solution was heated to 50° C. for 18 hours. The reaction mixture was cooled to room temperature and concentrated to remove most of the methanol. EtOAc (500 ml) was added and the organic solution was washed with water (150 ml), saturated sodium bicarbonate solution (100 ml) and water (150 ml). The organic solution was then concentrated to give a residue which was purified by silica gel column (330 g silica gel, hexanes/EtOAc 5:1) to afford 15.9 gram of 4-benzyl 3-methyl morpholine-3,4-dicarboxylate as clear oil. $^1$H NMR (400 MHz, CDCl$_3$) δ=3.28-3.57 (m, 2H), 3.67 (m, 1H), 3.57-3.96 (m, 5H), 4.4 (dd, 1H), 4.61 (dd, 1H), 5.19 (m, 2H), 7.32-7.4 (m, 5H)

4-Benzyl 3-methyl morpholine-3,4-dicarboxylate (13.98 g, 50.1 mmol) and methyl iodide (5.70 ml, 91 mmol) was dissolved in THF (100 ml). The solution was cooled to −70° C. A solution of NaHMDS in THF (1 M, 91 ml, 91 mmol) was added via syringe over 2 minutes. The reaction solution was stirred for 5 hours at −40 to −70° C. and then was quenched with MeOH (5 ml) and HOAc (3.5 g). The reaction mixture was concentrated. The residue was then partitioned between EtOAc (400 ml) and water (150 ml). The organic phase was separated. The aqueous phase (pH about 7) was extracted with EtOAc (100 ml). The combined organic phases were washed with water (100 ml). The organic solution was then concentrated to give an oil. The residue was purified by silica gel column (220 g silica gel, Hexane/EtOAc 5:1) to afford 11.6 g of 4-benzyl 3-methyl 3-methylmorpholine-3,4-dicarboxylate as an oil (79% yield). $^1$H NMR (400 MHz, CDCl$_3$) δ=1.58 (s, 3H), 3.23-3.78 (m, 9H), 4.99 (m, 2H), 7.17-7.27 (m, 5H)

4-Benzyl 3-methyl 3-methylmorpholine-3,4-dicarboxylate (7.751 g, 26.4 mmol) was dissolved in EtOH (100 ml). 10% Pd/C (1.406 g, 1.321 mmol) was then added. The flask was purged with nitrogen and evacuated before hydrogen was introduced. The mixture was then hydrogenated under 1 atmosphere of hydrogen for 16 hours. The Pd/C was removed by filtering through a Celite® pad. The filtrate was concentrated to afford the product as an oil. MS [M+H] calculated for C$_7$H$_{13}$NO$_3$, 160. found, 160

Methyl 3-methylmorpholine-3-carboxylate (4.21 g, 26.4 mmol) was dissolved in THF (60 ml) to form a clear solution. 2,4-Dichloro-5-nitropyrimidine (5.13 g, 26.4 mmol) was added and the solution was cooled to −10° C. Diisopropylethylamine (6.93 ml, 39.7 mmol) was added while the temperature was maintained at −8 to −10° C. The reaction was stirred for 4 hours at 0° C. and for 16 hours at room temperature. The solvent was removed under reduced pressure. EtOAc (120 ml) was added and the mixture was washed with water (3×30 ml). The organic solution was concentrated to afford 8.4 g of crude methyl 4-(2-chloro-5-nitropyrimidin-4-yl)-3-methylmorpholine-3-carboxylate as an oil. The crude material was used in the next step without further purification. MS [M+H] calculated for C$_{11}$H$_{13}$ClN$_4$O$_5$, 317. found, 317

Methyl 4-(2-chloro-5-nitropyrimidin-4-yl)-3-methylmorpholine-3-carboxylate (crude material, 8.4 g, about 20 mmol) and vanadyl acetylacetonate (0.7 g, 2.64 mmol) were mixed in THF (80 ml). The reaction mixture was hydrogenated under one atmosphere of hydrogen at 35° C. for 18 hours. The starting material was consumed. The reaction mixture was cooled to room temperature. MeOH (10 ml) was added to reaction mixture and stirred for 10 minutes. The mixture was filtered through a Celite® pad. The Celite® pad was washed with mixture of THF (60 ml) and MeOH (10 ml) twice and then a mixture of dichloromethane (80 ml) and methanol (20 ml) three times. The filtrate was combined with washes and concentrated to about 30 ml at which point a solid had precipitated out. EtOAc (40 ml) was added and the mixture was stirred for 10 minutes. The solid was collected by filtration, washed with EtOAc (50 ml) to afford 2.54 g of 2-chloro-6a-methyl-6a,7,9,10-tetrahydro-[1,4]oxazino[3,4-h]pteridin-6(5H)-one. $^1$H NMR (400 MHz, CDCl$_3$) δ=1.44 (s, 3H), 3.23 (m, 1H), 3.53 (m, 1H), 3.69 (d, 1H), 3.88-3.99 (m, 3H), 7.67 (s, 1H), 10.98 (s, 1H)

2-Chloro-6a-methyl-6a,7,9,10-tetrahydro-[1,4]oxazino[3,4-h]pteridin-6(5H)-one (0.846 g, 3.32 mmol) and (bromomethyl)cyclopropane (0.672 g, 4.98 mmol) were mixed in DMSO (5 ml). Potassium carbonate (0.918 g, 6.64 mmol) was added. The mixture was stirred for 30 minutes at room temperature and then for 2 hours at 35° C. EtOAc (40 ml) was added followed by addition of water (30 ml). Aqueous phase was separated and extracted with EtOAc (2×30 ml). The combined organic phase was washed with water (2×20 ml). The organic solution was concentrated to near dryness at which point a solid had precipitated out. EtOAc (5 ml) and hexanes (20 ml) were added and the mixture was stirred for 20 minutes. The solid was collected by filtration to afford 1.35 g product as a white solid. Concentration and crystallization of mother liquor afforded another 0.28 g of compound as second crop. $^1$H NMR (400 MHz, CDCl$_3$) δ=0.34 (m, 2H), 0.46 (m, 2H), 1.13 (m, 1H), 1.39 (s, 3H), 3.21 (m, 1H), 3.55 (m, 1H), 3.66 (d, 1H), 3.77 (m, 1H), 3.85-4.02 (m, 4H), 8.20 (s, 1H)

Preparation 2: methyl 3-methylmorpholine-3-carboxylate

Combine 4-benzyl-5-(hydroxymethyl)-5-methylmorpholin-3-one (11.75 g, 0.05 mol) ethyl acetate (75 ml), and KBr in water (0.5 M, 10 ml), followed by addition of 2,2,6,6-tetramethylpiperidine-1-oxyl (0.16 g, 1 mmol). Add solution of 12% NaClO in water (39 g, 62.5 mmol) dropwise to the mixture over 30 minutes at 5° C. at pH of 8.0-10.0. After 30 minutes, adjust the pH to 5.0 by addition of 35% hydrochloric acid, followed by addition of 25% NaClO2 in water (22.7 g, 62.5 mmol) over 30 minutes. Stirring continues for 3 hours at ambient temperature. Recover the product by extraction with ethyl acetate, washed with brine, to give 4-benzyl-3-methyl-5-oxomorpholine-3-carboxylic acid.

Dissolve 4-benzyl-3-methyl-5-oxomorpholine-3-carboxylic acid (1 eq) in MeOH (10 volumes) and stir. Add sulfuric acid (3 eq) dropwise. Heat at 50° C. for 24 hours. Cool to room temperature and concentrate. Add EtOAc (25 volumes) wash with water (7 volumes), followed by saturated aqueous NaHCO$_3$ (5 volumes), and then water (7 volumes). Dry the EtOAc layer and concentrated to give methyl 4-benzyl-3-methyl-5-oxomorpholine-3-carboxylate.

Dissolve methyl 4-benzyl-3-methyl-5-oxomorpholine-3-carboxylate in THF (10 volumes) and cool to 0° C. Add borane dimethylsulfide complex (1.5 eq) and allow to warm to room temperature. Add water (5 volumes) followed by EtOAc (10 volumes). Separate the organic layer, wash with saturated aqueous NaCl, dry over sodium sulfate, filtered, and concentrate to give methyl 4-benzyl-3-methylmorpholine-3-carboxylate.

Dissolve methyl 4-benzyl-3-methylmorpholine-3-carboxylate in EtOH (10 volumes) and add 10% Pd/C (0.1 eq.). Hydrogenate for 16 hours, filter through Celite®, and concentrate to give the title compound.

EXAMPLE: 16

1-(4-(5-(cyclobutylmethyl)-6a-methyl-6-oxo-5,6,6a,7,9,10-hexahydro-[1,4]oxazino[3,4-h]pteridin-2-yl)phenyl)-3-methylurea

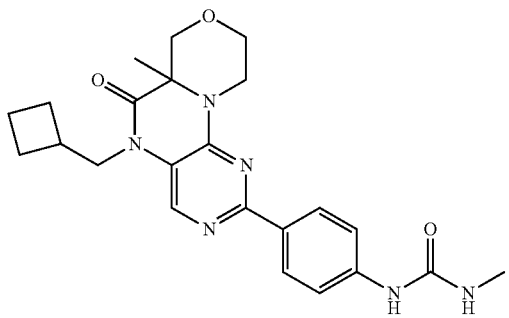

The title compound was prepared by method similar to Example 1, except the title compound was purified by silica gel column chromatography (eluting with 2 to 5% gradient of MeOH in Chloroform) to afford the title compound as a off white solid (15 mg, 17% yield).: $^1$H NMR (400 MHz, DMSO-d$_6$) δ ppm 1.27 (s, 3H) 1.61-1.79 (m, 4H) 1.80-1.96 (m, 2H) 2.51-2.67 (m, 4H) 3.10-3.19 (m, 1H) 3.45-3.64 (m, 2H) 3.83-4.05 (m, 4H) 4.11 (m, 1H) 5.92-6.08 (m, 1H) 7.35-7.47 (d, J=8.0 Hz, 2H) 8.05-8.14 (d, J=8.0 Hz, 2 hours) 8.18 (s, 1H) 8.63 (s, 1H). MS [M+H] found 437.

EXAMPLE: 17

1-(4-(5-cyclopropyl-6a-methyl-6-oxo-5,6,6a,7,9,10-hexahydro-[1,4]oxazino[3,4-h]pteridin-2-yl)phenyl)-3-methylurea

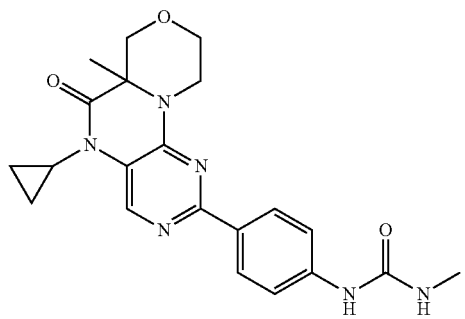

A round-bottomed flask equipped with a magnetic stirrer was added 2,4-dichloro-5-fluoropyrimidine (0.835 g, 5 mmol), DMSO (1 ml), morpholine-3-carboxylic acid (0.656 g, 5.00 mmol) and DIPEA (3.49 ml, 20.00 mmol). The reaction was stirred at 80° C. for 10 minutes then cooled to ambient temperature, HATU (2.85 g, 7.50 mmol) was added followed by cyclopropanamine (0.526 ml, 7.50 mmol) and the reaction mixture was again heated at 80° C. for 2 hours. Upon completion the reaction was suspended in water and filtered. The collected solid was washed successively with water, small amount of ethanol and diethyl ether. The solid was dried in vacuo for 16 hours to afford 4-(2-chloro-5-fluoropyrimidin-4-yl)-N-cyclopropylmorpholine-3-carboxamide (0.325 g, 1.081 mmol, 21.62% yield) as a white solid.

A scintillation vial equipped with a magnetic stirrer was added 4-(2-chloro-5-fluoropyrimidin-4-yl)-N-cyclopropylmorpholine-3-carboxamide (325 mg, 1.081 mmol), DMF (5 ml), Cs$_2$CO$_3$ (528 mg, 1.621 mmol). The reaction was stirred at 60° C. for 16 hours. The reaction solution was poured into water, extracted with ethyl acetate three times and the combined organic layers washed with sat. NaCl. The organic layers were dried with Na$_2$SO$_4$, filtered and dried in-vacuo to give a yellow solid. The crude material was washed with diethyl ether and filtered to afford 2-chloro-5-cyclopropyl-6a,7,9,10-tetrahydro-[1,4]oxazino[3,4-h]pteridin-6(5H)-one (121 mg, 0.431 mmol, 39.9% yield) as a white solid. MS [M+H] found 281.

A round-bottomed flask equipped with a magnetic stirrer was added 2-chloro-5-cyclopropyl-6a,7,9,10-tetrahydro-[1,4]oxazino[3,4-h]pteridin-6(5H)-one (121 mg, 0.431 mmol), DMSO (2 ml), and iodomethane (0.032 ml, 0.517 mmol). The mixture was cooled to 0° C. and added sodium 2-methylpropan-2-olate (49.7 mg, 0.517 mmol) and allowed to stir at 20° C. for 16 hours. The reaction solution was suspended in water, and the precipitate filtered. The collected solid was washed successively with small amount of ethanol and diethyl ether. The solid was collected and dried in-vacuo to afford 2-chloro- 5-cyclopropyl-6a-methyl-6a,7,9,10-tetrahydro-[1,4]oxazino[3,4-h]pteridin-6(5H)-one (100 mg, 0.339 mmol, 79% yield) as a tan solid. MS [M+H] found 295.

A microwave vial equipped with a magnetic stirrer was added 2-chloro-5-cyclopropyl-6a-methyl-6a,7,9,10-tetrahydro-[1,4]oxazino[3,4-h]pteridin-6(5H)-one (100 mg, 0.339 mmol), 1,4-dioxane (2 ml), 1-methyl-3-(4-(4,4,5,5-tetramethyl-1,3,2-dioxaborolan-2-yl)phenyl)urea (141 mg, 0.509 mmol), NaHCO$_3$ (585 µl), followed by PdCl$_2$(dppf) (12.41 mg, 0.017 mmol). The reaction was irradiated in the microwave at 100° C. for 40 min. Upon completion the reaction solution was poured into water and the precipitate filtered. The collected solid was successively washed with water and small amount of ethanol and dried in-vacuo to obtain a solid. This solid was further purified by silica gel chromatography (2 to 5% gradient of MeOH in chloroform). The fractions were collected and concentrated in-vacuo to afford the title compound (27 mg, 0.066 mmol, 19.48% yield) as a white solid. $^1$H NMR (400 MHz, DMSO-d$_4$, D$_2$O) δ ppm 0.55 (m, 1H) 0.78-0.92 (m, 1H) 1.01-1.11 (m, 1H) 1.12-1.24 (m, 2H) 1.45 (s, 3H) 2.65 (s, 3H) 2.78 (s, 1H) 3.26-3.40 (m, 1H) 3.55 (m, 1H) 3.70 (d, J=11.6 Hz, 1H) 3.93 (d, J=11.4 Hz, 1 H) 4.02 (m, 1H) 4.30-4.39 (m, 1H) 7.54 (d, J=8.8 Hz, 2H) 8.08-8.16 (d, J=8.8 Hz, 2H) 8.20 (s, 1H). MS [M+H] found 409.

EXAMPLE: 18

1-(4-((6aS,7S)-5-(cyclopropylmethyl)-6a,7-dimethyl-6-oxo-5,6,6a,7,9,10-hexahydro-[1,4]oxazino[3,4-h]pteridin-2-yl)phenyl)-3-methylurea

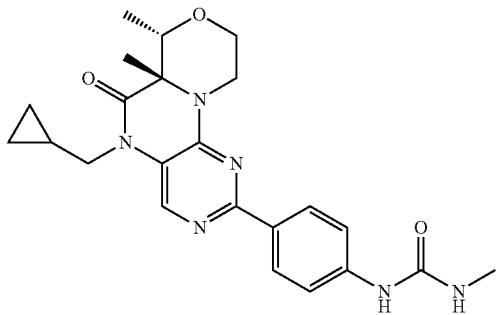

To (2R,3S)-2-amino-3-hydroxybutanoic acid (14.7 g, 123 mol) in NaOH (50%, 70 mL) was added benzaldehyde (14 mL, 123 mmol). The white slurry was stirred at room temperature for 18 h and then cooled to 0° C. NaBH$_4$ (675 mg, 17.9 mmol) was added in two portions over 10 minutes Cooling bath was removed and the thick slurry was stirred at room temperature for 40 minutes and addition NaBH$_4$ (659 mg, 17.4 mmol) was added and stirred at 0° C. for 40 minutes Benzaldehyde (10 mL, 99 mmol) was added, cooled to 0° C. and additional NaBH$_4$ (700 mg, 18.5 mmol) was added. After 5 minutes warmed up to room temperature and stirred for 2 hour. The reaction mixture was acidified with HCl (conc.) to pH of (about 3) and then filtered precipitate, washed with cold water and dried to give (2R,3S)-2-(benzylamino)-3-hydroxybutanoic acid (3.4 g, 13.2%) of white solid. MS [M+H] found 210.

A round-bottomed flask equipped with a magnetic stirrer was added (2R,3S)-2-(benzylamino)-3-hydroxybutanoic acid, HCl (3.4 g, 13.84 mmol), Water (20 ml), sodium hydroxide (1.937 g, 48.4 mmol) and cooled to 0° C. 2-Chloroacetyl chloride (2.201 ml, 27.7 mmol) was added dropwise. The reaction was warmed to 20° C. over 2 hour. The reaction solution was neutralized with 6 N HCl to pH about 2. The reaction solution was extracted with ethyl acetate, and washed with saturated NaCl. The organic layers were collected, dried over Na$_2$SO$_4$, filtered, concentrated in-vacuo to afford (2S,3R)-4-benzyl-2-methyl-5-oxomorpholine-3-carboxylic acid (3.04 g, 88%) a white solid. MS [M+H] found 250.

A round-bottomed flask equipped with a magnetic stirrer was added (2S,3R)-4-benzyl-2-methyl-5-oxomorpholine-3-carboxylic acid (1 g, 4.01 mmol), EtOH (20 ml), thionyl chloride (1.155 ml, 16.05 mmol). The reaction was stirred at 20° C. for 72 hours. Concentrate in vacuo to afford a crude oil. The oil was purified by silica gel column chromatography (eluting with 20% EtOAc in Hexanes using the Moritex SI-60 size 60-half column). The resultant fractions were collected and concentrated in-vacuo to afford (2S,3R)-ethyl 4-benzyl-2-methyl-5-oxomorpholine-3-carboxylate (683 mg, 2.46 mmol, 61.4% yield) as a white solid. MS [M+H] found 278.

To (2S,3R)-ethyl 4-benzyl-2-methyl-5-oxomorpholine-3-carboxylate (683 mg, 2.463 mmol) in THF (6 ml), BH$_3$SMe$_2$ (0.350 ml, 3.69 mmol) at 0° C. The reaction was stirred at 20° C. for 16 h. The reaction solution was quenched with water at 0° C. The layers were separated and the aqueous layer extracted with ethyl acetate. The combined organic layer washed with saturated NaCl. The organic was collected, dried with Na$_2$SO$_4$, filtered and concentrated in-vacuo to give a crude oil. The oil was purified by silica gel column chromatography (eluting with 10-20% gradient of EtOAc in hexanes using a Moritex SI-60 size 20 column). The resultant fractions were collected and concentrated in-vacuo to afford (2S,3R)-ethyl 4-benzyl-2-methylmorpholine-3-carboxylate (683 mg, 2.59 mmol, 105% yield (contained residual solvent)) as a colorless oil. MS [M+H] found 264.

(2S,3R)-Ethyl 4-benzyl-2-methylmorpholine-3-carboxylate (648 mg, 2.461 mmol), ethanol (5 ml), and Pd(OH)$_2$ (34.6 mg, 0.246 mmol) were combined in a round-bottomed flask. The mixture was vigorously stirred and purged of air using house vacuum and recharged with H$_2$ (three times). The reaction was stirred at 20° C. for 16 h. Transferred to a Parr® shaker and pressurized to 50 psi (345 kPa) of H$_2$ for and shaken for 2 hours. The suspension was filtered over a pad of Celite® and washed with ethanol (5 ml). The filtrate was concentrated in vacuo to afford (2S,3R)-ethyl 2-methylmorpholine-3-carboxylate (386 mg, 2.229 mmol, 91% yield) as yellow crystal upon standing.

A scintillation vial equipped with a magnetic stirrer was added (2S,3R)-ethyl 2-methylmorpholine-3-carboxylate (383 mg, 2.211 mmol), DMF (3 ml), 2,4-dichloropyrimidin-5-amine (363 mg, 2.211 mmol), followed by DIEA (0.386 ml, 2.211 mmol). The reaction was stirred at 80° C. for 16 hours. NaOH (2 mL, 2.5N) was added and continued heating at 110° C. for 2 hours. After cooling to room temperature Boc$_2$O (2 eq.) was added and stirred for 16 hours. The reaction was acidified with HCl (6N) to pH of about 2. The reaction mixture was poured into ethyl acetate and washed successively with water, brine, then dried over Na$_2$SO$_4$, and concentrated in vacuo to give a crude oil. Crystals formed after standing for 16 hours. The crystals were filtered and washed with ether to afforded (6aR,7S)-2-chloro-7-methyl-6a,7,9,10-tetrahydro-[1,4]oxazino[3,4-h]pteridin-6(5H)-one (128 mg, 0.503 mmol, 22.73% yield) as a brown solid. The mother liquor was treated with TFA to afforded a crude (2S,3R)-2-methylmorpholine-3-carboxylic acid, TFA (145 mg, 0.559 mmol, 25.3% yield) which was combined with 2,4-dichloropyrimidin-5-amine (164 mg, 1 mmol) in DMF (1 ml) and DIEA (0.524 ml, 3.00 mmol). The reaction was heated at 80° C. for 16 hours. The reaction solution was poured into ethyl acetate and successively washed with water and brine. The organic layer was dried over Na$_2$SO$_4$, concentrated in-vacuo to give a brown oil. The oily residue was allowed to stand for 16 hour to give a solid which was filtered and rinsed with ether to afford (6aR,7S)-2-chloro-7-methyl-6a,7,9,10-tetrahydro-[1,4]oxazino[3,4-h]pteridin-6(5H)-one (77 mg, 0.302 mmol, 30.2% yield). MS [M+H] found 255.

To (6aR,7S)-2-chloro-7-methyl-6a,7,9,10-tetrahydro-[1,4]oxazino[3,4-h]pteridin-6(5H)-one (0.077 g, 0.302 mmol) in DMSO (1 ml) was added sodium tert-butoxide (0.035 g, 0.363 mmol) and stirred at 0° C. for 10 minutes (bromomethyl)cyclopropane (0.034 ml, 0.333 mmol) was added in DMSO (100 μL) and the reaction was stirred at 25° C. for 16 h. Additional (bromomethyl)cyclopropane (0.034 ml, 0.333 mmol) was added and warmed to 60° C. for 2 hours. The reaction solution was poured into water, extracted with ethyl acetate and washed with brine. The organic layer was dried over Na$_2$SO$_4$, filtered, concentrated in-vacuo to give a crude residue (93 mg, 100%). The residue was used in the next step without further purification. MS [M+H] found 309.

To (6aR,7S)-2-chloro-5-(cyclopropylmethyl)-7-methyl-6a,7,9,10-tetrahydro-[1,4]oxazino[3,4-h]pteridin-6(5H)-one (0.093 g, 0.301 mmol) in DMSO (1 ml) and iodomethane (0.038 ml, 0.602 mmol) at 0° C. was added sodium tert-butoxide (0.043 g, 0.452 mmol). The reaction was allowed to warm to 25° C. and stirred for 2 hours. The reaction solution was poured into water, extracted with ethyl acetate and washed with brine. The organic layer was dried over Na$_2$SO$_4$, filtered, and concentrated in-vacuo to give a crude residue (98 mg, 100%). The residue was used in the next step without further purification. MS [M+H] found 323.

A microwave vial equipped with a magnetic stirrer was added crude (6aS,7S)-2-chloro-5-(cyclopropylmethyl)-6a,7-dimethyl-6a,7,9,10-tetrahydro-[1,4]oxazino[3,4-h]pteridin-6(5H)-one (98 mg, 0.304 mmol), 1,4-dioxane (1.5 ml), 1-methyl-3-(4-(4,4,5,5-tetramethyl-1,3,2-dioxaborolan-2-yl)phenyl)urea (126 mg, 0.455 mmol), saturated NaHCO$_3$ (0.500 mL), and PdCl$_2$(dppf) (11.11 mg, 0.015 mmol). The reaction was irradiated in the microwave at 100° C. for 40 minutes. The reaction solution was poured into saturated NaCl and extracted with ethyl acetate three times. The organic layers were collected, dried over Na$_2$SO$_4$, filtered and concentrated in-vacuo to give a brown residue. The residue was purified by preparative HPLC (eluting with 20-30% ACN (containing 0.035% TFA) in water (containing 0.05% TFA) using a Sunfire Prep 5 μm C18, 75×30 mm column to afford the title compound (6.8 mg, 0.016 mmol, 5.13% yield) as a light brown solid. $^1$H NMR (400 MHz, METHANOL-d$_4$) δ ppm 0.46 (m, 2H) 0.60 (m, 2H) 1.20-1.25 (m, 1H) 1.41 (d, J=6.6 Hz, 3H) 1.92 (s, 3H) 2.81 (s, 3H) 3.53-3.67 (m, 1H) 3.79-3.87 (m, 1H) 3.91 (d, J=7.0 Hz, 2H) 3.99-4.11 (m, 1H) 4.27 (d, J=6.6 Hz, 1 H) 4.87-5.00 (m, 1H) 7.65 (d, J=8.8 Hz, 2H) 7.97 (s, 1H) 8.11 (d, J=8.8 Hz, 2H). MS [M+H] found 437.

EXAMPLE: 19

1-(4-((6aR,9R)-5-(cyclopropylmethyl)-6a,9-dimethyl-6-oxo-5,6,6a,7,9,10-hexahydro-[1,4]oxazino[3,4-h]pteridin-2-yl)phenyl)-3-methylurea

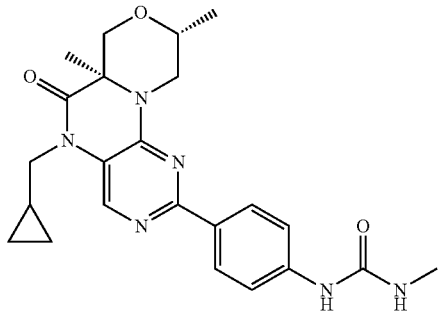

To a 100 mL flask was added 1-benzyl 2-methyl aziridine-1,2-dicarboxylate (1 g, 4.25 mmol), dichloromethane (12 mL), (R)-1-Chloro-2-propanol (0.76 mL, 8.50 mmol), and boron trifluoride diethyl etherate (0.05 mL, 0.398 mmol). The mixture was stirred at room temperature for 15 minutes Solvent was removed in vacuo and the residue purified on silica gel eluting with Hexanes-EtOAc (0-50%) to give (R)-methyl 2-(benzyloxycarbonylamino)-3-(1-chloropropan-2-yloxy)propanoate (583 mg, 41%). MS [M+H] found 330.2.

To a solution of (R)-methyl 2-(benzyloxycarbonylamino)-3-(1-chloropropan-2-yloxy)propanoate (583 mg, 1.77 mmol) in THF—H$_2$O (8 mL-4 mL) was added lithium hydroxide monohydrate (223 mg, 5.30 mmol). The mixture was stirred at room temperature for 25 minutes THF was removed in vacuo and the mixture extracted with EtOAc and dried over Na$_2$SO$_4$. Solvent was removed to give crude (R)-2-(benzyloxycarbonylamino)-3-(1-chloropropan-2-yloxy)propanoic acid as an oil. MS [M+H] found 316.2.

To a solution of (R)-2-(benzyloxycarbonylamino)-3-(1-chloropropan-2-yloxy)propanoic acid in MeOH (10 mL) was added Pd on Carbon (10 wt %, catalytic amount). The mixture was stirred under H$_2$ (1 atm) for 2.5 hours and filtered through a plug of Celite® and rinsed with MeOH. Solvent was removed to give (R)-2-amino-3-(1-chloropropan-2-yloxy) propanoic acid as an off-white solid (308 mg, 96%). MS [M+H] found 182.1.

To solution of (R)-2-amino-3-(1-chloropropan-2-yloxy) propanoic acid (298 mg, 1.64 mmol) in MeOH (10 mL) was added Et$_3$N (0.461 mL, 3.28 mmol). The mixture was equipped with a condenser and refluxed at 80° C. (bath temperature) for 16 hours. More MeOH (10 mL) was added, followed by Et$_3$N (0.922 mL, 6.56 mmol). The flask was sealed with a rubber septum and heated at 100° C. (bath temperature) for 5 hours. Then 2,4-dichloropyrimidin-5-amine (296 mg, 1.80 mmol) was added, followed by more Et$_3$N (0.922 mL, 6.56 mmol). After 30 minutes at room temperature, the flask was sealed with a rubber septum and heated at 100° C. (bath temperature) for 15 hours. Solvent was removed and the residue loaded on silica gel and purified by column chromatography eluting with Hexanes-EtOAc (20-70%). The desired product (R)-2-chloro-9-methyl-6a,7,9,10-tetrahydro-[1,4]oxazino[3,4-h]pteridin-6(5H)-one was obtained as a solid (173 mg, containing some impurities). MS [M+H] found 255.1.

To a solution of (R)-2-chloro-9-methyl-6a,7,9,10-tetrahydro-[1,4]oxazino[3,4-h]pteridin-6(5H)-one (103 mg, 0.404 mmol) in DMF (2.5 mL) at 0° C. was added sodium hydride (21 mg, 0.526 mmol, 60% in oil). After 35 minutes at 0° C., (bromomethyl)cyclopropane (0.051 mL, 0.526 mmol) was added. The mixture was stirred at 0° C. for 30 minutes, then at room temperature for 45 minutes and then sealed and heated at 90° C. (bath temperature) for 2 hours. More (bromomethyl) cyclopropane (0.250 mL) was added and heated at 90° C. for another 24 hours. The mixture was cooled to room temperature, and more sodium hydride (excess) was added followed by (bromomethyl)cyclopropane (0.1 mL). Heating was continued at 90° C. for another 6 hours. Then the mixture was diluted with EtOAc and water, extracted with EtOAc (3×), and dried over Na$_2$SO$_4$. Solvent was removed in vacuo to give crude (R)-2-chloro-5-(cyclopropylmethyl)-9-methyl-6a,7,9,10-tetrahydro-[1,4]oxazino[3,4-h]pteridin-6(5H)-one as a brown oil (124 mg). MS [M+H] found 309.2.

To (R)-2-chloro-5-(cyclopropylmethyl)-9-methyl-6a,7,9,10-tetrahydro-[1,4]oxazino[3,4-h]pteridin-6(5H)-one (124 mg, crude) was added iodomethane (0.25 mL, 4 mmol) and DMSO (2 mL). The mixture was cooled to 0° C. and then −78° C. and sodium 2-methylpropan-2-olate (0.154 g, 1.6 mmol) was added, followed by more DMSO (0.7 mL). The cooling bath was removed and the mixture was stirred at room temperature for 14 hours and then diluted with EtOAc and water, extracted with EtOAc and dried over Na$_2$SO$_4$. Solvent was removed to give crude (R)-2-chloro-5-(cyclopropylmethyl)-6a,9-dimethyl-6a,7,9,10-tetrahydro-[1,4]oxazino[3,4-h]pteridin-6(5H)-one. MS [M+H] found 323.3.

To a microwave vial containing (R)-2-chloro-5-(cyclopropylmethyl)-6a,9-dimethyl-6a,7,9,10-tetrahydro-[1,4]oxazino[3,4-h]pteridin-6(5H)-one (about 0.4 mmol) was added 1-methyl-3-(4-(4,4,5,5-tetramethyl-1,3,2-dioxaborolan-2-yl)phenyl)urea (0.133 g, 0.48 mmol), Pd(dppf)Cl$_2$-dichloromethane, 1,4-dioxane (1.2 mL) and NaHCO$_3$ (sat., 0.6 mL). It was heated in a microwave at 100° C. for 1 hour 45 minutes and then conventionally at 100° C. (bath temperature) for 3 hours. The mixture was diluted with MeOH, passed through a microfilter. The filtrate was purified on the HPLC (40-60% of AcCN in water containing 10 mM NH$_4$HCO$_3$, Phenomenex Gemini 5 μm C18, 75×30 mm column) to give a mixture containing the title product, which was further purified and resolved on a ChiralPak AD-H (5 μm, 10×250 mm, 25-25% of MeOH in liquid CO$_2$) to give the title compound as a white solid (2.1 mg) and having a retention time of 5.20 minutes on ChiralPak AD-H column (5 μm, 2.1×150 mm, 26% of MeOH in liquid CO$_2$). $^1$H NMR (400 MHz, METHANOL-d$_6$) δ ppm 0.4-0.56 (m, 4H) 1.22 (m, 1H) 1.34 (d, J=4 Hz, 3H) 1.44 (s, 3H) 2.79 (s, 3H) 2.95 (dd, J=16, 12 Hz, 1H) 3.73 (m, 1H) 3.82 (m, 2H) 3.95 (m, 1H) 4.12 (d, J=12 Hz, 1H) 4.35 (dd, J=12, 4 Hz, 1H) 7.46 (d, J=8 Hz, 2H) 8.19 m (s, 1H) 8.20 (d, J=8 Hz, 2H). MS [M+H] found 437.4.

EXAMPLE: 20

2-methyl-2-(6a-methyl-2-(4-(3-methylureido)phenyl)-6-oxo-6a,7,9,10-tetrahydro-[1,4]oxazino[3,4-h]pteridin-5(6H)-yl)propanoic acid TFA salt

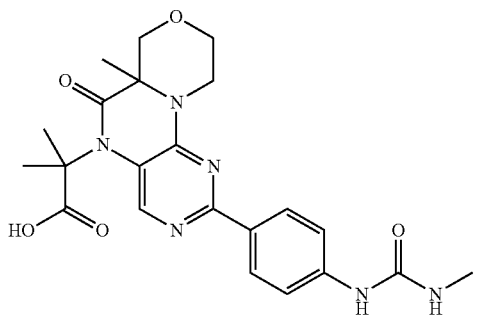

To a mixture of 2-chloro-6a,7,9,10-tetrahydro-[1,4]oxazino[3,4-h]pteridin-6(5H)-one (952 mg, 3.96 mmol), ethyl 2-iodoacetate (1.27 g, 5.93 mmol) in DMF (14 ml) was added K$_2$CO$_3$ (1.64 g, 11.9 mmol) and the reaction mixture was stirred at room temperature for 1 hour. The reaction mixture was concentrated in vacuo to remove DMF. The residue was partitioned between EtOAc and water. The phases were separated and the aqueous phase was extracted with EtOAc. The combined organic phases were washed successively with water and saturated aqueous NaCl, then dried over Na$_2$SO$_4$, filtered and concentrated in vacuo to give a crude solid. The residual solid was purified by silica gel chromatography (hexane/ethyl acetate, 19:1 to 1:1) to afford a pale yellow solid. The solid was triturated with hexane/ethyl acetate (4:1), collected by filtration, rinsed with hexane/ethyl acetate (5:1) and dried to afford ethyl 2-(2-chloro-6-oxo-6a,7,9,10-tetrahydro-[1,4]oxazino[3,4-h]pteridin-5(6H)-yl)acetate (953 mg, 2.92 mmol, 74% yield) as a white solid. MS [M+H] found 327.

To a mixture of ethyl 2-(2-chloro-6-oxo-6a,7,9,10-tetrahydro-[1,4]oxazino[3,4-h]pteridin-5(6H)-yl)acetate (440 mg, 1.35 mmol) and iodomethane (1.26 ml, 20.2 mmol) in DMSO (10 ml) at 0° C. was added sodium 2-methylpropan-2-olate (907 mg, 9.43 mmol). The ice-bath was removed and the reaction mixture was stirred at room temperature for 16 hours. The reaction mixture was poured into water and extracted with EtOAc. The combined organic phases were dried over Na$_2$SO$_4$, filtered and concentrated in vacuo to give a crude solid. The solid was purified by silica gel chromatography (hexane/ethyl acetate, 19:1 to 1:1) to concentration in vacuo gave a crude solid, which was purified by Purif 2 (L) (silica gel, hexane/ethyl acetate, 19:1 to 1:1) to afford ethyl 2-(2-chloro-6a-methyl-6-oxo-6a,7,9,10-tetrahydro-[1,4]oxazino[3,4-h]pteridin-5(6H)-yl)-2-methylpropanoate (266.9 mg, 53% yield) and methyl 2-(2-chloro-6a-methyl-6-oxo-6a,7,9,10-tetrahydro-[1,4]oxazino[3,4-h]pteridin-5(6H)-yl)-2-methylpropanoate (82.6 mg, 17% yield). MS [M+H] for methyl 2-(2-chloro-6a-methyl-6-oxo-6a,7,9,10-tetrahydro-[1,4]oxazino[3,4-h]pteridin-5(6H)-yl)-2-methylpropanoate, found 355.

To a suspension of methyl 2-(2-chloro-6a-methyl-6-oxo-6a,7,9,10-tetrahydro-[1,4]oxazino[3,4-h]pteridin-5(6H)-yl)-2-methylpropanoate (82.6 mg, 0.233 mmol) in THF (6 ml) and MeOH (3 ml) was added 1 N NaOH aqueous solution (0.698 ml, 0.698 mmol), and the mixture was stirred for 2 days. After further addition of THF (20 ml) and MeOH (10 ml), the mixture was stirred for 16 hours and concentrated in vacuo to give a crude 2-(2-chloro-6a-methyl-6-oxo-6a,7,9,10-tetrahydro-[1,4]oxazino[3,4-h]pteridin-5(6H)-yl)-2-methylpropanoic acid which was used in the next step without further purification. MS [M+H] found 341.

To crude 2-(2-chloro-6a-methyl-6-oxo-6a,7,9,10-tetrahydro-[1,4]oxazino[3,4-h]pteridin-5(6H)-yl)-2-methylpropanoic acid (79 mg, about 0.233 mmol, as a mixture with its methylester) was added 1-methyl-3-(4-(4,4,5,5-tetramethyl-1,3,2-dioxaborolan-2-yl)phenyl)urea (0.077 g, 0.28 mmol), Pd(dppf)C12-dichloromethane, 1,4-dioxane (3 mL) and NaHCO$_3$ (sat., 1.5 mL). It was heated under an air-filled balloon (1 atm) at 100° C. (bath temperature) for 1.5 hours and then LiOH.H$_2$O (100 mg) was added and heated continued at 80° C. (bath temperature) for 1 hour and 40 minutes The mixture was diluted with water and MeOH, passed through a microfilter. The filtrate was acidified with concentrated HCl (0.1 mL) to pH<7 and then purified on the HPLC (20-20% of AcCN [containing 0.035% TFA] in water [containing 0.05% TFA], Phenomenex Gemini 5 μm C18, 75×30 mm column) to give 2-methyl-2-(6a-methyl-2-(4-(3-methylureido)phenyl)-6-oxo-6a,7,9,10-tetrahydro-[1,4]oxazino[3,4-h]pteridin-5(6H)-yl)propanoic acid as a clear semisolid (10.2 mg). $^1$H NMR (400 MHz, METHANOL-d$_6$) δ ppm 1.55 (s, 3H) 1.68 (s, 3H) 1.81 (s, 3H) 2.80 (s, 3H) 3.49 (m, 1H) 3.69 (dd, J=12, 4 Hz, 1H) 3.74 (d, J=12 Hz, 1H) 4.05 (d, J=12 Hz, 1H) 4.15 (dd, J=12, 4 Hz, 1H) 4.48 (d, J=12 Hz, 1H) 7.62 (d, J=8 Hz, 2H) 8.10 (s, 1H) 8.14 (d, J=8 Hz, 2H). MS [M+H] found 455.4.

EXAMPLE: 21

1-(4-(5-(((S)-2,2-dimethyl-1,3-dioxolan-4-yl)methyl)-6a-methyl-6-oxo-5,6,6a,7,9,10-hexahydro-[1,4]oxazino[3,4-h]pteridin-2-yl)phenyl)-3-methylurea

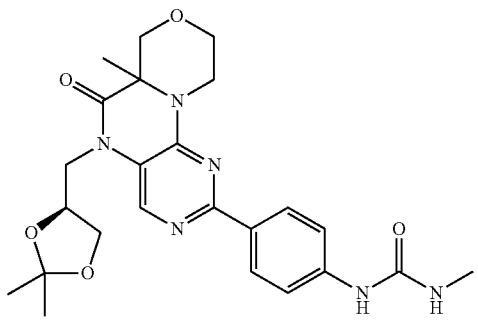

The title compound was prepared by method similar to Example 1, except the title compound was purified by preparative HPLC (eluting with 20-30% ACN (containing 0.035% TFA) in water (containing 0.05% TFA) using a Sunfire Prep 5 μm C18, 75×30 mm column). The clean fractions were combined and using solid NaHCO$_3$ adjusted the solution pH>8.0. The product was extracted with ethyl acetate 3 times and the combined organic layer was washed with saturated NaCl. The organic layer was dried with Na$_2$SO$_4$, filtered, and concentrated in-vacuo to give the title compound (18.9 mg, 37.8% yield) as a white solid. $^1$H NMR (400 MHz, DMSO-d$_6$) δ ppm 1.24 (d, J=4.04 Hz, 3H) 1.29 (d, J=5.05 Hz, 3H) 1.34 (d, J=8.84 Hz, 3H) 2.62-2.70 (m, 3H) 3.18-3.27 (m, 1H) 3.53-3.74 (m, 3H) 3.94-4.10 (m, 4H) 4.10-4.26 (m, 2H) 4.30-4.42 (m, 1H) 6.12-6.22 (m, 1H) 7.46-7.53 (m, 2H) 8.17 (dd, J=8.72, 1.14 Hz, 2 H) 8.38 (d, J=8.08 Hz, 1H) 8.84 (s, 1H). MS [M+H] found 483.4.

EXAMPLE: 22

1-(4-(5-((S)-2,3-dihydroxypropyl)-6a-methyl-6-oxo-5,6,6a,7,9,10-hexahydro-[1,4]oxazino[3,4-h]pteridin-2-yl)phenyl)-3-methylurea

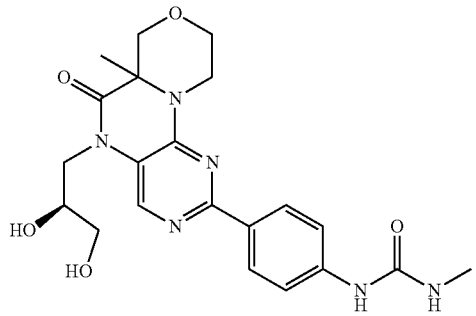

Combined 2-chloro-5-(((S)-2,2-dimethyl-1,3-dioxolan-4-yl)methyl)-6a-methyl-6a,7,9,10-tetrahydro-[1,4]oxazino[3,4-h]pteridin-6(5H)-one (0.201 g, 0.545 mmol), 1-methyl-3-(4-(4,4,5,5-tetramethyl-1,3,2-dioxaborolan-2-yl)phenyl)urea (0.166 g, 0.599 mmol), PdCl$_2$(dppf) (0.080 g, 0.109 mmol), sodium carbonate (saturated in water) (1.5 ml, 0.545 mmol) and dioxane (3 ml). The suspension was heated by microwave irradiation at 100° C. for 45 minutes. The reaction mixture was filtered via syringe filter and purified the title compound was purified by preparative HPLC (eluting with 20-30% ACN (containing 0.035% TFA) in water (containing 0.05% TFA) using a Sunfire Prep 5 μm C18, 75×30 mm column. Product containing fractions were concentrated in vacuo to remove about ½ of the total volume and allowed t and let sit at room temperate. After 3 days, the sample was concentrated and purified by HPLC (15-25% of AcCN [containing 0.035% TFA] in water [containing 0.05% TFA], Phenomenex Gemini 5 μm C18, 75×30 mm column) and the product containing fractions were combined, concentrated in vacuo and lyophilized, affording the title compound (27.9 mg, 11.5% yield) as a pale green solid. $^1$H NMR (400 MHz, DMSO-d$_6$) δ ppm 1.34-1.46 (m, 3H) 2.66 (s, 3H) 3.23-3.36 (m, 1H) 3.36-3.46 (m, 1H) 3.59 (t, J=12.00 Hz, 1H) 3.66-3.74 (m, 1H) 3.74-3.87 (m, 2H) 3.88-4.66 (m, 7H) 6.12 (br. s., 1H) 7.44-7.58 (m, 2H) 8.09-8.23 (m, 2H) 8.28-8.45 (m, 1H) 8.73-8.87 (m, 1 H). MS [M+H] found 443.4.

EXAMPLE: 23

1-(4-((S)-5-(S)-2,3-dihydroxypropyl)-6a-methyl-6-oxo-5,6,6a,7,9,10-hexahydro-[1,4]oxazino[3,4-h]pteridin-2-yl)phenyl)-3-methylurea and

EXAMPLE: 24

1-(4-((R)-5-(S)-2,3-dihydroxypropyl)-6a-methyl-6-oxo-5,6,6a,7,9,10-hexahydro-[1,4]oxazino[3,4-h]pteridin-2-yl)phenyl)-3-methylurea

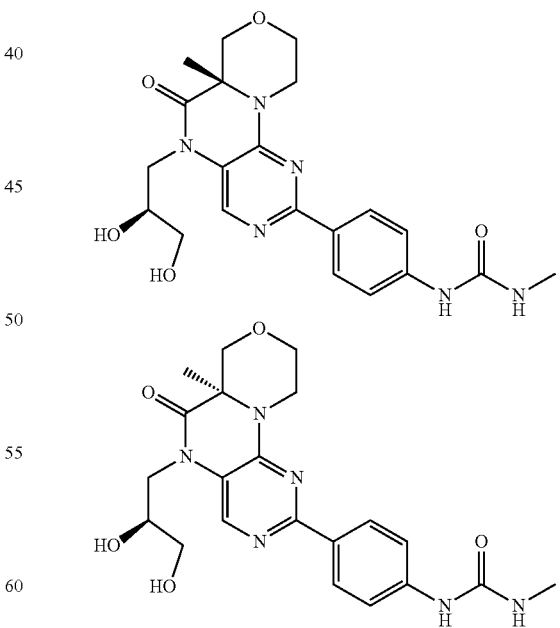

The product of Example 22 (25.7 mg) was separated by SFC (Chiralpak AD-H column, flow rate=15 mL/min, modifier 30% methanol in CO$_2$) to give Isomer 1 (5.3 mg, t=3.29 min) and Isomer 2 (4.3 mg, t=7.63 min).

EXAMPLE: 25

1-methyl-3-(4-(6a-methyl-6-oxo-5-(tetrahydro-2H-pyran-4-yl)-5,6,6a,7,9,10-hexahydro-[1,4]oxazino[3,4-h]pteridin-2-yl)phenyl)urea

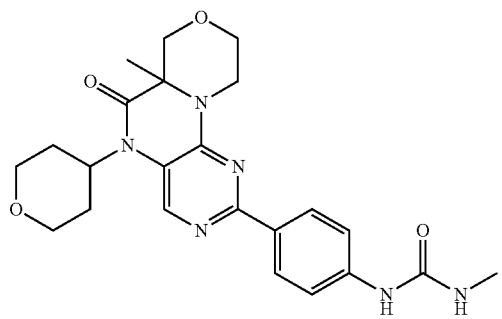

In a 100 mL round bottomed flask containing 2,4-dichloropyrimidin-5-amine (1.0 g, 6.10 mmol) in 16.5 mL of dichloromethane was added dihydro-2H-pyran-4 (3H)-one (0.794 g, 7.93 mmol), cooled to 0° C. then added the solution of titanium tetrachloride (0.740 ml, 6.71 mmol) in 10 mL of dichloromethane. The reaction was removed from the ice bath and with continued stirring, slowly warmed to room temperature. After 3.5 h, sodium cyanoborohydride (1.15 g, 18.29 mmol) was added in 4 equal portions over 10 minutes and the reaction was stirred at room temperature for 16 h. The suspension was diluted with water (150 mL) and transferred to an appropriate separatory funnel. The layers were separated and then extracted the aqueous layer with MTBE (1×150 mL). The organic layers were combined, washed with sat. NaCl, dried over $Na_2SO_4$, filtered and concentrated in vacuo affording a clear orange oil. The crude oil was purified by silica chromatography (30% EtOAc/Hexanes); the appropriate fractions were combined and concentrated in vacuo to afford 2,4-dichloro-N-(tetrahydro-2H-pyran-4-yl)pyrimidin-5-amine (0.336 g, 60% pure, 22% yield). MS [M+H] found 249.1.

In a 100 mL round bottomed flask containing 2,4-dichloro-N-(tetrahydro-2H-pyran-4-yl)pyrimidin-5-amine (0.336 g, 1.354 mmol) in 2.0 mL of DMSO was added morpholine-3-carboxylic acid hydrochloride (0.295 g, 1.761 mmol) and DIPEA (1.183 ml, 6.77 mmol). The reaction mixture was stirred at 100° C. for 16 h. The reaction was cooled to room temperature, diluted with 30 mL of water, transferred to an appropriate separatory funnel and extracted with EtOAc (3×25 mL). The organic layers were combined, washed with sat. NaCl, dried over $Na_2SO_4$, filtered and concentrated in vacuo affording an oil. The oil was suspended in 10 mL of $Et_2O$, added 2 drops of EtOH and sonicated until a yellow precipitate appeared. Let mixture sit at room temperature for 1 h, collected solids by vacuum filtration, washed with additional $Et_2O$, hexanes and dried under high vacuum affording 2-chloro-5-(tetrahydro-2H-pyran-4-yl)-6a,7,9,10-tetrahydro-[1,4]oxazino[3,4-h]pteridin-6(5H)-one. (90 mg, 20.4% yield) as a light yellow solid. $^1$H NMR (400 MHz, CHLOROFORM-d) δ ppm 1.54-1.65 (m, 1H) 1.70 (dd, J=12.88, 2.02 Hz, 1H) 2.51-2.70 (m, 2H) 3.03 (ddd, J=13.58, 12.32, 3.92 Hz, 1H) 3.41-3.66 (m, 4H) 4.03 (dd, J=11.87, 3.79 Hz, 4H) 4.32-4.47 (m, 2H) 4.59 (tt, J=12.47, 4.07 Hz, 1H) 8.05 (s, 1H). MS [M+H] found 325.2.

In a microwave reaction vial, 2-chloro-5-(tetrahydro-2H-pyran-4-yl)-6a,7,9,10-tetrahydro-[1,4]oxazino[3,4-h]pteridin-6(5H)-one (0.0258 g, 0.079 mmol), 1-methyl-3-(4-(4,4,5,5-tetramethyl-1,3,2-dioxaborolan-2-yl)phenyl)urea (0.024 g, 0.087 mmol), $PdCl_2$(dppf) (0.012 g, 0.016 mmol) and sodium bicarbonate (saturated solution) (0.3 ml, 0.079 mmol) were suspended in dioxane (0.794 ml). The suspension was heated by microwave irradiation at 100° C. for 1 h. The reaction mixture was cooled and purified by preparative HPLC (eluting with 15-25% ACN (containing 0.035% TFA) in water (containing 0.05% TFA) using a Sunfire Prep 5 μm C18, 75×30 mm column). The clean fractions were combined, concentrated in vacuo and lyophilized, affording the title compound (10.0 mg, 28.7% yield) as a white solid. $^1$H NMR (400 MHz, DMSO-$d_6$) δ ppm 1.56-1.73 (m, 2H) 2.61-2.70 (m, 3H) 3.01 (td, J=12.82, 3.66 Hz, 1 H) 3.35-3.46 (m, 1H) 3.46-3.62 (m, 3H) 3.74-3.89 (m, 1H) 3.89-4.04 (m, 2H) 4.14-4.30 (m, 4H) 4.38 (ddt, J=11.81, 7.89, 4.04, 4.04 Hz, 1H) 4.48 (d, J=12.13 Hz, 1H) 6.13 (br. s., 1H) 7.52 (d, J=8.84 Hz, 2H) 8.13-8.20 (m, 2H) 8.40 (s, 1H) 8.81 (s, 1H). MS [M+H] found 439.4.

To a 20 mL vial containing 2-chloro-5-(tetrahydro-2H-pyran-4-yl)-6a,7,9,10-tetrahydro-[1,4]oxazino[3,4-h]pteridin-6(5H)-one (0.0907 g, 0.279 mmol) was added DMSO (0.5 mL); placed in a dry ice-acetone bath and then added sodium tert-butoxide (0.030 g, 0.307 mmol) followed by DMSO (0.5 mL) and iodomethane (0.019 ml, 0.307 mmol). The dry ice-acetone bath was removed and the mixture was allowed to warm up to room temperature and stirred for 16 h. The reaction was diluted with 10 mL of water and vigorously stirred at room temperature. Collected rust/orange solids by vacuum filtration, washed with additional water and dried under high vacuum affording 2-chloro-6a-methyl-5-(tetrahydro-2H-pyran-4-yl)-6a,7,9,10-tetrahydro-[1,4]oxazino[3,4-h]pteridin-6(5H)-one (46.0 mg, 48.4% yield) as a yellow solid. $^1$H NMR (400 MHz, CHLOROFORM-d) δ ppm 1.41 (d, J=0.76 Hz, 3H) 2.48-2.72 (m, 2H) 3.17-3.34 (m, 1H) 3.41-3.77 (m, 5H) 3.94-4.19 (m, 6H) 4.61 (tt, J=12.38, 4.29 Hz, 1 H) 7.98-8.14 (m, 1H). MS [M+H] found 339.3.

In a microwave reaction vial, 2-chloro-6a-methyl-5-(tetrahydro-2H-pyran-4-yl)-6a,7,9,10-tetrahydro-[1,4]oxazino[3,4-h]pteridin-6(5H)-one (0.046 g, 0.136 mmol), 1-methyl-3-(4-(4,4,5,5-tetramethyl-1,3,2-dioxaborolan-2-yl)phenyl)urea (0.041 g, 0.149 mmol), $PdCl_2$(dppf) (0.020 g, 0.027 mmol) and sodium bicarbonate (saturated solution) (0.3 ml, 0.136 mmol) were suspended in dioxane (1.36 ml). The suspension was heated by microwave irradiation at 100° C. for 1 hour, then heated by microwave irradiation at 120° C. for an additional 30 minutes. The reaction was purified by preparative HPLC (eluting with 20-30% ACN (containing 0.035% TFA) in water (containing 0.05% TFA) using a Sunfire Prep 5 μm C18, 75×30 mm column). Product containing fractions were combined, concentrated in vacuo and lyophilized, affording the title compound (41.4 mg, 67.4% yield) as an off-white solid. $^1$H NMR (400 MHz, DMSO-$d_6$) δ ppm 1.32 (s, 3H) 1.55-1.74 (m, 2H) 2.62-2.70 (m, 3H) 3.25 (td, J=13.14, 4.04 Hz, 1 H) 3.34-3.45 (m, 1H) 3.47-3.72 (m, 3H) 3.87-4.00 (m, 3H) 4.06 (dd, J=11.62, 3.79 Hz, 2 H) 4.19 (dd, J=13.77, 2.15 Hz, 3H) 6.01-6.24 (m, 1H) 7.48-7.57 (m, 2H) 8.13-8.22 (m, 2 H) 8.48 (s, 1H) 8.81 (s, 1H). MS [M+H] found 453.4.

EXAMPLE: 26

(S)-1-methyl-3-(4-(6a-methyl-6-oxo-5-(tetrahydro-2H-pyran-4-yl)-5,6,6a,7,9,10-hexahydro-[1,4]oxazino[3,4-h]pteridin-2-yl)phenyl)urea and

EXAMPLE: 27

(R)-1-methyl-3-(4-(6a-methyl-6-oxo-5-(tetrahydro-2H-pyran-4-yl)-5,6,6a,7,9,10-hexahydro-[1,4]oxazino[3,4-h]pteridin-2-yl)phenyl)urea

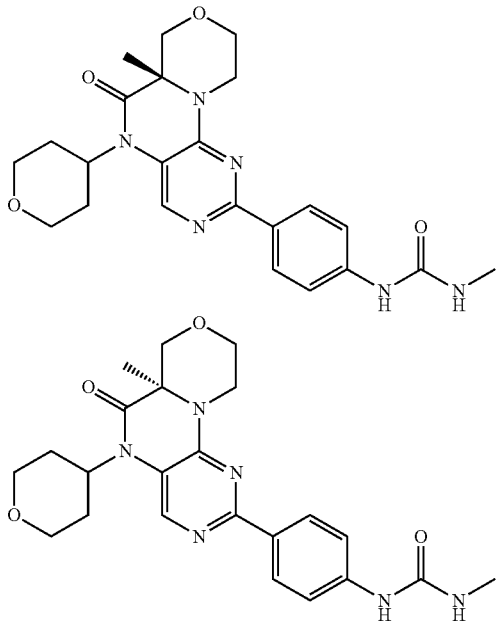

The product of Example 25 (38.3 mg) was separated by SFC (Chiralpak AD-H column, flow rate=55 mL/min, modifier 45% methanol) to give Isomer 1 (10.0 mg, t=1.86 min) and Isomer 2 (10.2 mg, t=3.38 min).

EXAMPLE: 28

1-methyl-3-(4-(6a-methyl-5-neopentyl-6-oxo-5,6,6a,7,9,10-hexahydro-[1,4]oxazino[3,4-h]pteridin-2-yl)phenyl)urea

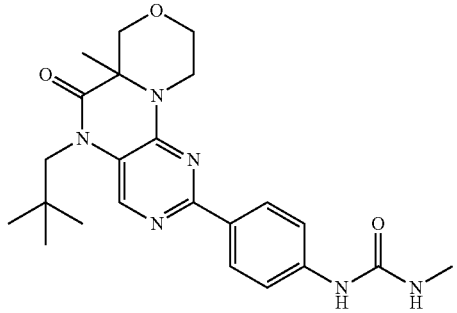

The title compound was prepared by method similar to Example 1, except the title compound was purified by preparative HPLC (eluting with 30-35% ACN (containing 0.035% TFA) in water (containing 0.05% TFA) using a Sunfire Prep 5 μm C18, 75×30 mm column). The clean fractions were combined, concentrated in vacuo and lyophilized, affording the title compound (9.4 mg, 2.3% yield) as a light yellow solid. $^1$H NMR (400 MHz, DMSO-$d_6$) δ ppm 0.90 (s, 9H) 1.35 (s, 3H) 2.62-2.70 (m, 3H) 3.27 (td, J=13.14, 3.79 Hz, 2H) 3.60-3.69 (m, 1 H) 3.88 (s, 2H) 4.00 (d, J=11.62 Hz, 1H) 4.07 (dd, J=11.24, 3.66 Hz, 1H) 4.20 (d, J=11.62 Hz, 1H) 6.08 (br. s., 1H) 7.50 (d, J=8.84 Hz, 2H) 8.14-8.21 (m, 2H) 8.46 (s, 1H) 8.74 (s, 1H). MS [M+H] found 439.4.

EXAMPLE: 29

1-methyl-3-(4-(6a-methyl-6-oxo-5-(tetrahydrofuran-3-yl)-5,6,6a,7,9,10-hexahydro-[1,4]oxazino[3,4-h]pteridin-2-yl)phenyl)urea

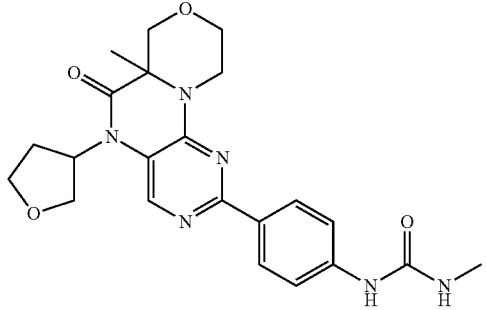

The title compound was prepared by method similar to Example 25. After the microwave irradiation the title compound was purified by preparative HPLC (eluting with 15-20% ACN (containing 0.035% TFA) in water (containing 0.05% TFA) using a Sunfire Prep 5 μm C18, 75×30 mm column). The clean fractions were combined, concentrated in vacuo and lyophilized, affording the title compound (5.5 mg, 27.2% yield) as a pale yellow solid. $^1$H NMR (400 MHz, DMSO-$d_6$) δ ppm 1.31-1.43 (m, 3H) 1.98-2.10 (m, 1H) 2.11-2.28 (m, 2H) 2.61-2.71 (m, 3H) 3.23-3.36 (m, 1H) 3.52-3.77 (m, 3H) 3.80-4.10 (m, 4H) 4.16-4.30 (m, 2H) 5.34-5.48 (m, 1H) 6.15 (br. s., 1H) 7.48-7.58 (m, 2H) 8.17 (d, J=8.84 Hz, 2H) 8.37 (s, 1H) 8.83-8.92 (m, 1H). MS [M+H] found 439.4.

EXAMPLE: 30

1-cyclopropyl-3-(4-(6a-methyl-6-oxo-5-(tetrahydrofuran-3-yl)-5,6,6a,7,9,10-hexahydro-[1,4]oxazino[3,4-h]pteridin-2-yl)phenyl)urea

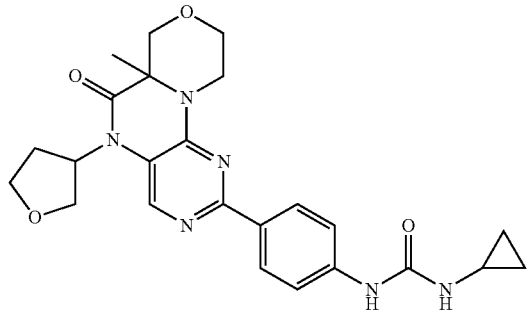

The title compound was prepared by method similar to Example 25. After the microwave irradiation the title compound was purified by preparative HPLC (eluting with 23-25% ACN (containing 0.035% TFA) in water (containing 0.05% TFA) using a Sunfire Prep 5 μm C18, 75×30 mm column). The clean fractions were combined, concentrated in vacuo and lyophilized, affording the title compound (34.4 mg, 24% yield) as a light yellow solid. $^1$H NMR (400 MHz, DMSO-$d_6$) δ ppm 0.36-0.45 (m, 2H) 0.57-0.69 (m, 2H) 1.38 (d, J=7.83 Hz, 3H) 2.23 (d, J=7.33 Hz, 2H) 3.30 (t, J=12.63 Hz, 1H) 3.51-3.78 (m, 3H) 3.79-4.12 (m, 4H) 4.16-4.36 (m, 2H) 5.35-5.50 (m, 1H) 5.57-5.73 (m, 1H) 6.57 (br. s., 1H) 7.48-7.59 (m, 2H) 8.12-8.22 (m, 2H) 8.36 (s, 1H) 8.71 (d, J=5.56 Hz, 1H). MS [M+H] found 465.4.

EXAMPLE: 31

1-ethyl-3-(4-(6a-methyl-6-oxo-5-(tetrahydro-2H-pyran-4-yl)-5,6,6a,7,9,10-hexahydro-[1,4]oxazino[3,4-h]pteridin-2-yl)phenyl)urea

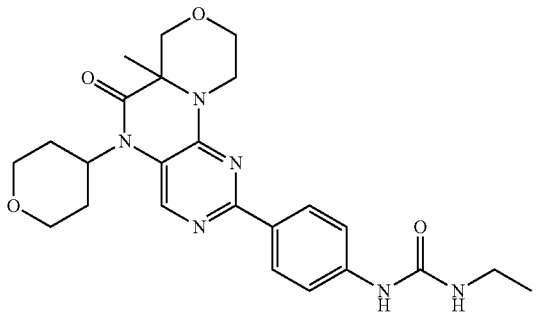

The title compound was prepared by method similar to Example 25. After the microwave irradiation the title compound was purified by preparative HPLC (eluting with 20-30% ACN (containing 0.035% TFA) in water (containing 0.05% TFA) using a Sunfire Prep 5 μm C18, 75×30 mm column). The product containing fractions were combined, concentrated in vacuo and lyophilized, affording the title compound (41.4 mg, 67.4% yield) as a white solid. $^1$H NMR (400 MHz, DMSO-$d_6$) δ ppm 1.06 (t, J=7.07 Hz, 3H) 1.30 (s, 3H) 1.54-1.73 (m, 2H) 2.56-2.71 (m, 1H) 3.05-3.15 (m, 2H) 3.19-3.30 (m, 1H) 3.39 (t, J=10.99 Hz, 1H) 3.47-3.72 (m, 3H) 3.86-4.00 (m, 3H) 4.06 (dd, J=11.49, 3.66 Hz, 1H) 4.15 (d, J=11.62 Hz, 1H) 4.34-4.49 (m, 2H) 6.22 (br. s., 1H) 7.51 (d, J=8.84 Hz, 2H) 8.17 (d, J=8.84 Hz, 2H) 8.51 (s, 1 H) 8.74 (s, 1H). MS [M+H] found 467.4.

EXAMPLE: 32

1-cyclopropyl-3-(4-(6a-methyl-6-oxo-5-(tetrahydro-2H-pyran-4-yl)-5,6,6a,7,9,10-hexahydro-[1,4]oxazino[3,4-h]pteridin-2-yl)phenyl)urea

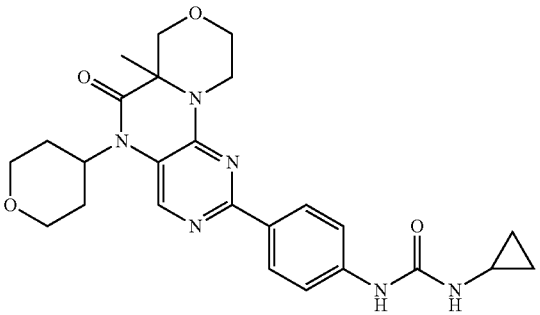

The title compound was prepared by method similar to Example 25. After the microwave irradiation the title compound was purified by preparative HPLC (eluting with 23-30% ACN (containing 0.035% TFA) in water (containing 0.05% TFA) using a Sunfire Prep 5 μm C18, 75×30 mm column). The product containing fractions were combined, concentrated in vacuo and lyophilized, affording the title compound (64.3 mg, 32.5% yield) as a pale yellow solid. $^1$H NMR (400 MHz, DMSO-$d_6$) δ ppm 0.36-0.46 (m, 2H) 0.59-0.69 (m, 2H) 1.30 (s, 3 H) 1.55-1.73 (m, 2H) 2.41-2.48 (m, 1H) 2.52-2.70 (m, 2H) 3.24 (td, J=13.14, 4.04 Hz, 1H) 3.33-3.45 (m, 1H) 3.47-3.73 (m, 4H) 3.86-4.22 (m, 4H) 4.34-4.50 (m, 2H) 6.50 (br. s., 1 H) 7.52 (d, J=8.84 Hz, 2H) 8.13-8.23 (m, 1H) 8.51 (s, 1H) 8.62 (s, 1H). MS [M+H] found 479.4.

EXAMPLE: 33

(S)-1-cyclopropyl-3-(4-(6a-methyl-6-oxo-5-(tetrahydro-2H-pyran-4-yl)-5,6,6a,7,9,10-hexahydro-[1,4]oxazino[3,4-h]pteridin-2-yl)phenyl)urea and

EXAMPLE: 34

(R)-1-cyclopropyl-3-(4-(6a-methyl-6-oxo-5-(tetrahydro-2H-pyran-4-yl)-5,6,6a,7,9,10-hexahydro-[1,4]oxazino[3,4-h]pteridin-2-yl)phenyl)urea

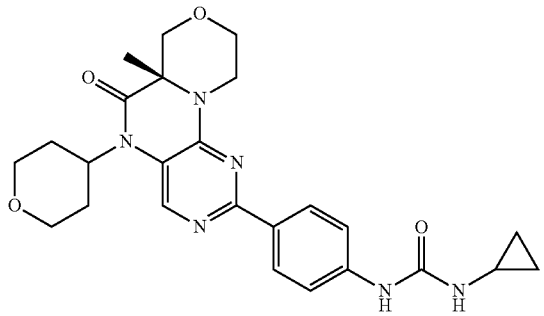

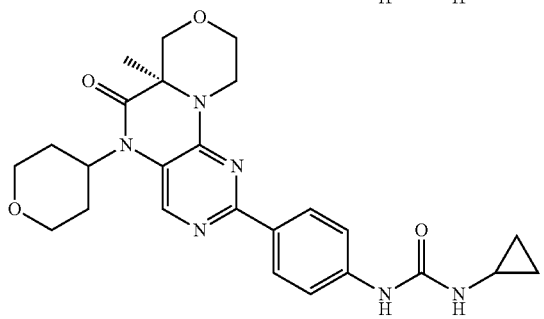

The product of Example 32 (59 mg) was separated by SFC (Chiral pak AD-H column, flow rate=50 mL/min, modifier 35% iPrOH) to give Isomer 1 (12.0 mg, t=1.66 min) and Isomer 2 (15.8 mg, t=2.50 min).

EXAMPLE: 35

1-(4-[5-(3-methoxypropyl)-6a-methyl-6-oxo-5,6,6a,7,9,10-hexahydro[1,4]oxazino[3,4-h]pteridin-2-yl]phenyl)-3-methylurea

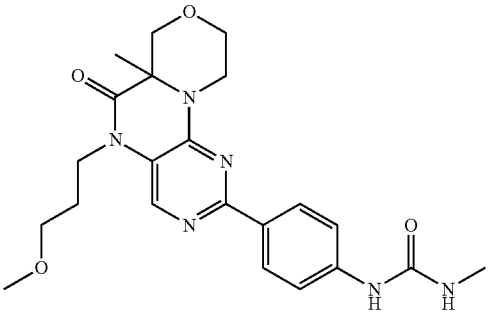

The title compound was prepared by method similar to Example 1, except the title compound was chromatographed by silica gel (hexane/ethyl acetate/methanol, 80:20:0 to 0:100:0 to 0:17:3) and then this resulting solid was triturated with EtOAc/hexane (1:1), collected by filtration and dried to afford the title compound (67.2 mg, 0.153 mmol, 63% yield) as a beige solid. $^1$H NMR (400 MHz, DMSO-$d_6$) δ ppm 1.31-1.38 (m, 3H) 1.75-1.88 (m, 2H) 2.66 (d, J=4.55 Hz, 2H) 3.18-3.32 (m, 5H) 3.38 (t, J=6.06 Hz, 2H) 3.52-3.63 (m, 1H) 3.67 (d, J=11.37 Hz, 1H) 3.84-4.11 (m, 4H) 4.18 (dd, J=13.64, 2.27 Hz, 1H) 6.05 (q, J=4.46 Hz, 1H) 7.48 (d, J=8.84 Hz, 2H) 8.18 (d, J=8.84 Hz, 2H) 8.24 (s, 1H) 8.70 (s, 1H). MS [M+H] found 441.

EXAMPLE: 36

(S)-1-(4-[5-(3-methoxypropyl)-6a-methyl-6-oxo-5,6,6a,7,9,10-hexahydro[1,4]oxazino[3,4-h]pteridin-2-yl]phenyl)-3-methylurea and

EXAMPLE: 37

(R)-1-(4-[5-(3-methoxypropyl)-6a-methyl-6-oxo-5,6,6a,7,9,10-hexahydro[1,4]oxazino[3,4-h]pteridin-2-yl]phenyl)-3-methylurea

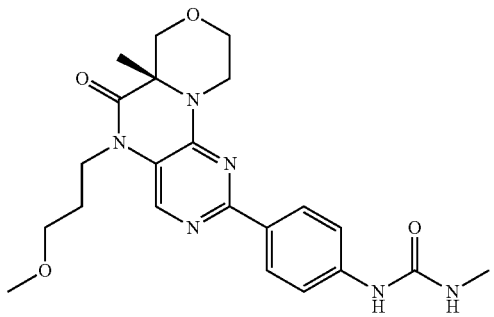

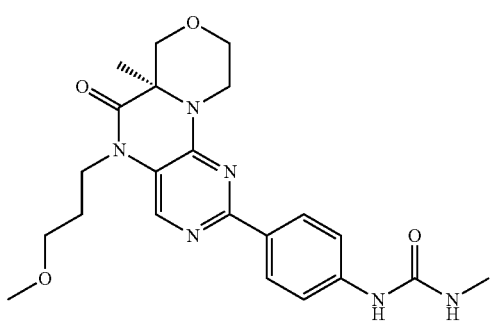

The product of 35 (58 mg) was separated by chiral SFC (Chiralpak IA column, flowrate=1.25 mL/min, modifier 16% methanol/dichloromethane (80/20) in liquid $CO_2$ to give Isomer 1 (9.2 mg, t=7.65 min) and Isomer 2 (8.0 mg, t=10.6 min).

EXAMPLE: 38

1-(4-[5-(2-methoxyethyl)-6a-methyl-6-oxo-5,6,6a,7,9,10-hexahydro[1,4]oxazino[3,4-h]pteridin-2-yl]phenyl)-3-methylurea

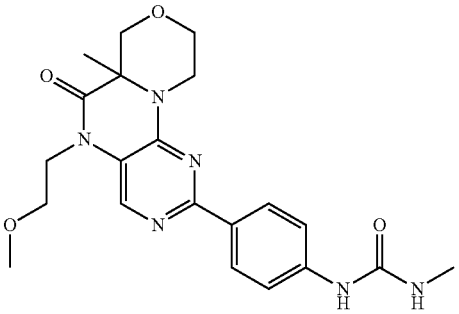

The title compound was prepared by method similar to Example 1, except the title compound was purified by preparative HPLC (eluting with a gradient of 15-40% ACN (containing 0.035% TFA) in water (containing 0.05% TFA) using a Sunfire Prep 5 μm C18, 75×30 mm column) to afford the title compound (22.5 mg, 0.053 mmol, 37% yield) as a white solid. $^1$H NMR (400 MHz, DMSO-$d_6$) δ ppm 1.33 (s, 3H) 2.66 (d, J=4.55 Hz, 3H) 3.19-3.33 (m, 4 H) 3.52-3.71 (m, 4H) 3.93-4.23 (m, 5H) 6.01-6.10 (m, 1H) 7.44-7.52 (m, 2H) 8.14-8.21 (m, 2H) 8.32 (s, 1H) 8.70 (s, 1H). MS [M+H] found 427.

EXAMPLE: 39

1-ethyl-3-(4-(5-(3-methoxypropyl)-6a-methyl-6-oxo-5,6,6a,7,9,10-hexahydro-[1,4]oxazino[3,4-h]pteridin-2-yl)phenyl)urea

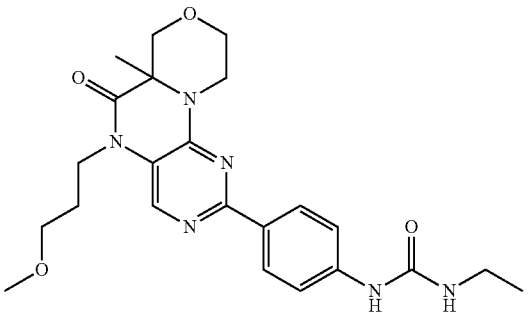

The title compound was prepared by method similar to Example 1, except the title compound was purified by preparative HPLC (eluting with a gradient of 20-45% ACN (containing 0.035% TFA) in water (containing 0.05% TFA) using a Sunfire Prep 5 μm C18, 75×30 mm column) to afford the title compound (40.8 mg, 0.090 mmol, 49.3% yield) as a white solid. $^1$H NMR (400 MHz, DMSO-$d_6$) δ ppm 1.06 (t, J=7.07 Hz, 3H) 1.34 (s, 3H) 1.75-1.87 (m, 2H) 3.06-3.18 (m, 2H) 3.18-3.30 (m, 4H) 3.38 (t, J=6.06 Hz, 2H) 3.52-3.63 (m, 1H) 3.67 (d, J=11.62 Hz, 1H) 3.85-4.10 (m, 4H) 4.13-4.24 (m, 1H) 6.15 (t, J=5.56 Hz, 1H) 7.47 (d, J=8.84 Hz, 2H) 8.17 (d, J=8.84 Hz, 2H) 8.23 (s, 1H) 8.61 (s, 1H). MS [M+H] found 455.

EXAMPLE: 40

1-cyclopropyl-3-(4-(5-(3-methoxypropyl)-6a-methyl-6-oxo-5,6,6a,7,9,10-hexahydro-[1,4]oxazino[3,4-h]pteridin-2-yl)phenyl)urea

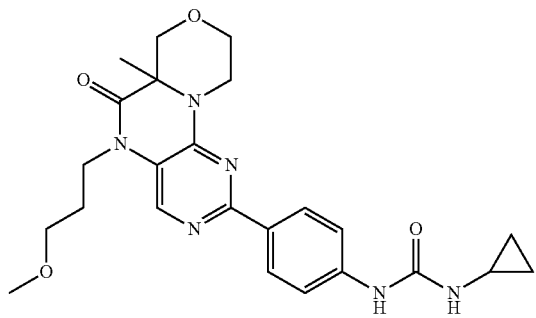

The title compound was prepared by method similar to Example 1, except the title compound was purified by preparative HPLC (eluting with a gradient of 20-45% ACN (containing 0.035% TFA) in water (containing 0.05% TFA) using a Sunfire Prep 5 μm C18, 75×30 mm column) to afford the title compound (37.1 mg, 0.080 mmol, 43% yield) as an off-white solid. $^1$H NMR (400 MHz, DMSO-$d_6$) δ ppm 0.41 (m, 2H) 0.64 (m, 2H) 1.34 (s, 3H) 1.75-1.87 (m, 2H) 2.51-2.61 (m, 1H) 3.19-3.29 (m, 4H) 3.38 (t, J=6.06 Hz, 2H) 3.52-3.63 (m, 1 H) 3.67 (d, J=11.62 Hz, 1H) 3.85-4.11 (m, 4H) 4.13-4.24 (m, 1H) 6.42 (d, J=2.78 Hz, 1H) 7.43-7.54 (m, 2H) 8.14-8.21 (m, 2H) 8.24 (s, 1H) 8.49 (s, 1H). MS [M+H] found 467.

EXAMPLE: 41

(S)-1-cyclopropyl-3-(4-(5-(3-methoxypropyl)-6a-methyl-6-oxo-5,6,6a,7,9,10-hexahydro-[1,4]oxazino[3,4-h]pteridin-2-yl)phenyl)urea and

EXAMPLE: 42

(R)-1-cyclopropyl-3-(4-(5-(3-methoxypropyl)-6a-methyl-6-oxo-5,6,6a,7,9,10-hexahydro-[1,4]oxazino[3,4-h]pteridin-2-yl)phenyl)urea

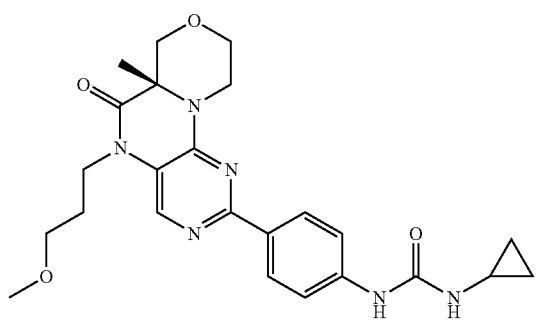

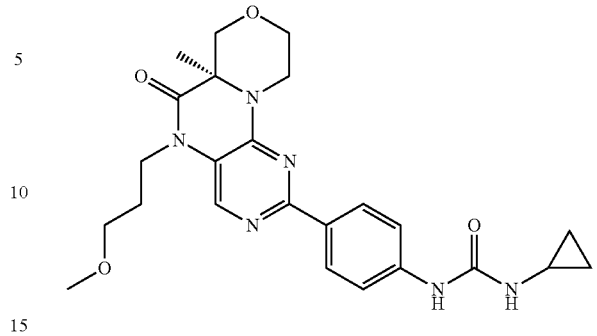

The product of 40 (26.9 mg) was separated by chiral SFC (Chiralpak AD-H column, flowrate=1.25 mL/min, modifier 40% methanol containing 10 mM NH$_4$OAc in liquid CO$_2$ to give Isomer 1 (12.1 mg, t=1.59 min) and Isomer 2 (12.5 mg, t=4.30 min).

EXAMPLE: 43

1-(4-(5-(2-ethoxyethyl)-6a-methyl-6-oxo-5,6,6a,7,9,10-hexahydro-[1,4]oxazino[3,4-h]pteridin-2-yl)phenyl)-3-methylurea

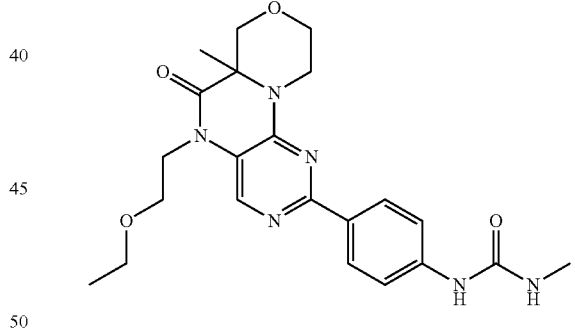

The title compound was prepared by method similar to Example 1, except the title compound was purified by preparative HPLC (eluting with a gradient of 15-40% ACN (containing 0.035% TFA) in water (containing 0.05% TFA) using a Sunfire Prep 5 μm C18, 75×30 mm column) to afford the title compound (43.9 mg, 0.100 mmol, 52.4% yield) as an off-white solid. $^1$H NMR (400 MHz, DMSO-$d_6$) δ ppm 1.04 (t, J=6.95 Hz, 3H) 1.33 (s, 3H) 2.66 (d, J=4.80 Hz, 3H) 3.18-3.32 (m, 1H) 3.36-3.50 (m, 2H) 3.51-3.71 (m, 4H) 3.94-4.29 (m, 5 H) 6.01-6.11 (m, 1H) 7.44-7.53 (m, 2H) 8.13-8.22 (m, 2H) 8.33 (s, 1H) 8.70 (s, 1H). MS [M+H] found 441.

EXAMPLE: 44

1-(4-(5-(2-hydroxy-2-methylpropyl)-6a-methyl-6-oxo-5,6,6a,7,9,10-hexahydro-[1,4]oxazino[3,4-h]pteridin-2-yl)phenyl)-3-methylurea

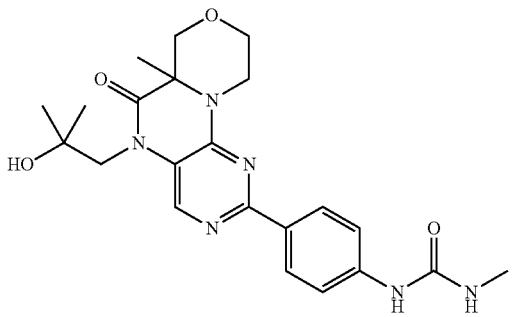

To a mixture of methyl 2-hydroxy-2-methylpropanoate (5.04 g, 42.7 mmol) and 3,4-dihydro-2H-pyran (5.85 ml, 64.0 mmol) in dichloromethane (40 ml) was added pyridine 4-methylbenzenesulfonate (0.536 g, 2.13 mmol) and the reaction mixture was stirred for 1.5 hours. The reaction mixture was poured into water and extracted with Et$_2$O. The organic layers were dried over Na$_2$SO$_4$ filtered, and concentrated in vacuo to give a crude oil. The crude residue was purified by silica gel chromatography (hexane/ethyl acetate, 100:0 to 17:3) to afford methyl 2-methyl-2-(tetrahydro-2H-pyran-2-yloxy)propanoate (7.30 g, 36.1 mmol, 85% yield) as a colorless oil. $^1$H NMR (400 MHz, DMSO-d$_6$) δ ppm 1.35 (s, 3H) 1.36-1.55 (m, 7H) 1.57-1.81 (m, 2H) 3.32-3.42 (m, 1H) 3.62 (s, 3H) 3.72-3.85 (m, 1H) 4.65-4.75 (m, 1H).

To a solution of methyl 2-methyl-2-(tetrahydro-2H-pyran-2-yloxy)propanoate (1.25 g, 6.16 mmol) in THF (20 ml) under nitrogen was added portionwise lithium aluminium hydride (0.246 g, 6.16 mmol) at 0° C. and the reaction mixture was stirred 2 h, followed by slow addition of Na$_2$SO$_4$.10H$_2$O (1.98 g, 6.16 mmol). After 30 minutes of stirring at 0° C. to room temperature, the insoluble materials were filtered off. The filtrate was concentrated in vacuo to give 2-methyl-2-(tetrahydro-2H-pyran-2-yloxy)propan-1-ol (1.16 g, 6.68 mmol, quant.) as a colorless oil which was used in the next step without further purification. $^1$H NMR (400 MHz, DMSO-d$_6$) δ ppm 1.11 (s, 6H) 1.29-1.62 (m, 5H) 1.67-1.80 (m, 1H) 3.19-3.31 (m, 2H) 3.34-3.43 (m, 1H) 3.77-3.88 (m, 1H) 4.40 (t, J=5.94 Hz, 1H) 4.75-4.81 (m, 1H).

To a suspension of 2-methyl-2-(tetrahydro-2H-pyran-2-yloxy)propan-1-ol (1.16 g, 6.68 mmol) in dichloromethane (20 ml) at 0° C. was added portionwise Dess-Martin periodinane (3.26 g, 7.68 mmol), and the reaction mixture was stirred at the same temperature for 20 minutes, followed by addition of saturated aqueous NaHCO$_3$ and Na$_2$S$_2$O$_3$. The resulting mixture was stirred for 3 hours and the reaction mixture was extracted with Et$_2$O. The combined organic phases were dried and concentrated in vacuo to give 2-methyl-2-(tetrahydro-2H-pyran-2-yloxy)propanal (958 mg, 5.56 mmol, 83% yield) as a colorless oil which was used in the next step without further purification. $^1$H NMR (400 MHz, DMSO-d$_6$) δ ppm 1.18 (s, 3H) 1.23 (s, 3 H) 1.33-1.85 (m, 6H) 3.32-3.44 (m, 1H) 3.73-3.89 (m, 1H) 4.61-4.70 (m, 1H) 9.44 (s, 1 H).

To a mixture of 2,4-dichloropyrimidin-5-amine (542 mg, 3.31 mmol) and 2-methyl-2-(tetrahydro-2H-pyran-2-yloxy)propanal (740 mg, 4.30 mmol) in dichloromethane (10 ml) at 0° C. was added dropwise a solution of titanium tetrachloride (0.401 ml, 3.64 mmol) in dichloromethane (4 ml). After the reaction mixture was stirred at room temperature for 2 hours. Sodium cyanoborohydride (656 mg, 9.92 mmol) was added portionwise and the reaction mixture was stirred at room temperature for 16 hours. After the reaction mixture was diluted with dichloromethane, the reaction mixture was poured carefully into NaHCO$_3$ aqueous solution. EtOAc was added and then the insoluble materials were filtered off. The phases of the filtrate were separated, and the aqueous phase was extracted with EtOAc. The combined organic phases were washed with water, dried and concentrated in vacuo to give a crude oil. The crude residue was purified by silica gel chromatography (hexane/ethyl acetate, 19:1 to 2:3) to afford 1-(2,4-dichloropyrimidin-5-ylamino)-2-methylpropan-2-ol (315 mg, 1.34 mmol, 40% yield) as a yellow oil. $^1$H NMR (400 MHz, DMSO-d$_6$) δ ppm 1.15 (s, 6H) 3.16 (d, J=6.32 Hz, 2H) 4.64 (s, 1H) 5.60-5.68 (m, 1H) 8.31 (s, 1H).

To a mixture of 1-(2,4-dichloropyrimidin-5-ylamino)-2-methylpropan-2-ol (258 mg, 1.09 mmol) and 3,4-dihydro-2H-pyran (0.200 ml, 2.18 mmol) in dichloromethane (7 ml) was added pyridine 4-methylbenzenesulfonate (13.7 mg, 0.055 mmol) and the reaction mixture was stirred for 16 hours. The reaction mixture was poured into water and extracted with Et$_2$O. The organic layers were dried over Na$_2$SO$_4$, filtered and concentrated in vacuo to give a crude oil. The crude residue was purified by silica gel chromatography (hexane/ethyl acetate, 100:0 to 3:1) to afford 2,4-dichloro-N-(2-methyl-2-(tetrahydro-2H-pyran-2-yloxy)propyl)pyrimidin-5-amine (315 mg, 0.982 mmol, 90% yield) as a pale yellow oil. $^1$H NMR (400 MHz, DMSO-d$_6$) δ ppm 1.18 (s, 3H) 1.23 (s, 3H) 1.25-1.75 (m, 6H) 3.27-3.32 (m, 2H) 3.37-3.49 (m, 1H) 3.69-3.83 (m, 1H) 4.74-4.86 (m, 1H) 5.75 (t, J=6.32 Hz, 1H) 8.36 (s, 1H).

To a mixture of 2,4-dichloro-N-(2-methyl-2-(tetrahydro-2H-pyran-2-yloxy)propyl)pyrimidin-5-amine (315 mg, 0.982 mmol) and morpholine-3-carboxylic acid hydrochloride (247 mg, 1.47 mmol) in DMSO (6 ml) was added diisopropylethylamine (0.686 ml, 3.93 mmol), and the reaction mixture was stirred at 95° C. for 4 hours. The reaction mixture was poured into water and extracted with EtOAc. The organic layers were dried over Na$_2$SO$_4$, filtered and concentrated in vacuo to give a crude oil. The crude residue was chromatographed by silica gel (hexane/ethyl acetate, 19:1 to 1:1) to afford 2-chloro-5-2-methyl-2-(tetrahydro-2H-pyran-2-yloxy)propyl)-6a,7,9,10-tetrahydro-[1,4]oxazino[3,4-h]pteridin-6(5H)-one (96.2 mg, 0.242 mmol, 25% yield) as a pale yellow oil which was used in the next reaction without further purification. MS [M+H] found 397.

To a mixture of 2-chloro-5-(2-methyl-2-(tetrahydro-2H-pyran-2-yloxy)propyl)-6a,7,9,10-tetrahydro-[1,3,4-h]pteridin-6(5H)-one (96.2 mg, 0.242 mmol) and iodomethane (0.076 ml, 1.21 mmol) in DMSO (4 ml) at 0° C. was added sodium 2-methylpropan-2-olate (46.6 mg, 0.485 mmol). The ice-bath was removed and the reaction mixture was stirred at room temperature for 16 h, followed by being poured into water. Extraction with EtOAc, washing with water, drying and concentration in vacuo gave crude 2-chloro-6a-methyl-5-(2-methyl-2-(tetrahydro-2H-pyran-2-yloxy)propyl)-6a,7,9,10-tetrahydro-[1,4]oxazino[3,4-h]pteridin-6(5H)-one (133 mg, 0.322 mmol) as a red oil which was used without further purification. MS [M+H] found 411.

To a solution of 2-chloro-6a-methyl-5-(2-methyl-2-(tetrahydro-2H-pyran-2-yloxy)propyl)-6a,7,9,10-tetrahydro-[1,4]oxazino[3,4-h]pteridin-6(5H)-one (133 mg, 0.322 mmol) in THF (3 ml) was added 1 N HCl aqueous solution (1 ml, 1.000 mmol) and the reaction mixture was stirred for 1 h, followed by being poured into NaHCO₃ aqueous solution. Extraction with EtOAc, drying over Na₂SO₄ and concentration in vacuo gave crude 2-chloro-5-(2-hydroxy-2-methylpropyl)-6a-methyl-6a,7,9,10-tetrahydro-[1,4]oxazino[3,4-h]pteridin-6(5H)-one (84.9 mg, 0.260 mmol, 81% yield) as a yellow oil which was used in the next step without further purification. MS [M+H] found 327.

A mixture of 2-chloro-5-(2-hydroxy-2-methylpropyl)-6a-methyl-6a,7,9,10-tetrahydro-[1,4]oxazino[3,4-h]pteridin-6 (5H)-one (84.9 mg, 0.260 mmol), 1-methyl-3-[4-(4,4,5,5-tetramethyl-1,3,2-dioxaborolane-2-yl)phenyl]-urea (143 mg, 0.520 mmol), saturated aqueous NaHCO₃ (1 ml) and PdCl₂(dppf) (17.0 mg, 0.021 mmol) in 1,4-dioxane (2 ml) was irradiated in the microwave at 110° C. for 30 minutes The reaction mixture was diluted with THF and passed through 0.45 µM PTFE syringe filter (washed with small amount of MeOH). The filtrate was purified by preparative HPLC (eluting with a gradient of 20-20% ACN (containing 0.035% TFA) in water (containing 0.05% TFA) using a Sunfire Prep 5 µm C18, 75×30 mm column). The fractions containing the desired product were combined and were evaporated under reduced pressure. Then NaHCO₃ aqueous solution was added (in order to adjust the pH to basic) and extracted with EtOAc. The combined organic phases were dried over Na₂SO₄, filtered and concentrated in vacuo to afford a crude solid. The solid was triturated with hexane/ethyl acetate (3:1), collected by filtration, rinsed with hexane/ethyl acetate (3:1) and dried to afford the title compound (21.1 mg, 0.048 mmol, 18.4% yield) as a pale beige solid. ¹H NMR (400 MHz, DMSO-d₆) δ ppm 1.14 (s, 3H) 1.15 (s, 3H) 1.35 (s, 3H) 2.66 (d, J=4.55 Hz, 3H) 3.19-3.33 (m, 1H) 3.52-3.80 (m, 3H) 3.94-4.11 (m, 3H) 4.12-4.22 (m, 1H) 4.67 (s, 1H) 6.00-6.10 (m, 1H) 7.48 (d, J=8.84 Hz, 2H) 8.17 (d, J=8.84 Hz, 2H) 8.58 (s, 1H) 8.68 (s, 1H). MS [M+H] found 441.

EXAMPLE: 45

1-cyclopropyl-3-(4-[5-(1,1-dioxidotetrahydro-2H-thiopyran-4-yl)-6a-methyl-6-oxo-5,6,6a,7,9,10-hexahydro[1,4]oxazino[3,4-h]pteridin-2-yl]phenyl) urea

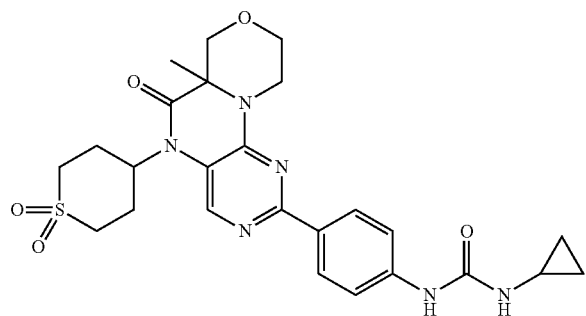

To a mixture of 2,4-dichloropyrimidin-5-amine (1.58 g, 9.63 mmol) and dihydro-2H-thiopyran-4 (3H)-one (1.45 g, 12.5 mmol) in dichloromethane (50 ml) at 0° C. was added dropwise a 1 M solution of titanium tetrachloride (10.6 ml, 10.6 mmol) in dichloromethane. After the reaction mixture was stirred at room temperature for 2 h, sodium cyanoborohydride (1.91 g, 28.9 mmol) was added in single portion and the reaction mixture was stirred at room temperature for 16 hours. After the reaction mixture was diluted with dichloromethane, the reaction mixture was poured carefully into iced-saturated NaHCO₃ solution. EtOAc was added and then the insoluble materials were filtered off. The phases of the filtrate were separated, and the aqueous phase was extracted with EtOAc. The combined organic phases were washed with water and saturated NaCl, dried with Na₂SO₄ and concentrated in vacuo to give a crude oil. The crude residue was purified by silica gel chromatography (hexane/ethyl acetate, 100:0 to 3:1) to afford 2,4-dichloro-N-(tetrahydro-2H-thiopyran-4-yl)pyrimidin-5-amine (864 mg, 3.27 mmol, 34% yield) as a yellow oil. ¹H NMR (400 MHz, DMSO-d₆) δ ppm 1.59-1.76 (m, 2H) 2.07-2.20 (m, 2H) 2.58-2.69 (m, 2H) 2.70-2.85 (m, 2H) 3.42-3.57 (m, 1H) 5.78 (d, J=8.84 Hz, 1H) 8.25 (s, 1H). MS [M+H] 264.

To a mixture of 2,4-dichloro-N-(tetrahydro-2H-thiopyran-4-yl)pyrimidin-5-amine (864 mg, 3.27 mmol) and morpholine-3-carboxylic acid hydrochloride (822 mg, 4.91 mmol) in DMSO (15 ml) was added diisopropylethylamine (2.29 ml, 13.1 mmol), and the reaction mixture was stirred at 95° C. for 4 hours. The reaction mixture was poured into water and extracted with EtOAc. The organic layers were dried over Na₂SO₄, filtered and concentrated in vacuo to give a crude solid. The solid was chromatographed by silica gel (hexane/ethyl acetate, 19:1 to 3:2) to afford partially purified 2-chloro-5-(tetrahydro-2H-thiopyran-4-yl)-6a,7,9,10-tetrahydro-[1,4]oxazino[3,4-h]pteridin-6(5H)-one (83.6 mg, 0.245 mmol, 7.5% yield) as a white solid. MS [M+H] found 341.

To a mixture of 2-chloro-5-(tetrahydro-2H-thiopyran-4-yl)-6a,7,9,10-tetrahydro-[1,4]oxazino[3,4-h]pteridin-6(5H)-one (83.6 mg, 0.245 mmol) and iodomethane (0.077 ml, 1.226 mmol) in DMSO (3 ml) at 0° C. was added sodium 2-methylpropan-2-olate (47.1 mg, 0.491 mmol). The ice-bath was removed and the reaction mixture was stirred at room temperature for 16 hours. The reaction mixture was poured into water and extracted with EtOAc. The organic layers were washed with water (containing Na₂S₂O₃), dried and concentrated in vacuo to give a crude oil. The crude residue was purified by silica gel chromatography (hexane/ethyl acetate, 19:1 to 1:1) to afford 2-chloro-6a-methyl-5-(tetrahydro-2H-thiopyran-4-yl)-6a,7,9,10-tetrahydro-[1,4]oxazino[3,4-h]pteridin-6(5H)-one (9.4 mg, 0.026 mmol, 11% yield) as a colorless oil. MS [M+H] found 355.

To a solution of 2-chloro-6a-methyl-5-(tetrahydro-2H-thiopyran-4-yl)-6a,7,9,10-tetrahydro-[1,4]oxazino[3,4-h]pteridin-6(5H)-one (9.4 mg, 0.026 mmol) in MeOH (1 ml) at 0° C. was added dropwise a solution of oxone (40.7 mg, 0.066 mmol) in water (1 ml), and the reaction mixture was stirred at room temperature for 16 h, followed by solvent removal in vacuo. The residue was partitioned between EtOAc and water. The phases were separated and the aqueous phase was extracted with EtOAc. The combined organic phases were dried and concentrated in vacuo to give 2-chloro-5-(1,1-dioxidotetrahydro-2H-thiopyran-4-yl)-6a-methyl-6a,7,9,10-tetrahydro[1,4]oxazino[3,4-h]pteridin-6(5H)-one (6.5 mg, 0.017 mmol, 63% yield) as a white solid. This was used in the next step without further purification. MS [M+H] found 387.

A mixture of 2-chloro-5-(1,1-dioxidotetrahydro-2H-thiopyran-4-yl)-6a-methyl-6a,7,9,10-tetrahydro[1,4]oxazino[3,4-h]pteridin-6(5H)-one (6.50 mg, 0.017 mmol), 1-cyclopropyl-3-(4-(4,4,5,5-tetramethyl-1,3,2-dioxaborolan-2-yl) phenyl)urea (8.63 mg, 0.029 mmol), saturated aqueous NaHCO₃ (0.75 ml) and PdCl₂(dppf) (1.10 mg, 1.34 µmol) in 1,4-dioxane (1 ml) was irradiated in the microwave at 110° C. for 30 minutes The reaction mixture was diluted with THF and passed through 0.45 mM PTFE syringe filter (washed with small amount of THF). The filtrate was purified by preparative HPLC (eluting with a gradient of 15-40% ACN (containing 0.035% TFA) in water (containing 0.05% TFA)

using a Sunfire Prep 5 μm C18, 75×30 mm column). The fractions containing the desired product were combined and were evaporated under reduced pressure. Then NaHCO$_3$ aqueous solution was added (in order to adjust the pH to basic) and extracted with EtOAc. The combined organic phases were dried over Na$_2$SO$_4$, filtered and concentrated in vacuo to afford the title compound (6.2 mg, 0.012 mmol, 70% yield) as a white solid. $^1$H NMR (400 MHz, DMSO-d$_6$) d ppm 0.36-0.45 (m, 2H) 0.59-0.69 (m, 2H) 1.32 (s, 3H) 1.93-2.17 (m, 2H) 2.51-2.60 (m, 1H) 2.85-3.76 (m, 9H) 3.91-3.99 (m, 1H) 4.01-4.10 (m, 1H) 4.14-4.25 (m, 1H) 4.45-4.62 (m, 1H) 6.58 (br. s., 1H) 7.49-7.56 (m, 2H) 8.16-8.24 (m, 2H) 8.49 (s, 1H) 8.75 (s, 1H). MS [M+H] found 527.

EXAMPLE: 46

1-cyclopropyl-3-(4-(6a-methyl-5-(3-(methylsulfonyl) propyl)-6-oxo-5,6,6a,7,9,10-hexahydro-[1,4]oxazino [3,4-h]pteridin-2-yl)phenyl)urea

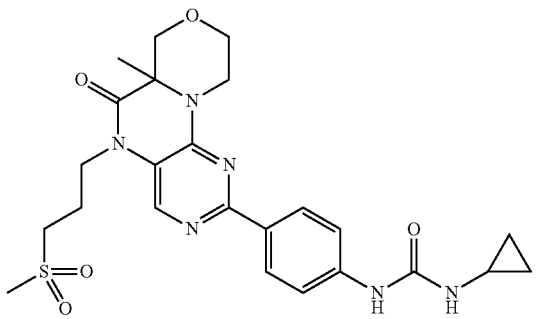

The title compound was prepared by method similar to Example 1 using 3-(methylsulfonyl)propyl-4-methylbenzenesulfonate, except the title compound was purified by preparative HPLC (eluting with a gradient of 15-40% ACN (containing 0.035% TFA) in water (containing 0.05% TFA) using a Sunfire Prep 5 μm C18, 75×30 mm column) to afford the title compound (38.9 mg, 0.076 mmol, 32% yield) as a white solid. $^1$H NMR (400 MHz, DMSO-d$_6$) δ ppm 0.37-0.46 (m, 2H) 0.60-0.69 (m, 2H) 1.37 (s, 3H) 1.91-2.05 (m, 2H) 2.47-2.59 (m, 1H) 3.00 (s, 3H) 3.19-3.34 (m, 3H) 3.52-3.64 (m, 1H) 3.71 (d, J=11.37 Hz, 1H) 3.92-4.12 (m, 4H) 4.15-4.26 (m, 1H) 6.46 (d, J=2.53 Hz, 1H) 7.45-7.55 (m, 2H) 8.15-8.24 (m, 2H) 8.33 (s, 1H) 8.54 (s, 1H). MS [M+H] found 515.

EXAMPLE: 47

1-cyclopropyl-3-(4-(5-(2,2-difluoropropyl)-6a-methyl-6-oxo-5,6,6a,7,9,10-hexahydro-[1,4]oxazino[3,4-h]pteridin-2-yl)phenyl)urea

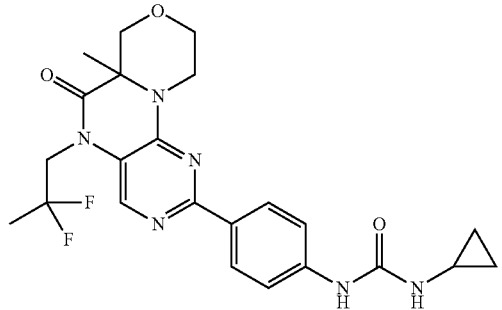

To a mixture of 2-chloro-6a,7,9,10-tetrahydro-[1,4]oxazino[3,4-h]pteridin-6(5H)-one (822 mg, 3.42 mmol), chloroacetone (0.429 ml, 5.12 mmol) in DMF (10 ml) was added K$_2$CO$_3$ (1.42 g, 10.3 mmol) and the reaction mixture was stirred at room temperature for 2 days. The reaction mixture was poured into water and extracted with EtOAc. The organic layers were washed with water and saturated aqueous NaCl, dried and concentrated in vacuo to give a crude solid. The crude residue was triturated with hexane/ethyl acetate (3:1), collected by filtration, rinsed with hexane/ethyl acetate (3:1) and dried to afford 2-chloro-5-(2-oxopropyl)-6a,7,9,10-tetrahydro-[1,4]oxazino[3,4-h]pteridin-6(5H)-one (737 mg, 2.48 mmol, 73% yield) as a pale brown solid. MS [M+H] found 297.

To a solution of 2-chloro-5-(2-oxopropyl)-6a,7,9,10-tetrahydro-[1,4]oxazino[3,4-h]pteridin-6(5H)-one (736 mg, 2.48 mmol) in dichloromethane (15 ml) at 0° C. was added dropwise a solution of DAST (0.984 ml, 7.45 mmol) in dichloromethane (3 ml), and the reaction mixture was stirred at room temperature for 1 hour. Additional DAST (0.984 ml, 7.45 mmol) was added and the reaction mixture was stirred for 5 hours. Additional DAST (1.97 ml, 14.9 mmol) was added and the reaction mixture was stirred for 3 hours. Further DAST (3.94 ml, 29.8 mmol) was added and the reaction mixture was stirred for 16 hours. After the reaction mixture was cooled to 0° C., saturated aqueous NaHCO$_3$ was carefully added. The resulting mixture was stirred for 15 minutes and then extracted with EtOAc. The combined organic phases were washed with water, dried over Na$_2$SO$_4$, filtered and concentrated in vacuo to give a crude solid. The solid was purified by silica gel chromatography (hexane/ethyl acetate, 19:1 to 2:3) to afford 2-chloro-5-(2,2-difluoropropyl)-6a,7,9,10-tetrahydro-[1,4]oxazino[3,4-h]pteridin-6(5H)-one (466 mg, 1.46 mmol, 59% yield) as a white solid. MS [M+H] found 319.

To a mixture of 2-chloro-5-(2,2-difluoropropyl)-6a,7,9,10-tetrahydro-[1,4]oxazino[3,4-h]pteridin-6(5H)-one (466 mg, 1.46 mmol) and iodomethane (0.365 ml, 5.84 mmol) in DMSO (8 ml) at 0° C. was added sodium 2-methylpropan-2-olate (211 mg, 2.19 mmol). The ice-bath was removed and the reaction mixture was stirred at room temperature for 16 hours. The reaction mixture was poured into water and extracted with EtOAc. The organic layers were washed with water (containing Na$_2$S$_2$O$_3$), dried and concentrated in vacuo to give a crude solid. The solid was purified by silica gel chromatography (hexane/ethyl acetate, 19:1 to 2:1) to afford 2-chloro-5-(2,2-difluoropropyl)-6a-methyl-6a,7,9,10-tetrahydro-[1,4]oxazino[3,4-h]pteridin-6(5H)-one (264 mg, 0.793 mmol, 54% yield) as a white solid. MS [M+H] found 333.

A mixture of 2-chloro-5-(2,2-difluoropropyl)-6a-methyl-6a,7,9,10-tetrahydro-[1,4]oxazino[3,4-h]pteridin-6(5H)-one (260 mg, 0.782 mmol), 1-cyclopropyl-3-(4-(4,4,5,5-tetramethyl-1,3,2-dioxaborolan-2-yl)phenyl)urea (402 mg, 1.33 mmol), saturated aqueous NaHCO$_3$ (2 ml) and PdCl$_2$(dppf) (51.1 mg, 0.063 mmol) in 1,4-dioxane (5 ml) was irradiated in the microwave at 110° C. for 30 minutes The reaction mixture was diluted with THF and passed through 0.45 μM PTFE syringe filter (washed with small amount of THF). The filtrate was purified by preparative HPLC (eluting with a gradient of 20-45% ACN (containing 0.035% TFA) in water (containing 0.05% TFA) using a Sunfire Prep 5 μm C18, 75×30 mm column). The fractions containing the desired product were combined and were evaporated under reduced pressure. Then NaHCO$_3$ aqueous solution was added (in order to adjust the pH to basic) and extracted with EtOAc (THF was added to dissolve the precipitate). The combined organic phases were dried over Na₂SO₄, filtered and concentrated in vacuo to afford the title compound (164 mg, 0.347 mmol, 44% yield) as an off-white solid. ¹H NMR (400 MHz, DMSO-d₆) δ ppm 0.35-0.45 (m, 2H) 0.58-0.71 (m, 2H) 1.36 (s, 3H) 1.70 (t, J=19.20 Hz, 3H) 2.50-2.61 (m, 1H) 3.19-3.31 (m, 1H) 3.53-3.73 (m, 2H) 3.94-4.11 (m, 2H) 4.12-4.25 (m, 1H) 4.34-4.52 (m, 1H) 4.52-4.70 (m, 1H) 6.46 (d, J=2.53 Hz, 1H) 7.45-7.55 (m, 2H) 8.14-8.23 (m, 2H) 8.39 (s, 1H) 8.54 (s, 1H). MS [M+H] found 473.

EXAMPLE: 48

(S)-1-cyclopropyl-3-(4-(5-(2,2-difluoropropyl)-6a-methyl-6-oxo-5,6,6a,7,9,10-hexahydro-[1,4]oxazino[3,4-h]pteridin-2-yl)phenyl)urea and

EXAMPLE: 49

(S)-1-cyclopropyl-3-(4-(5-(2,2-difluoropropyl)-6a-methyl-6-oxo-5,6,6a,7,9,10-hexahydro-[1,4]oxazino[3,4-h]pteridin-2-yl)phenyl)urea and

EXAMPLE: 50

(R)-1-cyclopropyl-3-(4-(5-(2,2-difluoropropyl)-6a-methyl-6-oxo-5,6,6a,7,9,10-hexahydro-[1,4]oxazino[3,4-h]pteridin-2-yl)phenyl)urea

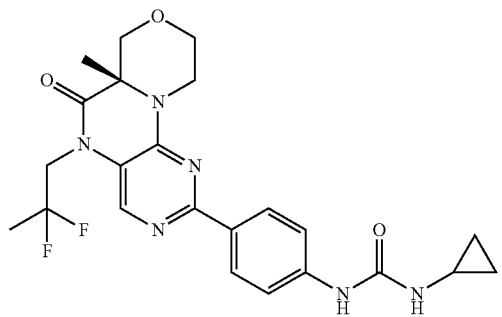

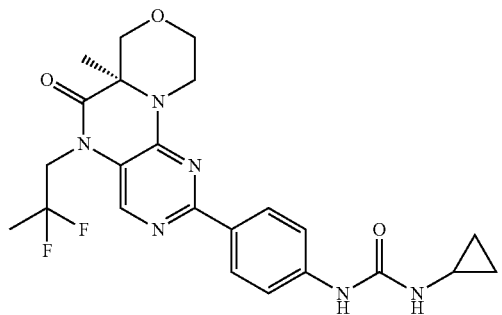

The product of Example 47 (164 mg) was separated by chiral SFC (Chiralpak AD-H column, flowrate=1.25 mL/min, modifier 23% 1-propanol containing 10 mM NH₄OAc in liquid CO₂ to give Isomer 1 (68.0 mg, t=2.54 min) and Isomer 2 (62.3 mg, t=3.49 min).

EXAMPLE: 51

1-cyclopropyl-3-(4-(6a-methyl-6-oxo-5-(2,2,2-trifluoroethyl)-5,6,6a,7,9,10-hexahydro-[1,4]oxazino[3,4-h]pteridin-2-yl)phenyl)urea

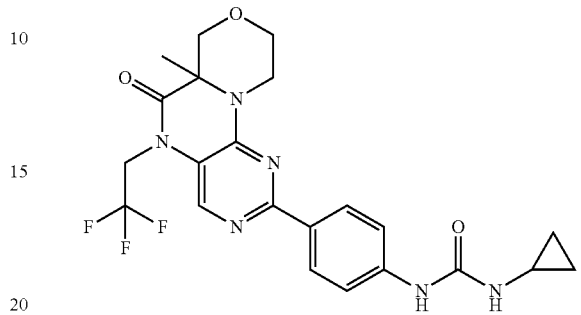

To a solution of 2-chloro-6a,7,9,10-tetrahydro-[1,4]oxazino[3,4-h]pteridin-6(5H)-one (363 mg, 1.509 mmol) in DMF (6 ml) at 0° C. was added NaH (72.4 mg, 1.81 mmol). After 15 minutes of stirring at 0° C., a solution of 2,2,2-trifluoroethyl trifluoromethanesulfonate (525 mg, 2.26 mmol) in DMF (1 ml) was slowly added. The reaction mixture was stirred at room temperature for 1.5 hours. The reaction mixture was poured into water and extracted with EtOAc. The organic layers were washed with water, dried over Na₂SO₄ and concentrated in vacuo to give a crude oil. The crude residue was purified by silica gel chromatography (hexane/ethyl acetate, 19:1 to 1:1) to afford 2-chloro-5-(2,2,2-trifluoroethyl)-6a,7,9,10-tetrahydro-[1,4]oxazino[3,4-h]pteridin-6(5H)-one (373 mg, 1.16 mmol, 77% yield) as a yellow solid. MS [M+H] found 323.

To a mixture of 2-chloro-5-(2,2,2-trifluoroethyl)-6a,7,9,10-tetrahydro-[1,4]oxazino[3,4-h]pteridin-6(5H)-one (768 mg, 2.38 mmol) and iodomethane (0.595 ml, 9.52 mmol) in DMSO (15 ml) at 0° C. was added sodium 2-methylpropan-2-olate (343 mg, 3.57 mmol). The ice-bath was removed and the reaction mixture was stirred at room temperature for 16 hours. The reaction mixture was poured into water and extracted with EtOAc. The organic layers were washed with water (containing Na₂S₂O₃), dried and concentrated in vacuo to give a crude oil. The crude residue was purified by silica gel chromatography (hexane/ethyl acetate, 19:1 to 11:9) to afford 2-chloro-6a-methyl-5-(2,2,2-trifluoroethyl)-6a,7,9,10-tetrahydro-[1,4]oxazino[3,4-h]pteridin-6(5H)-one (191 mg, 0.566 mmol, 24% yield) as a white solid. ¹H NMR (400 MHz, DMSO-d₆) δ ppm 1.41 (s, 3H) 3.17-3.28 (m, 1H) 3.55 (td, J=12.13, 3.03 Hz, 1H) 3.68 (d, J=11.62 Hz, 1H) 3.89-4.07 (m, 3H) 4.75-5.04 (m, 2H) 8.31 (s, 1H). MS [M+H] found 337.

A mixture of 2-chloro-6a-methyl-5-(2,2,2-trifluoroethyl)-6a,7,9,10-tetrahydro-[1,4]oxazino[3,4-h]pteridin-6(5H)-one (292 mg, 0.868 mmol), 1-cyclopropyl-3-(4-(4,4,5,5-tetramethyl-1,3,2-dioxaborolan-2-yl)phenyl)urea (446 mg, 1.48 mmol), saturated aqueous NaHCO₃ (2 ml) and PdCl₂(dppf) (56.7 mg, 0.069 mmol) in 1,4-dioxane (4 ml) was irradiated in microwave at 110° C. for 30 minutes The reaction mixture was diluted with THF and passed through 0.45 μM PTFE syringe filter (washed with small amount of THF). The filtrate was purified by preparative HPLC (eluting with a gradient of 25-50% ACN (containing 0.035% TFA) in water (containing 0.05% TFA) using a Sunfire Prep 5 μm C18, 75×30 mm column). The fractions containing the desired product were combined and were evaporated under reduced pressure. Then NaHCO$_3$ aqueous solution was added (in order to adjust the pH to basic) and extracted with EtOAc (THF was added to dissolve the precipitate). The combined organic phases were dried over Na$_2$SO$_4$, filtered and concentrated in vacuo to afford the title compound (206 mg, 0.432 mmol, 50% yield) as a white solid. $^1$H NMR (400 MHz, DMSO-d$_6$) ppm 0.37-0.45 (m, 2H) 0.59-0.69 (m, 2H) 1.37 (s, 3H) 2.51-2.60 (m, 1H) 3.22-3.33 (m, 1H) 3.55-3.73 (m, 2H) 3.98-4.11 (m, 2H) 4.15-4.24 (m, 1H) 4.80-4.94 (m, 1H) 4.94-5.11 (m, 1H) 6.43-6.50 (m, 1H) 7.46-7.54 (m, 2H) 8.15-8.23 (m, 2H) 8.47 (s, 1H) 8.56 (s, 1H). MS [M+H] found 477.

EXAMPLE: 52

(S)-1-cyclopropyl-3-(4-(6a-methyl-6-oxo-5-(2,2,2-trifluoroethyl)-5,6,6a,7,9,10-hexahydro-[1,4]oxazino[3,4-h]pteridin-2-yl)phenyl)urea and

EXAMPLE: 53

(R)-1-cyclopropyl-3-(4-(6a-methyl-6-oxo-5-(2,2,2-trifluoroethyl)-5,6,6a,7,9,10-hexahydro-[1,4]oxazino[3,4-h]pteridin-2-yl)phenyl)urea

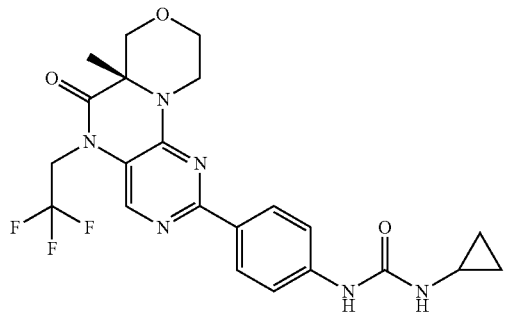

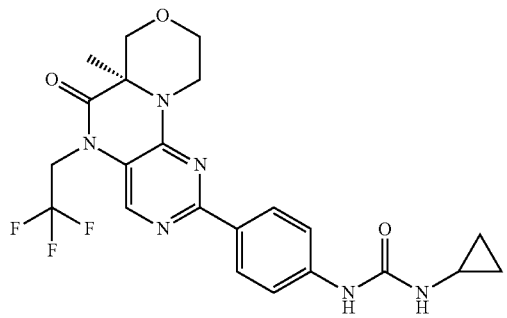

The product of 51 (195 mg) was separated by chiral SFC (Chiralpak AD-H column, flowrate=1.25 mL/min, modifier 40% ethanol in liquid CO$_2$ to give Isomer 1 (57.6 mg, t=1.21 min) and Isomer 2 (64.2 mg, t=2.07 min).

EXAMPLE 54

1-cyclopropyl-3-(4-(6a-methyl-6-oxo-5-((tetrahydrofuran-3-yl)methyl)-5,6,6a,7,9,10-hexahydro-[1,4]oxazino[3,4-h]pteridin-2-yl)phenyl)urea

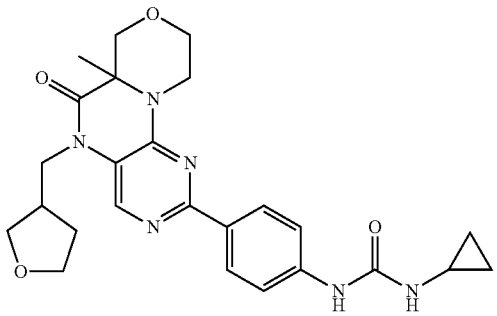

To 2,4-dichloropyrimidin-5-amine (6.22 g, 38.0 mmol) in 16.5 mL of dichloromethane was added dry tetrahydrofuran-3-carbaldehyde (3.8 g, 38.0 mmol). The solution was cooled to 0° C. A solution of titanium tetrachloride (41.8 ml, 41.8 mmol) in 10 mL of dichloromethane was added slowly. The reaction mixture was stirred at for 2 hours. Sodium triacetoxyborohydride (24.13 g, 114 mmol) was added in 4 equal portions over about 10 minutes and the mixture was stirred at room temperature for 48 hours. The reaction mixture was then diluted with water and extracted twice with methyl-t-butyl ether. The organic layers were combined, dried over magnesium sulfate, filtered, and evaporated in vacuo to give 8.2 g of 2,4-dichloro-N-((tetrahydrofuran-3-yl)methyl)pyrimidin-5-amine as a tan solid which was used without further purification. [M+H] found 249.

2,4-Dichloro-N-((tetrahydrofuran-3-yl)methyl)pyrimidin-5-amine (7 g, 28.2 mmol), morpholine-3-carboxylic acid hydrochloride (832 mg, 4.97 mmol), and DIPEA (2.67 ml, 15.28 mmol) were combined in DMSO (8 ml). The reaction mixture was heated overnight at 100° C. Upon cooling the solution was diluted with water then extracted twice with ethyl acetate. The organic layers were combined, dried over magnesium sulfate, filtered, and evaporated in vacuo to give 6.6 g of 2-chloro-5-((tetrahydrofuran-3-yl)methyl)-6a,7,9,10-tetrahydro-[1,4]oxazino[3,4-h]pteridin-6(5H)-one as a brown oil which was used without further purification. [M+H] found 325.

2-Chloro-5-((tetrahydrofuran-3-yl)methyl)-6a,7,9,10-tetrahydro-[1,4]oxazino[3,4-h]pteridin-6(5H)-one (320 mg, 0.985 mmol) and iodomethane (0.307 ml, 4.93 mmol) were frozen in DMSO (2 ml). Sodium 2-methylpropan-2-olate (284 mg, 2.96 mmol) was added and covered by a layer of DMSO. The mixture was allowed to warm to room temperature and stir for 1 hour, then was diluted with water then extracted twice with EtOAc. The organic layers were combined, dried over magnesium sulfate, filtered, and evaporated in vacuo to give 390 mg of 2-chloro-6a-methyl-5-((tetrahydrofuran-3-yl)methyl)-6a,7,9,10-tetrahydro-[1,4]oxazino[3,4-h]pteridin-6(5H)-one as a tan oil. [M+H] found 339.

2-Chloro-6a-methyl-5-((tetrahydrofuran-3-yl)methyl)-6a,7,9,10-tetrahydro-[1,4]oxazino[3,4-h]pteridin-6(5H)-one (390 mg, 1.151 mmol) PdCl$_2$(dppf)-CH$_2$Cl$_2$ (188 mg, 0.230 mmol), 1-cyclopropyl-3-(4-(4,4,5,5-tetramethyl-1,3,2-dioxaborolan-2-yl)phenyl)urea (417 mg, 1.381 mmol) and sodium 2-methylpropan-2-olate (1.5 ml, 1.151 mmol) were combined in 1,4-dioxane (3 ml). The suspension was heated by microwave irradiation at 100° C. for 30 minutes, the reaction was filtered, cooled, and purified by mass-triggered preparative HPLC using 22-25% ACN (containing 0.035% TFA) in water (containing 0.05% TFA) on a Phenomenex Gemini 5 μm C18, 75×30 mm column). Product containing fractions were evaporated in vacuo to give a residue. The residue was dissolved in methanol for transfer. The solvent was removed under a stream of nitrogen gas to give 85 mg of the title compound as a pale yellow solid. $^1$H NMR (400 MHz, MeOD) δ ppm 0.48-0.57 (m, 2H) 0.71-0.79 (m, 2H) 1.73 (s, 3H) 1.73 (m, 1H) 2.02-2.14 (m, 1H) 2.61 (m, 1H) 2.68-2.80 (m, 1H) 3.55-3.65 (m, 2H) 3.68 (dd, J=12, 4 Hz, 1H) 3.71-3.81 (m, 3H) 3.84 (d, J=12 Hz, 2H) 3.91-4.05 (m, 2H) 4.08-4.21 (m, 2H) 4.75 (d, J=16 Hz, 1H) 7.67 (d, J=8 Hz, 2H) 8.03 (s, 1H) 8.11 (dd, J=8, 4 Hz, 2 H) [M+H] found 479.

EXAMPLE 55

(S,S)-1-cyclopropyl-3-(4-(6a-methyl-6-oxo-5-((tetrahydrofuran-3-yl)methyl)-5,6,6a,7,9,10-hexahydro-[1,4]oxazino[3,4-h]pteridin-2-yl)phenyl)urea

EXAMPLE 56

(S,R)-1-cyclopropyl-3-(4-(6a-methyl-6-oxo-5-((tetrahydro furan-3-yl)methyl)-5,6,6a,7,9,10-hexahydro-[1,4]oxazino[3,4-h]pteridin-2-yl)phenyl)urea

EXAMPLE 57

(R,S)-1-cyclopropyl-3-(4-(6a-methyl-6-oxo-5-((tetrahydro furan-3-yl)methyl)-5,6,6a,7,9,10-hexahydro-[1,4]oxazino[3,4-h]pteridin-2-yl)phenyl)urea and

EXAMPLE 58

(R,R)-1-cyclopropyl-3-(4-(6a-methyl-6-oxo-5-((tetrahydro furan-3-yl)methyl)-5,6,6a,7,9,10-hexahydro-[1,4]oxazino[3,4-h]pteridin-2-yl)phenyl)urea

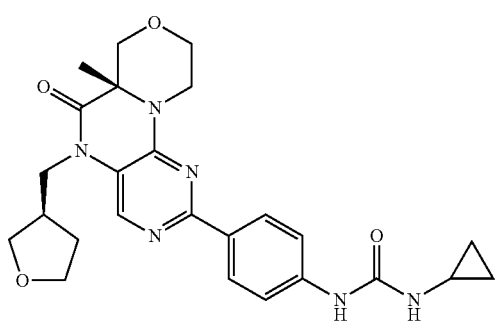

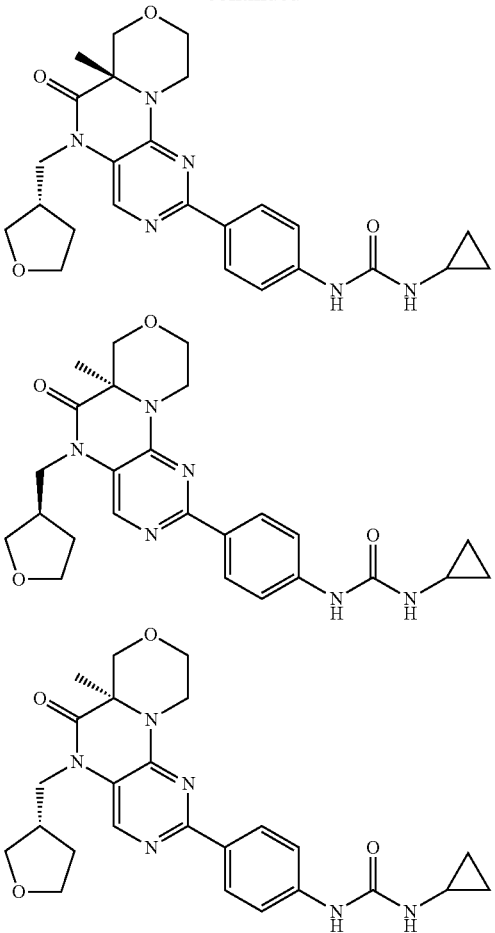

Cyclopropyl-3-(4-(6a-methyl-6-oxo-5-((tetrahydrofuran-3-yl)methyl)-5,6,6a,7,9,10-hexahydro-[1,4]oxazino[3,4-h]pteridin-2-yl)phenyl)urea as prepared in Example 54 was chirally separated by HPLC (Chiralpak AD-H column, flow-rate=50 mL/min, eluting with 35% methanol in DCM) to give: Isomer 1: $^1$H NMR (400 MHz, MeOD) δ ppm 0.48-0.56 (m, 2H) 0.70-0.82 (m, 2H) 1.45 (s, 3H) 1.75 (m, 1H) 1.96-2.13 (m, 1H) 2.60 (m, 1H) 2.68-2.81 (m, 1H) 3.34 (s, 1H) 3.45-3.55 (m, 1H) 3.56-3.66 (m, 1H) 3.69-3.82 (m, 3H) 3.88-4.02 (m, 2H) 4.02-4.18 (m, 3H) 4.28 (dd, J=12, 4 Hz, 1H) 7.48 (d, J=8 Hz, 2H) 8.14-8.25 (m, 3H) Retention time: 3.57 min; Isomer 2: $^1$H NMR (400 MHz, MeOD) δ ppm 0.44-0.56 (m, 2H) 0.67-0.79 (m, 2H) 1.45 (s, 3H) 1.66-1.79 (m, 1H) 1.94-2.08 (m, 1H) 2.60 (m, 1H) 2.66-2.80 (m, 1H) 3.35 (d, J=4 Hz, 1H) 3.50 (m, 1H) 3.57-3.65 (m, 1H) 3.65-3.88 (m, 3H) 3.88-3.97 (m, 2H) 3.97-4.15 (m, 3H) 4.28 (dd, J=12, 4 Hz, 1H) 7.48 (d, J=8 Hz, 2H) 8.12-8.27 (m, 3H) Retention time: 5.13 min; Isomer 3: $^1$H NMR (400 MHz, MeOD) δ ppm 0.47-0.56 (m, 2H) 0.70-0.79 (m, 2H) 1.45 (s, 3H) 1.66-1.78 (m, 1H) 1.96-2.07 (m, 1H) 2.60 (m, 1H) 2.66-2.81 (m, 1H) 3.33-3.37 (m, 1H) 3.57-3.71 (m, 2H) 3.71-3.82 (m, 3H) 3.93 (m, 1H) 3.97-4.08 (m, 2H) 4.08-4.15 (m, 2H) 4.28 (dd, J=12, 4 Hz, 1H) 7.48 (d, J=8 Hz, 2H) 8.12-8.26 (m, 3H) Retention time: 8.13 min; and Isomer 4: $^1$H NMR (400 MHz, MeOD) δ ppm 0.48-0.58 (m, 2H) 0.71-0.81 (m, 2H) 1.47 (s, 3H) 1.67-1.82 (m, 1H) 1.99-2.13 (m, 1H) 2.60 (m, 1H) 2.71-2.82 (m, 1H) 3.34-3.37 (m, 1H) 3.58-3.71 (m, 2H) 3.72-3.81 (m, 3H) 3.93-4.02 (m, 2H) 4.03-4.16 (m, 3H) 4.28 (dd, J=12, 4 Hz, 1H) 7.49 (d, J=8 Hz, 2H) 8.13-8.26 (m, 3H) Retention time: 12.45 min.

Preparation: 4 2-chloro-5-(2,2-difluoropropyl)-6a-methyl-6a,7,9,10-tetrahydro-[1,4]oxazino[3,4-h]pteridin-6(5H)-one 2,2-Difluoropropan-1-ol (383 mg, 3.99 mmol) was combined with THF (3 mL). The solution was stirred at room temperature as 4-nitrobenzene-1-sulfonyl chloride (931 mg, 4.20 mmol) was added followed by triethylamine (0.611 mL, 4.39 mmol). After about 28 hours, the reaction mixture was diluted with THF (2 mL) and 4-dimethylaminopyridine (23 mg, 0.188 mmol) was added. After 16 hours the reaction mixture was diluted with 12 mL MTBE and 5 mL water and stirred for 5 minutes before the layers were separated. The organic layer was extracted with 1 M HCl (3 mL), 5% sodium carbonate (3 mL), brine (3 mL), and then water (3 mL). The organic layer was diluted with another 10 mL MTBE and extracted three times with 1 M NaOH (5 mL) and then water (5 mL). The organic layer was dried over sodium sulfate, filtered, concentrated on a rotovap, and dried under vacuum to give 2,2-difluoropropyl 4-nitrobenzenesulfonate (526 mg) as a pale yellow solid.

2-Chloro-6a-methyl-6a,7,9,10-tetrahydro-[1,4]oxazino[3,4-h]pteridin-6(5H)-one (384 mg, 1.508 mmol), 2,2-difluoropropyl 4-nitrobenzenesulfonate (767 mg, 2.73 mmol), cesium carbonate (1240 mg, 3.81 mmol) were combined in DMA (2 mL) at ambient temperature for about 1 hour and then heated in an oil bath at 60° C. After about 22 hours, the reaction mixture was allowed to cool to ambient temperature, diluted reaction mixture with 25 mL EtOAc, transferred to a separatory funnel, and the reaction vessel rinsed twice with 10 mL 1:1 EtOAc/water. An additional 10 mL of water was then added, the layers were mixed and then separated. The organic layer was extracted with water (10 mL) and the combined aqueous layers were extracted with 10 mL of EtOAc, which was then extracted with 5 mL brine. The combined organic layers were dried over sodium sulfate, filtered, and concentrated on a rotovap to give a residue. The residue was combined with isopropanol (5 mL) and heated in an oil bath at 50° C. oil bath. An addition 1.5 mL was added and the solution was allowed to cool to ambient temperature with stirring to give a solid. Collected the solid by filtration, rinse the filter cake with 1 mL isopropanol and air dry for 2 hours, then dry under vacuum to give the title compound.

EXAMPLE: 59

1-cyclopropyl-3-(4-(5-(2,2-difluoropropyl)-6a-methyl-6-oxo-5,6,6a,7,9,10-hexahydro-[1,4]oxazino[3,4-h]pteridin-2-yl)phenyl)urea

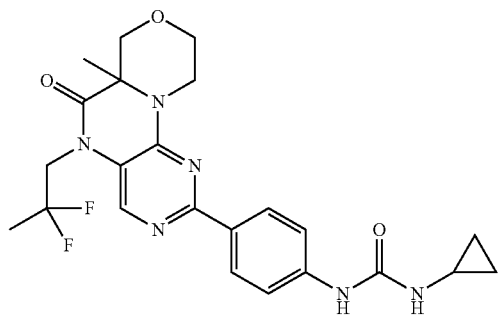

2-Chloro-5-(2,2-difluoropropyl)-6a-methyl-6a,7,9,10-tetrahydro-[1,4]oxazino[3,4-h]pteridin-6(5H)-one (707 mg, 2.125 mmol) and 1-cyclopropyl-3-(4-(4,4,5,5-tetramethyl-1,3,2-dioxaborolan-2-yl)phenyl)urea (770 mg, 2.55 mmol) where combined in methyltetrahydrofuran (10 mL) and aqueous sodium carbonate (2 M) (2.2 mL). The reaction mixture was heated in a 50° C. oil bath and then 1,1-bis(di-tert-butylphosphino)ferrocene palladium dichloride (38 mg) was added. The reaction mixture was then placed in an 80° C. oil bath. After about 1 hour the oil bath was reduced to 74° C. After about 4 hours some solvent had evaporated, 6 mL de-gassed methyltetrahydrofuran was added and decreased the oil bath temperature to 70° C. After about 6 hours, solvent had again evaporated, 6 mL de-gassed methyltetrahydrofuran was added. After another hour, 1,1-bis(di-tert-butylphosphino)ferrocene palladium dichloride (9 mg) was added and heating continued at 70° C. for 3 hours, then cooled to room temperature and allowed to stir overnight. The reaction mixture was then diluted with 4 mL 1:1 methyltetrahydrofuran/water, stir for 15 minutes, the solids were collected by filtration, the filter cake washed with 2×3 mL portions of 1:5 water/methyltetrahydrofuran, air-dried for 1 hour, then under vacuum for 1 hour to give the title compound.

The compounds of the invention can be administered alone or in the form of a pharmaceutical composition. In practice, the compounds of the invention are usually administered in the form of pharmaceutical compositions, that is, in admixture with pharmaceutically acceptable excipients the proportion and nature of which are determined by the properties of the selected compound of the invention, the chosen route of administration, and standard pharmaceutical practice.

In another embodiment, the present invention provides pharmaceutical compositions comprising: a compound of invention and a pharmaceutically acceptable excipient.

In effecting treatment of a patient in need of such treatment, a compound of the invention can be administered in any form and route which makes the compound bioavailable. The compounds of the invention can be administered by a variety of routes, including oral and parenteral routes, more particularly by inhalation, subcutaneously, intramuscularly, intravenously, transdermally, intranasally, rectally, vaginally, occularly, topically, sublingually, and buccally, intraperitoneally, intravenously, intraarterially, transdermally, sublingually, intramuscularly, rectally, transbuccally, intranasally, intraadiposally, intrathecally and via local delivery for example by catheter or stent.

One skilled in the art can readily select the proper form and route of administration depending upon the particular characteristics of the compound selected, the disorder or condition to be treated, the stage of the disorder or condition, and other relevant circumstances. The pharmaceutical compositions of the invention may be administered to the patient, for example, in the form of tablets, capsules, cachets, papers, lozenges, wafers, elixirs, ointments, transdermal patches, aerosols, inhalants, suppositories, solutions, and suspensions.

The pharmaceutical compositions of the present invention are prepared in a manner well known in the pharmaceutical art and include at least one of the compounds of the invention as the active ingredient. The amount of a compound of the present invention may be varied depending upon its particular form and may conveniently be between 1% to about 70% of the weight of the unit dosage form. The term "pharmaceutically acceptable excipient" refers to those typically used in preparing pharmaceutical compositions and should be pharmaceutically pure and non-toxic in the amounts used. They generally are a solid, semi-solid, or liquid material which can serve as a vehicle or medium for the active ingredient. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

The present pharmaceutical compositions are preferably formulated in a unit dosage form, each dosage typically containing from about 0.5 mg to about 200 mg of the compounds of the invention. The term "unit dosage form" refers to a physically discrete unit suitable as a single dosage, each unit containing a predetermined quantity of active ingredient, in association with a suitable pharmaceutical excipient, by which one or more is used throughout the dosing regimen to produce the desired therapeutic effect.

In one particular variation, the composition is a pharmaceutical composition adapted for oral administration, such as a liquid formulation, for example, a solution or suspension, adapted for oral administration or a tablet or a capsule. In still another particular variation, the pharmaceutical composition is a liquid formulation adapted for parenteral administration.

In another embodiment, the invention provides methods of treating conditions associated with mTOR, comprising: administering to a patient in need thereof an effective amount of a compound of the invention. In another embodiment, the invention provides a method of inhibiting a mTOR: comprising, contacting the enzyme with a compound of the invention. In a further embodiment, the invention provides a method of inhibiting a mTOR: comprising, administering a first compound to a subject that is converted in vivo to a compound of the invention.

In another embodiment, compounds of the invention, including the compound of formula I, are provided for use as a medicament. The invention also provides the use of compounds of the invention, including the use for the manufacture of a medicament, to treat the conditions associated with mTOR described herein. The compounds of the present invention are stable and are relatively safe in their end use. The compounds of the present invention are useful as mTOR inhibitors for a variety of subjects (e.g., humans, non-human mammals and non-mammals).

As used herein terms "condition," "disorder," and "disease" relate to any unhealthy or abnormal state. The term "conditions associated with mTOR" includes disorders and diseases in which the inhibition of mTOR provides a therapeutic benefit, such as cancer, allergy/asthma, diseases and conditions of the immune system, inflammation, disease and conditions of the central nervous system (CNS), cardiovascular disease, viral infections, dermatological disease, and diseases and conditions related to uncontrolled angiogenesis, and the like. Where general terms are used herein to describe conditions associated with mTOR it is understood that the more specifically described conditions mentioned in the various diagnostic manuals and other materials are included within the scope of this invention.

For example, it is understood that the treatment of cancer includes treatment of all neoplasia, regardless of their histopathological appearance. Particularly, the cancers that can be treated include, but are not limited to, cancer of blood, including leukemia (including acute myelogenous leukemia, chronic myelogenous leukemia, acute lymphocytic leukemia, chronic lymphocytic leukemia), cancer of the skin, including melanoma, basal cell carcinoma, and squamous cell carcinoma, bone, liver, lung (including small-cell lung tumor, non small-cell lung cancer and bronchioalveolar cancer), brain, breast, prostate, larynx, gall bladder, pancreas, rectum, bile duct, parathyroid, thyroid, adrenal, neural tissue, bladder, spleen, head and neck, included the jaw, mouth, and nose, colon, stomach, testes, esophagus, uterus, cervix and vulva, colorectal, bronchi, bile duct, bladder, kidney, ovary, pancreas, multiple myeloma, lymphomas, basal cell carcinoma, squamous cell carcinoma of both ulcerating and papillary type, osteo sarcoma, Ewing's sarcoma, veticulum cell sarcoma, myeloma, giant cell tumor, islet cell tumor, acute and chronic lymphocytic and granulocytic tumors, hairy-cell tumor, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, myelodysplastic syndrome, mycosis fungicide, rhabdomyosarcoma, astrocytoma, non-Hodgkin's lymphoma, Kaposi's sarcoma, osteogenic and other sarcoma, malignant hypercalcemia, polycythemia vera, adenocarcinoma, glioblastoma multiforma, glioma, lymphomas, epidermoid carcinomas, and other carcinomas and sarcomas.

Benign tumors may also be treated by the mTOR inhibitors of the present invention and include, but are not limited to, hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, and the like, and hamartoma conditions such as Peutz-Jeghers Syndrome (PJS), Cowden disease, Bannayan-Riley-Ruvalcaba Syndrome (BRRS), Proteus syndrome, Lhermitte-Duclos disease and Tuberous Sclerosis (TSC).

The mTOR inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue include emphysema. Repetitive motion disorders that may be treated using the present invention include carpal tunnel syndrome.

The mTOR inhibitors of the invention may also be useful in the prevention of restenosis, that is the control of undesired proliferation of normal cells in the vasculature in response to the introduction of stents in the treatment of vasculature disease.

Proliferative responses associated with organ transplantation that may be treated using mTOR inhibitors of the invention include proliferative responses contributing to potential organ rejections or associated complications. Specifically, these proliferative responses may occur during transplantation of the heart, lung, liver, kidney, and other body organs or organ systems.

The mTOR inhibitors of the invention may also be useful the treatment of abnormal angiogenesis including the abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroplastic), macular degeneration, corneal graft rejection, neuroscular glaucoma, Oster Webber syndrome, retinal/choroidal neuvascularization and corneal neovascularization, Best's disease, myopia, optic pits, Stargart's diseases, Pagets disease, vein occlusion, artery occlusion, sickle cell anemia, sarcoid, syphilis, pseudoxanthoma elasticum carotid obstructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or choroiditis, presumed ocular histoplasmosis, pars planitis, chronic retinal detachment, hyperviscosity syndromes, toxoplasmosis, trauma and post-laser complications, diseases associated with rubesis (neovascularization of the angle), diseases caused by the abnormal proliferation of fibrovascular or fibrous tissue including all forms of proliferative vitreoretinopathy, atopic keratitis, superior limbic keratitis, pterygium keratitis sicca, sjogrens, acne rosacea, phylectenulosis, diabetic retinopathy, retinopathy of prematurity, corneal graft rejection, Mooren's ulcer, Terrien's marginal degeneration, marginal keratolysis, polyarteritis, Wegener sarcoidosis, scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections, and Kaposi sarcoma, Alzheimer's disease, Parkinson's disease amyotrophic lateral sclerosis (ALS), epilepsy, seizures, Huntington's disease, polyglutamine diseases, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

For example, it is understood that the treatment of inflammation include, but are not limited to, acute pancreatitis, chronic pancreatitis, asthma, allergies, chronic obstructive pulmonary disease, adult respiratory distress syndrome. and chronic inflammatory diseases associated with uncontrolled angiogenesis, inflammatory bowel diseases such as Crohn's disease and ulcerative colitis, psoriasis, sarcoidosis, and rheumatoid arthritis, sarcoidosis, and multisystem granulomatous disorder.

For example, it is understood that the treatment of autoimmune includes, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, multiple sclerosis, or Sjoegren's syndrome.

The mTOR inhibitors of the present invention are also useful for treating obesity, diabetes, insulin resistance, metabolic syndrome, and hyperlipidemia.

A wide variety of therapeutic agents may have a therapeutic additive or synergistic effect with mTOR inhibitors according to the present invention. Combination therapies that comprise one or more compounds of the present invention with one or more other therapeutic agents can be used, for example, to: 1) enhance the therapeutic effect(s) of the one or more compounds of the present invention and/or the one or more other therapeutic agents; 2) reduce the side effects exhibited by the one or more compounds of the present invention and/or the one or more other therapeutic agents; and/or 3) reduce the effective dose of the one or more compounds of the present invention and/or the one or more other therapeutic agents. It is noted that combination therapy is intended to cover when agents are administered before or after each other (sequential therapy) as well as when the agents are administered at the same time.

Examples of such therapeutic agents that may be used in combination with the present mTOR inhibitors include, but are not limited to, anti-cell proliferation agents, anticancer agents, alkylating agents, antibiotic agents, antimetabolic agents, hormonal agents, plant-derived agents, and biologic agents.

Examples of such therapeutic agents that may be used in combination with mTOR inhibitors include, but are not limited to, anti-cell proliferation agents, anticancer agents, alkylating agents, antibiotic agents, antimetabolic agents, hormonal agents, plant-derived agents, and biologic agents.

Anti-cell proliferation agents useful in combination with the mTOR inhibitors of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs (0-azetidine-2-carboxylic acid (LACA), cishydroxyproline, d,l-3,4-dehydroproline, thioproline, beta-aminopropionitrile fumarate, 4-propyl-5-(4-pyridinyl)-2(3H)-oxazolone, methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide, angostatic steroid, carboxynaminolmidazole, metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2.

Inhibitors of MEK, MAPK, or ERK kinases are useful in combination with the compounds of the present invention. Specifically, (R)-3-(2,3-Dihydroxypropyl)-6-fluoro-5-(2-fluoro-4-iodophenylamino)-8-methylpyrido[2,3-d]pyrimidine-4,7(3H,8H)-dione useful in combination with the compounds of the present invention. Inhibitors of Hedgehog kinase are useful in combination with the compounds of the present invention. Proteasome inhibitors, in particular bortezomib is useful in combination with the compounds of the present invention.

Alkylating agents useful in combination with the present mTOR inhibitors include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). Combination therapy including a mTOR inhibitor and an alkylating agent is expected to have therapeutic synergistic effects in the treatment of cancer and reduce sides affects associated with these chemotherapeutic agents.

Examples of antibiotic agents useful in combination with the present mTOR inhibitors include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components.

Antimetabolic agents useful in combination with the present mTOR inhibitors include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including a mTOR inhibitor and an antimetabolic agent is expected to have therapeutic synergistic effects on cancer and reduce sides affects associated with these chemotherapeutic agents.

Hormonal agents useful in combination with the present mTOR inhibitors include synthetic estrogens (e.g. diethylstilbestrol), antiestrogens (e.g. tamoxifen, toremifene, fluoxymesterol and raloxifene), antiandrogens (bicalutamide, nilutamide, and flutamide), aromatase inhibitors (e.g., aminoglutethimide, anastrozole and tetrazole), ketoconazole, goserelin acetate, leuprolide, megestrol acetate and mifepristone. Combination therapy including a mTOR inhibitor and a hormonal agent is expected to have therapeutic synergistic effects on cancer and reduce sides affects associated with these chemotherapeutic agents.

Plant-derived agents useful in combination with the present mTOR inhibitors include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including an mTOR inhibitor and a plant-derived agent is expected to have therapeutic synergistic effects on cancer and reduce sides affects associated with these chemotherapeutic agents The terms "treat," "treatment," and "treating" include improvement of the conditions described herein. Also, it is also recognized that one skilled in the art may affect the conditions by treating a patient presently afflicted with the disorders or by prophylactically treating a patient believed to be susceptible to such conditions with an effective amount of a compound of invention. Thus, the terms "treat," "treatment," and "treating" include all processes providing slowing, interrupting, arresting, controlling, or stopping of the state or progression of the conditions described herein, but does not necessarily indicate a total elimination of all symptoms or a cure of the condition, and is intended to include prophylactic and therapeutic treatment of such disorders.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

As used herein, the term "effective amount" refers to the amount of compound of the invention which treats, upon single or multiple dose administration, a patient suffering from the mentioned condition. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to: the species of patient; its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the present use invention, including a compound of the invention, is expected to vary from about 0.1 milligram per kilogram of body weight per day (mg/kg/day) to about 40 mg/kg/day. Specific amounts can be determined by the skilled person.

In a particular embodiment the present invention provides a method for treating cancer, comprising: administering to a patient in need thereof an effective amount of a compound of invention.

The invention also provides an article of manufacture: comprising at least one compound of the invention and a label. The label may include information about the manufacturer, doses, conditions to be treated, and the use of the compound or pharmaceutical composition.

In another embodiment the invention provides a kit: comprising, at least one compound of the invention, a label, and apparatus for administration. The apparatus may include mixing vials, liquids for forming solutions or suspensions, tubing, syringes, and the like.

The activity of compounds as mTOR inhibitors may be determined by a variety of methods, including in vitro and in vivo methods.

Example A Inhibition of mTOR

Purified mTOR are purchased from Invitrogen. mTOR activity was determined using Invitrogen's LanthaScreen system. The inhibitory properties of compounds relative to mTOR may be determined using a black 384-well-plate format in the following buffer 50 mM Hepes, 10 mM NaCl, 10 mM $MgCl_2$, 0.2 mM EDTA, 0.01% Brij35, 2 mM DTT at pH7.3. The test compound is prepared in DMSO using 2 fold serial dilutions for 11 data points which are added to the buffer so that each dilution contains 3% DMSO.

An assay for mTOR inhibition is as follows:

Combine in each well 2 µl of 1.2 µM GFP-4E-BP1 (Invitrogen) and 150 µM ATP (in buffer), 2 µl of diluted test compound (3% DMSO in buffer), and 2 µl of 6 nM mTor in buffer. The reaction mixture is then incubated at room temperature for 30 min, and quenched by adding 40 mM ETDA with 4 nM Tb-anti-p4E-BP1 [pThr46] antibody in TR-FRET dilution buffer (Invitrogen). The plate is kept at room temperature for 1 hour and then read using PheraStar (BMG labtech) LanthaScreen mode.

$pIC_{50}$ values, the negative of the log of the $IC_{50}$, are calculated by non-linear curve fitting of the compound concentrations and percent of inhibition to the standard $pIC_{50}$ equation. The exemplified compounds inhibited human mTOR in the assay of Example A with a $pIC_{50}$ of: A less than about 6, B between 6 and 7.5, and C greater than 7.5 as indicated in Table 1.

TABLE 1

| Example | $pIC_{50}$ | Example | $pIC_{50}$ | Example | $pIC_{50}$ |
| --- | --- | --- | --- | --- | --- |
| 1 | C | 3 | C | 4 | B |
| 5 | C | 6 | B | 7 | C |
| 9 | C | 11 | B | 14 | B |
| 15 | C | 16 | C | 17 | B |
| 18 | C | 19 | B | 20 | A |
| 22 | B | 23 | B | 24 | A |
| 26 | C | 28 | C | 30 | C |
| 35 | C | 36 | C | 41 | C |
| 45 | B | 46 | C | 47 | C |
| 49 | C | 53 | C | | |

What is claimed is:

1. A compound of the formula

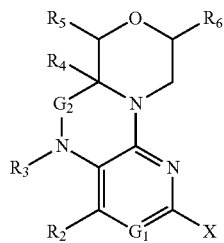

wherein $G_1$ is N;

$G_2$ is selected from the group consisting of C=O and $CH_2$;

X is a halogen;

$R_2$ is selected from the group consisting of hydrogen, halo, cyano, optionally substituted $C_{1-6}$ alkyl, $C_{1-8}$ sulfonyl, optionally substituted $C_{2-4}$ alkenyl, optionally substituted $C_{2-4}$ alkynyl, optionally substituted $C_{1-4}$ alkoxy, $C_{0-8}$ alkylamino, optionally substituted $C_{4-14}$ aryl, optionally substituted $C_{4-14}$ aryloxy, $C_{1-5}$ oxycarbonyl, $C_{1-5}$ carbonyloxy, optionally substituted $C_{3-6}$ heterocycloalkyl, optionally substituted $C_{1-10}$ heteroaryl, hydroxy, and nitro;

$R_3$ is selected from the group consisting of hydrogen, optionally substituted $C_{1-6}$ alkyl, optionally substituted $C_{3-8}$ cycloalkyl, and optionally substituted $C_{3-6}$ heterocycloalkyl;

$R_4$ is selected from the group consisting of methyl and trifluoromethyl;

$R_5$ is selected from the group consisting of hydrogen, halo, optionally substituted $C_{1-6}$ alkyl, optionally substituted $C_{2-4}$ alkenyl, and optionally substituted $C_{3-8}$ cycloalkyl;

$R_6$ is selected from the group consisting of hydrogen, halo, optionally substituted $C_{1-6}$ alkyl, optionally substituted $C_{2-4}$ alkenyl, and optionally substituted $C_{3-8}$ cycloalkyl;

or a pharmaceutically acceptable salt thereof.

2. A compound of claim 1 wherein $G_2$ is C=O.

3. A compound of claim 2 wherein $R_4$ is methyl.

4. A compound of claim 3 wherein $R_2$ is hydrogen.

5. A compound of claim 4 wherein $R_3$ is selected from the group consisting of optionally substituted $C_{1-6}$ alkyl, optionally substituted $C_{3-6}$ heterocycloalkyl, and optionally substituted $C_{3-8}$ cycloalkyl.

6. A compound of claim 5 wherein $R_3$ is selected from the group consisting of $C_{1-4}$ alkyl, $C_{3-8}$ cycloalkyl$C_{1-4}$ alkyl, and $C_{3-8}$ cycloalkyl.

7. A compound of claim 6 wherein $R_5$ is hydrogen and $R_6$ is hydrogen.

8. A compound of any one of claims 1 to 5 wherein X is selected from the group consisting of chloro and bromo.

* * * * *